US007482008B1

(12) United States Patent
Gefter et al.

(10) Patent No.: US 7,482,008 B1
(45) Date of Patent: *Jan. 27, 2009

(54) HUMAN T CELL REACTIVE FELINE PROTEIN (TRFP) ISOLATED FROM HOUSE DUST AND USES THEREFOR

(75) Inventors: Malcolm L. Gefter, Lincoln, MA (US); Richard D. Garman, Arlington, MA (US); Julia L. Greenstein, West Newton, MA (US); Mei-chang Kuo, Winchester, MA (US); Bruce L. Rogers, Belmont, MA (US); Irwin J. Griffith, North Reading, MA (US); Jay P. Morgenstern, Boston, MA (US); Julian F. Bond, Weymouth, MA (US); Andrew W. Brauer, Salem, MA (US); Malcolm Morville, Shrewsbury, MA (US); Thomas J. Briner, Arlington, MA (US); Ze'ev Shaked, Berkeley, CA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/662,784

(22) Filed: Sep. 15, 2000

Related U.S. Application Data

(60) Continuation of application No. 08/431,184, filed on Apr. 28, 1995, now Pat. No. 6,120,769, which is a division of application No. 08/300,928, filed on Sep. 2, 1994, now Pat. No. 6,019,972, which is a continuation-in-part of application No. 08/006,116, filed on Jan. 15, 1993, now abandoned, which is a continuation-in-part of application No. 07/884,718, filed on May 15, 1992, now abandoned, which is a continuation-in-part of application No. 07/857,311, filed on Mar. 25, 1992, now abandoned, which is a continuation-in-part of application No. 07/807,529, filed on Dec. 13, 1991, now Pat. No. 5,547,669, which is a continuation-in-part of application No. 07/662,276, filed as application No. PCT/US90/06548 on Nov. 2, 1990, now abandoned, which is a continuation-in-part of application No. 07/431,565, filed on Nov. 3, 1989, now abandoned.

(51) Int. Cl.
*A61K 39/35* (2006.01)
*A61K 39/00* (2006.01)
*C07K 7/00* (2006.01)
*C07K 7/06* (2006.01)
*C07K 7/08* (2006.01)
*C07K 14/47* (2006.01)
*C07K 1/00* (2006.01)

(52) U.S. Cl. ............ 424/185.1; 424/193.1; 424/275.1; 530/300; 530/324; 530/325; 530/326; 530/327; 530/328; 530/329; 530/350; 435/69.1; 435/69.3; 435/252.3; 435/254.11; 536/23.5; 536/24.1; 514/2; 514/12

(58) Field of Classification Search ................ 530/350, 530/300, 333; 514/2, 12; 435/68.1, 69.1, 435/320.1, 325, 252.3; 424/184.1, 185.1
See application file for complete search history.

(56) References Cited

U.S. PATENT DOCUMENTS

| 3,846,399 | A | * | 11/1974 | Hirschmann et al. ........ 530/342 |
| 4,163,778 | A | | 8/1979 | Ohman et al. |
| 4,338,297 | A | | 7/1982 | Michael et al. ............... 424/91 |
| 6,019,972 | A | * | 2/2000 | Gefter et al. ............. 424/185.1 |
| 6,048,962 | A | * | 4/2000 | Gefter et al. ............. 424/185.1 |

FOREIGN PATENT DOCUMENTS

| WO | WO-91/06571 A1 | 5/1991 |
| WO | WO-92/15613 A1 | 9/1992 |
| WO | WO-93/08280 A1 | 4/1993 |
| WO | WO-93/19178 A2 | 9/1993 |

OTHER PUBLICATIONS

Morgenstern et al., PNAS 88:9690-9694, 1991.*
Littler et al., J. of Virol., 64(2):714-722.*
Sibson et al., WO94/01548 (Jan. 20, 1994), pp. 1-20 and 613-614.*
Harlow & Lane, Cold Spring Harbor Labs, p. 427, 1988.*
Leiterman et al., J. Allergy Clin. Immunol., 74:147-53, 1984.*
UniProt$_{13}$03 alignment with accession No. P30440, Apr. 1, 1993.*
Anderson, M.C. et al., "A comparative study of the allergens of cat urine, serum, saliva, and pelt," *J. Allergy Clin Immunol*, vol. 76:563-569 (1985).
Burgess, W. H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111:2129-2138 (1990).
Chapman, M. D. et al., "Monoclonal Antibodies to the Major Feline Allergen fel d I, II. Single Step Affinity Purification of Fel d I, N-Terminal Sequence Analysis, and Development of a Sensitive Two-Site Immunoassay to Assess Fel d I Exposure," *The Journal of Immunology*, vol. 140(3):812-818 (1988).
de Groot, H. et al., "Monoclonal antibodies to the major feline allergen Fel d I," *J Allergy Clin Immunol*, vol. 82:778-786 (1988).
Didierlaurent, A. et al., "Comparative Study on Cat Allergens from Fur and Saliva," *Int. Archs Allergy appl. Immun.*, vol. 73:27-31 (1984).

(Continued)

*Primary Examiner*—Elizabeth C Kemmerer
*Assistant Examiner*—Gregory S Emch
(74) *Attorney, Agent, or Firm*—Arent Fox LLP

(57) ABSTRACT

A substantially pure, covalently linked human T cell reactive feline protein (TRFP) has been isolated from vacuum bag extract obtained by affinity purification of house dust collected from several homes with cats; DNA encoding all or a portion of the TRFP or peptide; compositions containing such a protein or peptide or portions thereof; and antibodies reactive with the TRFP or peptide are disclosed. Also disclosed are recombinant TRFP or peptide; modified or mutated TRFP peptides; their use for diagnostic or therapeutic purposes.

10 Claims, 41 Drawing Sheets

OTHER PUBLICATIONS

Duffort, O. et al., "Monoclonal antibodies against Fel d I and other clinically relevant cat allergens," *Immunology Letters*, vol. 17:71-77 (1988).

Duffort, O. et al., "Characterization of the Main IgE-Binding Components of Cat Dander," *Int. Archs Allergy appl. Immun.*, vol. 84:339-344 (1987).

Jenkins, M.K. et al., "Antigen Presentation by Chemically Modified Splenocytes Induces Antigen-Specific T Cell Unresponsiveness In Vitro and In Vivo." *Journal of Experimental Medicine*, vol. 165:302-319 (1987).

Kumar, V. et al., "Amino acid variations at a single residue in an autoimmune peptide profoundly affect its properties: T-cell activation, major histocompatibility complex binding, and ability to block experimental allergic encephalomyelitis," *Proc. Natl. Acad. Sci. USA*, vol. 87:1337-1341 (1990).

Lazar, E. et al., "Transforming Growth Factor α: Mutation of Aspartic Acid 47 and Leucine 48 Results in Different Biological Activities," *Molecular and Cellular Biology*, vol. 8(3):1247-1252 (1988).

Leitermann, K. et al., "Cat allergen 1: Biochemical, antigenic, and allergenic properties," *J. Allergy Clin Immunol*, vol. 74:147-153 (1984).

Lerner, R.A., "Tapping the immunological repertoire to produce antibodies of predetermined specificity," *Nature*, vol. 299:592-596 (1982).

Løwenstein, H. et al., "Identification and Clinical Significance of Allergenic Molecules of Cat Origin," *Allergy*, vol. 40:430-441 (1985).

Margalit, H. et al., "Prediction of Immunodominant Helper T Cell Antigenic Sites from the Primary Sequence," *The Journal of Immunology*, vol. 138(7):2213-2229 (1987).

Mester, J.C. et al., "The Mouse Model and Understanding Immunity to Herpes Simplex Virus," *Reviews of Infectious Diseases*, vol. 13(Suppl. 11):S935-945 (1991).

Ohman, J.L. et al., "Allergens of Mammalian Orgin, III. Properties of a Major Feline Allergen," *The Journal of Immunology*, vol. 113(6):1668-1677 (1974).

Ohman, J.L. et al. "Immunotherapy in cat-induced asthma. Double-blind trial with evaluation of in vivo and in vitro responses," *J Allergy Clin Immunol*, vol. 74:230-239 (1984).

Pongor, S. "The USe of Structural Profiles and Parametric Sequence Comparison in the Rational Design of Polypeptides," *Methods in Enzymology*, vol. 154:450-473 (1987).

Salgaller, M.L. et al., "Generation of specific anti-melanoma reactivity by stimulation of human tumor-infiltrating lymphocytes wtih MAGE-1 synthetic peptide," *Cancer Immunology Immunotherapy*, vol. 39:105-116 (1994).

Stone, K. L. et al., "Enzymatic Digestion of Proteins and HPLC Peptide Isolation," *A Practical Guide to Protein and Peptide Purification for Microsequencing, Second Edition*, pp. 43-69 (1993).

Sundin, B. et al., "Immunotherapy with partially purified and standardized animal dander extracts," *J Allergy Clin Immunol*, vol. 77:478-487 (1986).

Ununue, "Immediate Hypersensitivity Reactions and Anaphylaxis," Chapter 14, *Textbook of Immunology, 2nd Edition*, pp. 281-298 (1984).

van Milligen, F.J. et al., "IgE Epitopes of the Cat Allergen Fel d I; A Study with Overlapping Synthetic Peptides," *CLB and Lab Exp. Clin. Immunol., Univ. of Amsterdam*, Abstracts, vol. 89(1, part 2):243 (1982).

Young, R.A. et al., "Efficient isolation of genes by using antibody probes," *Proc. Natl. Acad. Sci. USA*, vol. 80:1194-1198 (1983).

Michael et al., "Modulation of the immune response to ragweed allergens by peptic fragments", *Clin. Exper. Allergy* (1990), 20:669-674.

Morgenstern et al., "Amino acid sequence of Fei d 1, the major allergen of the domestice cat: Protein sequence analysis and cDNA cloning", *Proc. Natl. Acad. Sci.* (1991), 99:9690-9694.

Ota et al., "T Cell recognition of an immunodominant myelin basic protein epitope in multiple sclerosis", *Letters to Nature* (1990), 346:183-187.

Pongor et al. *Methods in Enzymology* (1987) 154:450-473.

Rothbard et al., "A Sequence Pattern Common to T Cell Epitopes", *The EMBO J.* (1988), 7(1):93-100.

Wucherpfennig et al. "Structural Requirements for binding of an Immunodominant Myelin Basic Protein Peptide to DR2 Isotypes and for its recognition by Human T Cell Ciones", *J. Exp. Med.* (1994), 179:279-290.

\* cited by examiner

TRFP CHAIN 1, LEADER A

```
              10         20         30         40         50         60
               |          |          |          |          |          |
        CTGCATCATGAAGGGGGCTCGTGTTCTCGTGCTTCTCTGGGCTGCCTTGCTCTTGATCTG
          C  I  M  K  G  A  R  V  L  V  L  L  W  A  A  L  L  L  I  W
                   ─────────────────────────────────────────────────

70         80         90        100        110        120
               |          |          |          |          |          |
        GGGTGGAAATTGTGAAATTTGCCCAGCCGTGAAGAGGGATGTTGACCTATTCCTGACGGG
          G  G  N  C  E  I  C  P  A  V  K  R  D  V  D  L  F  L  T  G
          ─────────

130        140        150        160        170        180
               |          |          |          |          |          |
        AACCCCCGACGPATATGTTGAGCAAGTGGCACAATACAAAGCACTACCTGTAGTATTGGA
          T  P  D  E  Y  V  E  Q  V  A  Q  Y  K  A  L  P  V  V  L  E 190        200        210        220        230        240
               |          |          |          |          |          |
        AAATGCCAGAATACTGAAGAACTGCGTTGATGCAAAAATGACAGAAGAGGATAAGGAGAA
          N  A  R  I  L  K  N  C  V  D  A  K  M  T  E  E  D  K  E  N 250        260        270        280        290        300
               |          |          |          |          |          |
        TGCTCTCAGCTTGCTGGACAAAATATACACAAGTCCTCTGTGTTAAAGGAGCCATCACTG
          A  L  S  L  L  D  K  I  Y  T  S  P  L  C  -

310        320        330        340        350        360
               |          |          |          |          |          |
        CCAGGAGCCCTAAGGAAGCCACTGAACTGATCACTAAGTAGTCTCAGCAGCCTGCCATGT 370        380        390        400        410
               |          |          |          |          |
        CCAGGTGTCTTACTAGAGGATTCCAGCAATAAAAGCCTGGCAATTCAAACAAAAAAAA
```

Fig. 1

TRFP CHAIN 1, LEADER B

```
          10        20        30        40        50        60
           |         |         |         |         |         |
GGCCTGGCGGTGCTCCTGGAAAAGGATGTTAGACGCAGCCCTCCCACCCTGCCCTACTGT
  A   W   R   C   S   W   K   R   M   L   D   A   A   L   P   P   C   P   T   V 70        80        90       100       110       120
           |         |         |         |         |         |
TGCGGCCACAGCAGATTGTGAAATTTGCCCAGCCGTGAAGAGGGATGTTGACCTATTCCT
  A   A   T   A   D   C   E   I   C   P   A   V   K   R   D   V   D   L   F   L 130       140       150       160       170       180
           |         |         |         |         |         |
GACGGGAACCCCCGACGAATATGTTGAGCAAGTGGCACAATACAAAGCACTACCTGTAGT
  T   G   T   P   D   E   Y   V   E   Q   V   A   Q   Y   K   A   L   P   V   V 190       200       210       220       230       240
           |         |         |         |         |         |
ATTGGAAAATGCCAGAATACTGAAGAACTGCGTTGATGCAAAAATGACAGAAGAGGATAA
  L   E   N   A   R   I   L   K   N   C   V   D   A   K   M   T   E   E   D   K 250       260       270       280       290       300
           |         |         |         |         |         |
GGAGAATGCTCTCAGCTTGCTGGACAAAATATACACAAGTCCTCTGTGTTAAAGGAGCCA
  E   N   A   L   S   L   L   D   K   I   Y   T   S   P   L   C   -   R   S   H 310       320       330       340       350       360
           |         |         |         |         |         |
TCACTGCCAGGAGCCCTAAGGAAGCCACTGAACTGATCACTAAGTAGTCTCAGCAGCCTG 370       380       390       400       410       420
           |         |         |         |         |         |
CCATGTCCAGGTGTCTTACTAGAGGATTCCAGCAATAAAAGCCTTGCAATTCAAACAAAA
```

Fig. 2

TRFP CHAIN 2, LONG FORM

```
              10         20         30         40         50         60
               |          |          |          |          |          |
TGACACGATGAGGGGGGCACTGCTTGTGCTGGCATTGCTGGTGACCCAAGCGCTGGGCGT
  D  T  M  R  G  A  L  L  V  L  A  L  L  V  T  Q  A  L  G  V 70         80         90        100        110        120
               |          |          |          |          |          |
CAAGATGGCGGAAACTTGCCCCATTTTTTATGACGTCTTTTTTGCGGTGGCCAATGGAAA
  K  M  A  E  T  C  P  I  F  Y  D  V  F  F  A  V  A  N  G  N 130        140        150        160        170        180
               |          |          |          |          |          |
TGAATTACTGTTGGACTTGTCCCTCACAAAAGTCAATGCTACTGAACCAGAGAGAACAGC
  E  L  L  D  L  S  L  T  K  V  N  A  T  E  P  E  R  T  A 190        200        210        220        230        240
               |          |          |          |          |          |
CATGAAAAAAATCCAGGATTGCTACGTGGAGAACGGACTCATATCCAGGGTCTTGGATGG
  M  K  K  I  Q  D  C  Y  V  E  N  G  L  I  S  R  V  L  D  G 250        260        270        280        290        300
               |          |          |          |          |          |
ACTAGTCATGACAACCATCAGCTCCAGCAAAGATTGCATGGGTGAAGCAGTTCAGAACAC
  L  V  M  T  T  I  S  S  S  K  D  C  M  G  E  A  V  Q  N  T 310        320        330        340        350        360
               |          |          |          |          |          |
CGTAGAAGATCTCAAGCTGAACACTTTGGGGAGATGAATCTTTGCCACTGATGCCCCTTC
  V  E  D  L  K  L  N  T  L  G  R  -

370        380        390        400        410        420
               |          |          |          |          |          |
TGAGCCCCATCCTCCTGCCCTGTTCTTTACACCTAAAGCTGGAATCCAGACACCTGTCCT 430        440        450        460        470
               |          |          |          |          |
CACCTAATTCACTCTCAATCAGGCTGACTAGAATAAAATAACTGCATCTTAAAAAA
```

Fig. 3

TRFP I CHAIN 2, SHORT FORM

```
           10        20        30        40        50        60
           |         |         |         |         |         |
GACACGATGAGGGGGGCACTGCTTGTGCTGGCATTGCTGGTGACCCAAGCGCTGGGCGTC
 D  T  M  R  G  A  L  L  V  L  A  L  L  V  T  Q  A  L  G  V 70        80        90       100       110       120
           |         |         |         |         |         |
AAGATGGCGGAGACGTGCCCCATTTTTTATGACGTCTTTTTTGCGGTGGCCAATGGAAAT
 K  M  A  E  T  C  P  I  F  Y  D  V  F  F  A  V  A  N  G  N 130       140       150       160       170       180
           |         |         |         |         |         |
GAATTACTGTTGGACTTGTCCCTCACAAAAGTCAATGCTACTGAACCAGAGAGAACAGCC
 E  L  L  D  L  S  L  T  K  V  N  A  T  E  P  E  R  V  A 190       200       210       220       230       240
           |         |         |         |         |         |
ATGAAAAAAATCCAGGATTGCTACGTGGAGAACGGACTCATATCCAGGGTCTTGGATGGA
 M  K  K  I  Q  D  C  Y  V  E  N  G  L  I  S  R  V  L  D  G 250       260       270       280       290       300
           |         |         |         |         |         |
CTAGTCATGATAGCCATCAACGAATATTGCATGGGTGAAGCAGTTCAGAACACCGTAGAA
 L  V  M  I  A  I  N  E  Y  C  M  G  E  A  V  Q  N  T  V  E 310       320       330       340       350       360
           |         |         |         |         |         |
GATCTCAAGCTGAACACTTTGGGGAGATGAATCTTTGCCACTGATGCCCCTTCTGAGCCC
 D  L  K  L  N  T  L  G  R  -

370       380       390       400       410       420
           |         |         |         |         |         |
CATCCTCCTGTCCTGTTCTTTACACCTAAAGCTGGAATCCAGACACCTGTCCTCACCTAA 430       440       450       460
           |         |         |         |
TTCACTCTCAATCAGGCTGACTAGAATAAAATAACTGCATCTTAAAAAA
```

Fig. 4

TRFP CHAIN 2, TRUNCATED SHORT FORM

```
          10        20        30        40        50        60
          |         |         |         |         |         |
GACACGATGAGGGGGGGCACTGCTTGTGCTGGCATTGCTGGTGACCCAAGCGCTGGGCGTC
 D  T  M  R  G  A  L  L  V  L  A  L  L  V  T  O  A  L  G  V 70        80        90       100       110       120
          |         |         |         |         |         |
AAGATGGCGGAGACGTGCCCCATTTTTTATGACGTCTTTTTTGCGGTGGCCAATGGAAAT
 K  M  A  E  T  C  P  I  F  Y  D  V  F  F  A  V  A  N  G  N 130       140       150       160       170       180
          |         |         |         |         |         |
GAATTACTGTTGGACTTGTCCCTCACAAAAGTCAATGCTACTGAACCAGAGAGAACAGCC
 E  L  L  D  L  S  L  T  K  V  N  A  T  E  P  E  R  T  A 190       200       210       220       230       240
          |         |         |         |         |         |
ATGAAAAAAATCCAGGATTGCTACGTGGAGAACGGACTCATATCCAGGGTCTTGGATGGA
 M  K  K  I  Q  D  C  Y  V  E  N  G  L  I  S  R  V  L  D  G 250       260       270       280       290       300
          |         |         |         |         |         |
CTAGTCATGCCATCAACGAATATTGCATGGGTGAAGCAGTTCAGAACACCGTAGAAGATC
 L  V  M  P  S  T  N  I  A  W  V  K  Q  F  R  T  P  -

310       320       330       340       350       360
          |         |         |         |         |         |
  TCAAGCTGAACACTTTGGGGAGATGAATCTTTGCCACTGATGCCCCTTCTGAGCCCCATC 370       380       390       400       410       420
          |         |         |         |         |         |
  CTCCTGTCCTGTTCTTTACACCTAAAGCTGGAATCCAGACACCTGTCCTCACCTAATTCA 430       440       450       460
          |         |         |         |
  CTCTCAATCAGGCTGACTAGAATAAAATAACTGCATCTTAAAAAA
```

Fig. 5

TRFP CHAIN #1 PROTEIN SEQUENCE

```
                                              -20                    -10
C1    Leader A                          C I M K G A R V L V L L W A A L L L I W G G N C
C1    Leader B           A W R C S W K R M L D A A L P P C P T B A A T A D C
                                       5              10             15             20             25             30             35
C1    E I C P A V K R D V D L F L T G T P D E Y V E Q V A Q Y K A L P V V L
PRO.  - - - - - - - - - - - - - - - - - - - - - - - - - - - - - - - - - -
                         40             45             50             55             60             65             70
C1    E N A R I L K N C V D A K M T E E D K E N A L S L L D K I Y T S P L C
PRO.  - - - - - - - - - - - - - - - - - - - - - - - - - - - - - - - - - -
```

Fig. 6

TRFP CHAIN #2 PROTEIN SEQUENCES

```
C2 Leader                                              -10
                                       D T M R G A L L V L A L L V T Q A L G
          5         10        15        20        25        30        35        40
C2L  V R M A E T C P I F Y D V F F A V A N G N E L L D L S L T R V N A T E P E R T
C2S  - - - - - - - - - - - - - - - - - - - - - - - - - - - - - - - - - - - - - -
C2ST - - - - - - - - - - - - - - - - - - - - - - - - - - - - - - - - - - - - - -
PRO. - - - - - - - - - - - - - - - - - - - - - - - - - - - - - - - - X - - - - -
```

Fig. 7A

```
           45        50        55        60        65        70        75        80
C2L    A M K K I Q D C Y V E N G L I S R V L D G L V M T T I S S S K D C M G E A V Q N
C2S    - -   - - - - - - - - - - - - - - - - - - - - - - - I A - N E * * Y - -   - - -
C2ST   - -   - - - - - - - - - - - - - - - - - - - - - - - - - - P S T N I A W V K Q F R T P
PRO.         - - - - - - - - - - - - - - - - - - - - - - T T - S S   ( K ) - -   - - -
                                                         I A   N E 85        90
C2L    T V E D L K L N T L G R
C2S    T V                    -
PRO.   T V    -
       A M
```

Fig. 7B

SEQUENCE

PEPTIDE
NAME

| | |
|---|---|
| X | KRDVDLFLTGTPDEYVEQVAQYKALPV |
| Y | KALPVVLENARILKNCVDAKMTEEDKE |
| Z | FFAVANGNELLLDLSLTKVNATEPER |
| A | EEDKENALSLLDKIYTSPL |
| B | MGEAVQNTVEDLKLNTLGR |
| C | EEDKENALSLLDKIYT |
| D | NALSLLDKIYTSPL |

Fig. 17

| | |
|---|---|
| Fel 32 | VKMAETCPIFYDVFFAVA |
| Fel 33 | FYDVFFAVANGNELLLD |
| Fel 34 | NGNELLLDLSLTKVNATE |
| Fel 35 | SLTKVNATEPERTAMKKI |
| Fel 36 | ERTAMKKIQDCYVENGL |
| Fel 37 | QDCYVENGLISRVLDGLV |
| Fel 38 | ISRVLDGLVMTTISSSKDCM |
| Fel 38-1 | ISRVLDGLVMIAINE**DCM |
| Fel 39 | MTTISSSKDCMGEAVQNTEVELDKLNTLGF |
| Fel 39.1 | MIAINE**DCMGEAVQNTEVELDKLNTLGF |

Fig. 18

```
         BAM HI
C  5' GGGGGATCCAAAGCTCTGCCGGTTGTT 3'
         K  A  L  P  V  V

BAM HI
D  5' GGGGGATCCAAAGCTCTGCCGGTTGTGTTCTGGAAAACGCTCGTATCCTGAAAAACTGCGTTGACGCTAAAATGACCGAA
         K  A  L  P  V  V  L  E  N  A  R  I  L  K  N  C  V  D  A  K  M  T  E
   GAAGACAAAGAA 3'
    E  D  K  E

E  3' CTTCTCTGTTTCTTAAGAAGGCGACAACGATTGCCATTGCTTGACGACGACCTGGACAGAGAC 5'
       E  D  K  E  F  F  A  V  A  N  G  N  E  L  L  D  L  S  L

F  5' CTGGACCTGTCTCTGACCAAAGTTAACGCTACCGAACCGGAACGT 3'
       L  D  L  S  L  T  K  V  N  A  T  E  P  E  R

G  3' TGGCTTGGCCTTGCATTGCACTGCAACTGGACAAGGACTGGCCATGGGCCCTG 5'
                T  E  P  E  R  K  R  D  V  D  L  F  L  T  G  T  P  D

H  5' ACCGGTACCCCGACGAATACGTTGAACAGGTTGCTCAGTACAAAGCTCTGCCGGTTTAGTAGTCTAGACTGCAGAAG
       T  G  T  P  D  E  Y  V  E  Q  V  A  Q  Y  K  A  L  P  V  -  -  XBAI  PSTI
   CTTGGATCCCCC 3'
   HINDIII ECORI
```

Fig. 28A

```
I  3' CGAGACGGCCAAATCATCAGATCTGACGTCTTCGAACCTAGGGG 5'
        A   L   P   V   -  - XBAI PSTI HINDIII ECORI

J  5' GGGGATCCGAAGAAGACAAAGAAAACGCTCTGTCTCTGCTG 3'
      BAM HI  E   E   D   K   E   N   A   L   S   L   L

K  3' GACAGAGACGACCTGTTTAGATGTGGAGAGGCGACTTTCGAGACGGCCAACAAGACCTT 5'
        L   S   L   L   D   K   I   Y   T   S   P   L   K   A   L   P   V   V   L   E

L  3' CGAGTCATGTTTCGAGACGGCCAATACCCACTTCGACAAGTCTTGTGGCAACTT 5'
        A   Q   Y   K   A   L   P   V   M   G   E   A   V   Q   N   T   V   E

M  5' CAGAACACCCGTTGAAGACCTGAAACTGAACACCCTGGGTCGTTGAATGTAACTGCAGAATTCCCC 3'
       Q   N   T   V   E   D   L   K   L   N   T   L   G   R   -            PST I ECORI

N  5' GGGGATCCGAAGAAGACACAAA 3'
      BAM HI  E   E   D   K

O  3' TGAAACCCCTCTACTTACATTGACGTCTTAAGGGG 5'
        T   L   G   R   -              PST I ECORI
```

Fig. 28B

ATGGGTCACCACCACCACCACCACGAATTCCTGGTTCCGCGTGGATCC
M  G  H  H  H  H  H  H  E  F  L  V  P  R  G  S

AAAGCTCTGCCGGTTGTTCTGGAAAACGCTCGTATCCTGAAAAACTGC
K  A  L  P  V  V  L  E  N  A  R  I  L  K  N  C

GTTGACGCTAAAATGACCGAAGAAGACAAAGAATTCTTCGCTGTTGCT
V  D  A  K  M  T  E  E  D  K  E  F  F  A  V  A

AACGGTAACGAACTGCTGGACCTGTCTCTGACCAAAGTTAACGCT
N  G  N  E  L  L  D  L  S  L  T  K  V  N  A

ACCGAACCGGAACGTAAACGTGACGTTGACCTGTTCCTGACCGGTACC
T  E  P  E  R  K  R  D  V  D  L  F  L  T  G  T

CCGGACGAATACGTTGAACAGGTTGCTCAGTACAAAGCTCTGCCGGTT
P  D  E  Y  V  E  Q  V  A  Q  Y  K  A  L  P  V

Fig. 29

5' PRIMERS

XZY CONSTRUCT

```
                     K   R   D   V   D   L
5' XRI     5'-GGGGAATTCAAGAGGGATGTTGACCTA-3'
              ECOR I        X

L   P   V │ F   F   A   V   A   N
5' (X) Z   5'-CTACCTGTA┼TTTTTTGCGGTGGCCAAT-3'
                  X    │        Z

P   E   R │ K   A   L   P   V   V
5' (Z) Y   5'-CCAGAGAGA┼AAGCACTACCTGTAGTA-3'
                  Z    │        Y
```

YXZ CONSTRUCT

```
                     K   A   L   P   V   V
5' YRI     5'-GGGGAATTCAAAGCACTACCTGTAGTA-3'
              ECOR I        Y

D   K   E │ K   R   D   V   D   L
5' (Y) X   5'-GATAAGGAG┼AAGAGGGATGTTGACCTA-3'
                  Y    │        X

L   P   V │ F   F   A   V   A   N
5' (X) Z   5'-CTACCTGTA┼TTTTTTGCGGTGGCCAAT-3'
                  X    │        Z
```

ZXY CONSTRUCT

```
                     F   F   A   V   A   N   G
5' ZRI     5'-GGGGAATTCTTTGCGGTGGCCAATGGA-3'
              ECOR I        Z

K   R   D   V   D   L   P
5' (Z) X   5'-AAGAGGGATGTTGACCTATTC-3'
                            X
```

Fig. 31A

3' PRIMERS

XZY CONSTRUCT

```
              αN  αA  αV  αA  αF  αF |αV  αP  αL  αA  αK  αY
3' X (Z)   5'-ATTGGCCACCGCAAAAAA TACAGGTAGTGCTTTGTA-3'
              Z                  |  X
              αL  αA  αK |αR  αE  αP  αE  αT  αA
3' Z (Y)   5'-TAGTGCTTT TCTCTCTGGTTCAGTAGC-3'
              Y       |              Z

αSTOPαE  αK  αD  αE  αE  αT
3' Y BAM   5'-GGGGATCCTTACTCCTTATCCTCTTCTGT-3'
              BAMH I                  Y
```

YXZ CONSTRUCT

```
              αL  αD  αV  αD  αR  αK |αE  αK  αD  αE  αE  αT
3' Y (X)   5'-TAGGTCAACATCCCTCTT CTCCTTATCCTCTTCTGT-3'
              X                  |  Y
              αA  αF  αF |αV  αP  αL  αA  αK  αY
3' X (Z)   5'-CGCAAAAAA TACAGGTAGTGCTTTGTA-3'
              Z       |              X

αSTOPαR  αE  αP  αE  αT  αA
3' Z BAM   5'-GGGGATCCTTATCTCTCTGGTTCAGTAGC-3'
              BAMH I                  Z
```

ZXY CONSTRUCT

```
              αL  αD  αV  αD  αR  αK |αR  αE  αP  αE  αT  αA  αN
3' Z (X)   5'-TAGGTCAACATCCCTCTT TCTCTCTGGTTCAGTAGCATT-3'
              X                  |  Z
                      αSTOPαE  αK  αD  αE  αE  αT  αM
3' Y BAM   5'-GGGGATCCTCACTCCTTATCCTCTTCTGTCAT-3'
              BAMH I                  Y
```

Fig. 31B

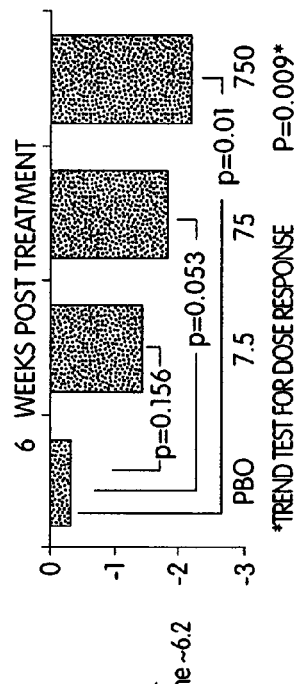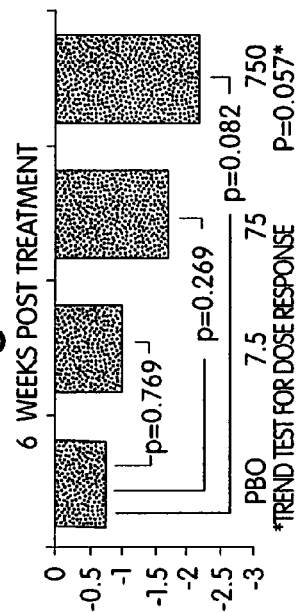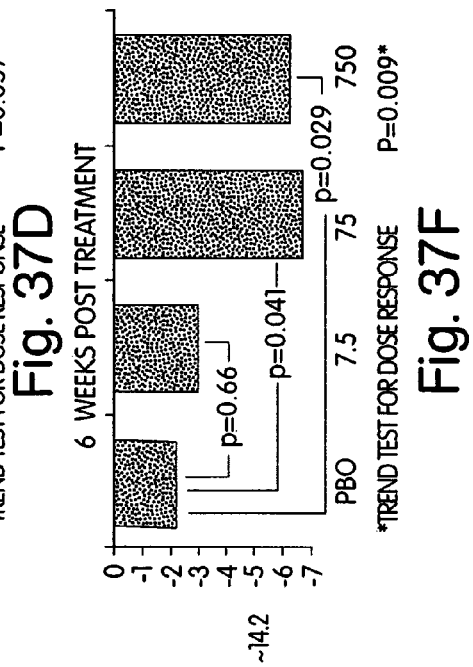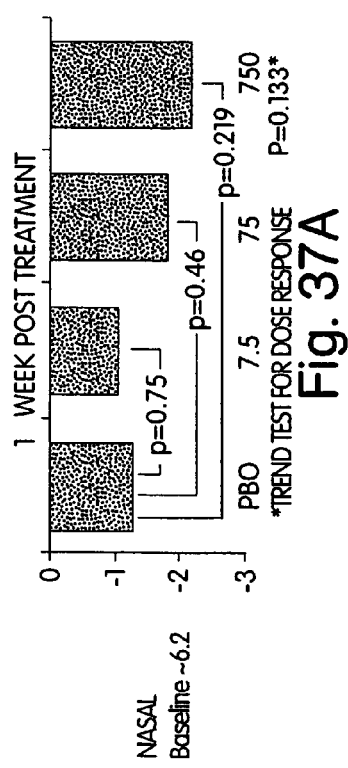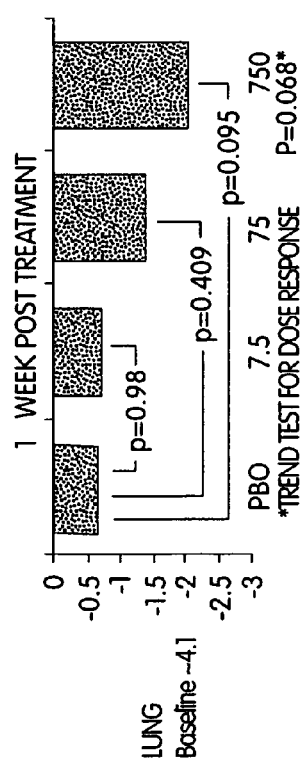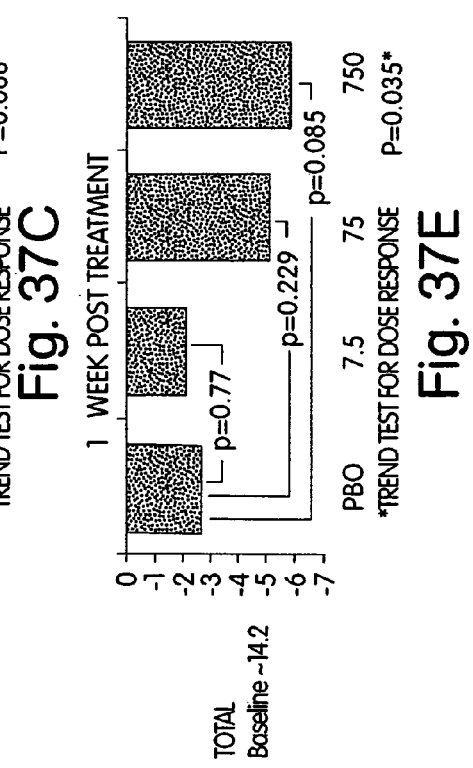

HUMAN T CELL REACTIVE FELINE PROTEIN (TRFP) ISOLATED FROM HOUSE DUST AND USES THEREFOR

RELATED APPLICATIONS

This application is a continuation of U.S. application Ser. No. 08/431,184, filed on Apr. 28, 1995 (now U.S. Pat. No. 6,120,769; issued Sep. 19, 2000), which is a divisional application of U.S. application Ser. No. 08/300,928, filed on Sep. 2, 1994 (now U.S. Pat. No. 6,019,972; issued Feb. 1, 2000), which is a continuation-in-part of U.S. application Ser. No. 07/807,529, filed on Dec. 13, 1991 (now U.S. Pat. No. 5,547,669; issued Aug. 20, 1996). This application is also a continuation-in-part of U.S. Ser. No. 08/006,116, filed Jan. 15, 1993 (now abandoned), which is a continuation-in-part of U.S. Ser. No. 07/884,718, filed May 15, 1992 (now abandoned), which is a continuation-in-part of U.S. Ser. No. 07/857,311, filed Mar. 25, 1992 (now abandoned), which is a continuation-in-part of U.S. Ser. No. 07/662,276, filed Feb. 28, 1991 (now abandoned), which claimed priority to International Application Ser. No. PCT/US90/06548, filed Nov. 2, 1990, and which is a continuation-in-part of U.S. Ser. No. 07/431,565, filed Nov. 3, 1989 (now abandoned). The contents of the above applications are incorporated herein by reference.

BACKGROUND OF THE INVENTION

Genetically predisposed individuals, who make up about 10% of the population, become hypersensitized (allergic) to antigens from a variety of environmental sources to which they are exposed. Those antigens that can induce immediate and/or delayed types of hypersensitivity in people are called allergens. King, T. P., *Adv. Immun.*, 23:77-105 (1976). The symptoms of hay fever, asthma and hives are forms of allergy which can be caused by a variety of allergens, such as products of grasses, trees, weeds, animal dander, insects, food, drugs and chemicals. The antibodies involved in allergy belong primarily to the immunoglobulin E (IgE) class of immunoglobulins. IgE binds to mast cells and basophils. Upon combination of a specific allergen with IgE bound to mast cells, the IgE is cross-linked on the cell surface, resulting in the physiological effects of IgE-antigen interaction. Degranulation results in release mediators including histamine, heparin, a chemotactic factor for eosinophilic leukocytes and the leukotrienes, C4, D4 and E4, vehicle cause prolonged constriction of bronchial smooth muscle cells. Hood, L. E. et al., *Immunology*, (2nd ed.), pp 460-462, The Benjamin/Cumming Publishing Co., Inc. (1984). The effects of allergen on an individual may be systemic or local in nature, depending on the route by which the allergen entered the body and the pattern of deposition of IgE and mast cells. Local manifestations generally occur on epithelial surfaces at the location at which the allergen entered the body. Systemic effects can include anaphylaxis (anaphylactic shock), which is the result of an IgE-basophil response to circulating (intravascular) allergen.

It has been estimated that there are approximately 10 million cat allergic individuals in the United States. Ohman, J. L., and Sundin, B., *Clin. Rev. Allergy*, 5:37-47 (1987). An allergen of particular concern for many people is the feline skin and salivary gland allergen of the domestic cat *Felis domesticus* allergen I (Fel d I), also referred to as allergen I, cat 1 and antigen 4. Fel d I has been reported to be an acidic non-covalently linked homodimer of approximately 39,000 molecular weight on size exclusion HPLC, and 17,000 under nonreducing conditions on gel electrophoresis. Chapman, M. D., et al. *J. Immunology*, 140(3):812-818 (1988). Chapman and co-workers also describe a single step procedure for the purification of Fel d I from crude house dust extract with a high Fel d I content (50 U/ml) using monoclonal antibody affinity chromatography. In addition, they report the amino acid composition and partial amino acid sequence of Fel d I. Fel d I has also been reported to be a 35,000 molecular weight dimer of two noncovalently linked 18,000 molecular weight subunits, which occurs in three isoallergenic forms (pI 3.5 to 4.1). Ohman, J. L., et al., *J. Allergy Clin. Immunol.*, 52:231 (1973); Ohman, J. L., et al., *J. Immunol.*, 113:1668 (1974); Leiterman, K., and Ohman, J. L., *J. Allergy Clin. Immunol.*, 74:147 (1984).

Previous to the present invention, definition or characterization of the structure and components of the Fel d I allergen believed to be responsible for the adverse effects on cat-sensitive individuals was far from complete and current desensitization therapy involves treatment with a complex, ill-defined animal dander extract. However, the presently claimed invention has overcome these deficiencies by providing highly purified and isolated Fel d I (referred to herein as T cell reactive feline protein (TRFP)) free of any other polypeptides and contaminants, as well as identifying those portions of the Fel d I allergen believed to be responsible for causing allergy in cat allergen sensitive individuals. Moreover, the present invention further provides highly characterized therapeutic compositions and methods for treating sensitivity to cats in humans, and which have been further shown to have statistically significant clinical benefit to humans in Phase II clinical trials.

SUMMARY OF THE INVENTION

This invention pertains to a substantially pure human T cell reactive feline protein, referred to as TRFP, DNA encoding all or a portion of the TRFP; compositions containing such a protein or a peptide derived therefrom; and monoclonal antibodies reactive with the TRFP or a peptide derived therefrom. The present inventors are the first to sequence the entire TRFP protein as described herein. As a result of the present work, the amino acid sequence of TRFP as disclosed herein is understood by the art as being the fully characterized, correct full length form of Group I protein derived from *Felis domesticus*, and is now deemed to be the correct Fel d I protein. Previous to the present invention, other researchers made reference to Fel d I protein, however earlier characterization of Fel d I was imprecise until the present invention.

This invention also pertains to TRFP produced by recombinant DNA techniques (recombinant TRFP) and to peptides of TRFP produced by recombinant DNA techniques or by chemical synthesis. It further relates to TRFP, referred to as modified (or mutated) TRFP, in which the amino acid sequence differs from that of the naturally-occurring TRFP by an addition, deletion or substitution of at least one amino acid residue or the presence of another (non-amino acid) component. TRFP produced by recombinant DNA techniques can be glycosylated or non-glycosylated, depending on the host cell used to produce the recombinant protein. As described herein it has been shown that natural TRFP is glycosylated (i.e., is carbohydrate-containing).

Methods of administering any of the forms of TRFP, (i.e., purified native TRFP, recombinant TRFP, modified TRFP) or a peptide derived therefrom, or a composition which includes a form of TRFP or a peptide derived therefrom, to reduce or prevent the adverse effects that exposure to cat allergens normally has on cat-allergic individuals (i.e., to desensitize individuals to cat allergens or block the effects of the allergens) are within the scope of this invention. The invention also features methods of diagnosing sensitivity to *Felis domesticus* in an individual and of predicting peptide(s) or amino acid sequence(s) useful in desensitization regimens. For example, as described herein, it has been shown that there are several peptides present within the TRFP which significantly stimulate T cells from cat allergic individuals. Such peptides have further been shown to affect lymphokine secretion profiles in different ways and in certain cases to anergize or tolerize T cells so that they no longer respond to TRFP. Such peptides can be administered in non-immunogenic form to reduce or abolish an individual's allergic response to a cat allergen. Additionally, these peptides can be administered to cat-allergic individuals or used in ex vivo diagnostic tests to determine which peptides(s) cause the sensitivity. Those peptides determined to be applicable can be used selectively to desensitize a cat-sensitive individual. The term to "desensitize" is defined herein as to decrease the allergic-reactivity of a cat-sensitive individual to exposure to cats, cat dander or products thereof (to a level less than that which the cat-sensitive individual would otherwise experience).

This invention further pertains to modified TRFP protein and to modified TRFP peptides derived from TRFP comprising at least one T cell epitope; compositions containing modified TRFP or modified TRFP peptides derived therefrom; and to methods of administering the modified TRFP or modified TRFP peptides, alone or in combination, to reduce or prevent adverse effects that the unmodified, "naturally occurring" or "native" protein has on cat sensitive individuals.

DNA of this invention encoding all or a portion of the TRFP can be used as probes to locate equivalent sequences present in other species (e.g., goat, sheep, dog, rabbit, horse) that may be useful in a diagnostic and/or a therapeutic applications.

BRIEF DESCRIPTION OF THE DRAWINGS

FIG. 1 is the DNA sequence (SEQ. ID. NO: 1) and deduced amino acid sequence (SEQ. ID. NO: 2) of TRFP, chain 1, leader A (underlined).

FIG. 2 is the DNA sequence (SEQ. ID. NO: 3) and deduced amino acid sequence (SEQ. ID. NO: 4) of TRFP, chain 1, leader B (underlined).

FIG. 3 is the DNA sequence (SEQ. ID. NO: 5) and deduced amino acid sequence (SEQ. ID. NO: 6) of TRFP, chain 2, long form (476 nucleotides).

FIG. 4 is the DNA sequence (SEQ. ID. NO: 7) and deduced amino acid sequence (SEQ. ID. NO: 8) of TRFP, chain 2, short form (469 nucleotides).

FIG. 5 is the DNA sequence (SEQ. ID. NO: 9) and deduced amino acid sequence (SEQ. ID. NO: 10) of TRFP, chain 2, truncated form (465 nucleotides).

FIG. 6 is the protein sequence of TRFP, Chain 1, with leader A and leader B (top two lines). The deduced amino acid sequence of the leaders and for Chain 1 (C1) (SEQ. ID. NOS: 11 and 12) were obtained by sequencing cDNA and the protein sequence for Chain 1 (PRO) (SEQ. ID. NOS: 11 and 12) was determined by protein sequencing methods, with amino acid numbering based upon the first amino acid residue determined by protein sequencing methods. The presumed initiator methionine in each leader sequence is in bold type. (-) symbolizes complete agreement or identity with the amino acid residue listed above the (-).

FIG. 7 is the protein sequence of TRFP, Chain 2 with the leader sequence. The deduced amino acid sequence of the leader and for Chain 2 (C2) were obtained by sequencing cDNA. The protein sequence for Chain 2 (PRO) (SEQ. ID. NO: 16) was determined by protein sequencing methods, with amino acid numbering based upon the first amino acid and polymorphism detected by protein sequencing methods noted. C2L: chain 2 long (92 amino acids) (SEQ. ID. NO: 13); C2S: chain 2 short (90 amino acids) (SEQ. ID. NO: 14); C2ST chain 2 short truncated (80 amino acids) (SEQ. ID. NO: 15). The presumed initiator methionine in the leader sequence is in bold type and the potential N-glycosylation site is underlined. (-) symbolizes complete agreement or identity with the amino acid residue listed above the (-).

FIGS. 15A and 15B are graphic representations of the induction of T cell unresponsiveness in mice primed with TRFP and tolerized with peptide Y. Lymph node cells were isolated, cultured in vitro with peptide Y and cell culture supernatants tested for the ability to support the growth of CTLL-2 or CT4S, an IL-4 dependent T cell clone.

FIG. 17 shows the amino acid sequences of peptide X (SEQ. ID. NO: 17), peptide Y (SEQ. ID. NO: 18), peptide Z (SEQ. ID. NO: 19), peptide A (SEQ. ID. NO: 20), peptide B (SEQ. ID. NO: 21), peptide C (SEQ. ID. NO: 22) and peptide D (SEQ. ID. NO: 23) derived from TRFP.

FIG. 18 shows the amino acid sequences of the following peptides: Fel 33 (SEQ. ID. NO: 24), Fel 34 (SEQ. ID. NO: 25), Fel 35 (SEQ. ID. NO: 26), Fel 36 (SEQ. ID. NO: 27), Fel 37 (SEQ. ID. NO: 28), Fel 38 (SEQ. ID. NO: 29), Fel 38-1 (SEQ. ID. NO: 30), Fel 39 (SEQ. ID. NO: 31) and Fel 39.1 (SEQ. ID. NO: 32).

FIG. 28 is the nucleic acid sequences of oligonucleotides C, D, E, F, G, H, and I used in the construction of the peptide YZX and oligonucleotides J, K, L, M, N and O used in the construction of the peptide AYZXB.

FIG. 29 is the nucleic acid sequence (utilizing E. coli expression codons) and the deduced amino acid sequence comprising peptide YZX (SEQ ID NOS:102 and 103) A thrombin cleavage site is shown.

FIG. 31 is the nucleic acid sequences of primers used in the construction of peptides XZY, YXZ, and ZXY.

FIG. 37 is a graphic representation of catroom aggravation (nasal, lung and total allergy) at one and six weeks post treatment with pairwise comparisons versus placebo (PBO) for total allergy symptoms at 75 µg and 750 µg at six weeks, trend tests for dose response at one and six weeks for total allergy symptoms are indicated (see starred data).

DETAILED DESCRIPTION OF THE INVENTION

Figure 8:
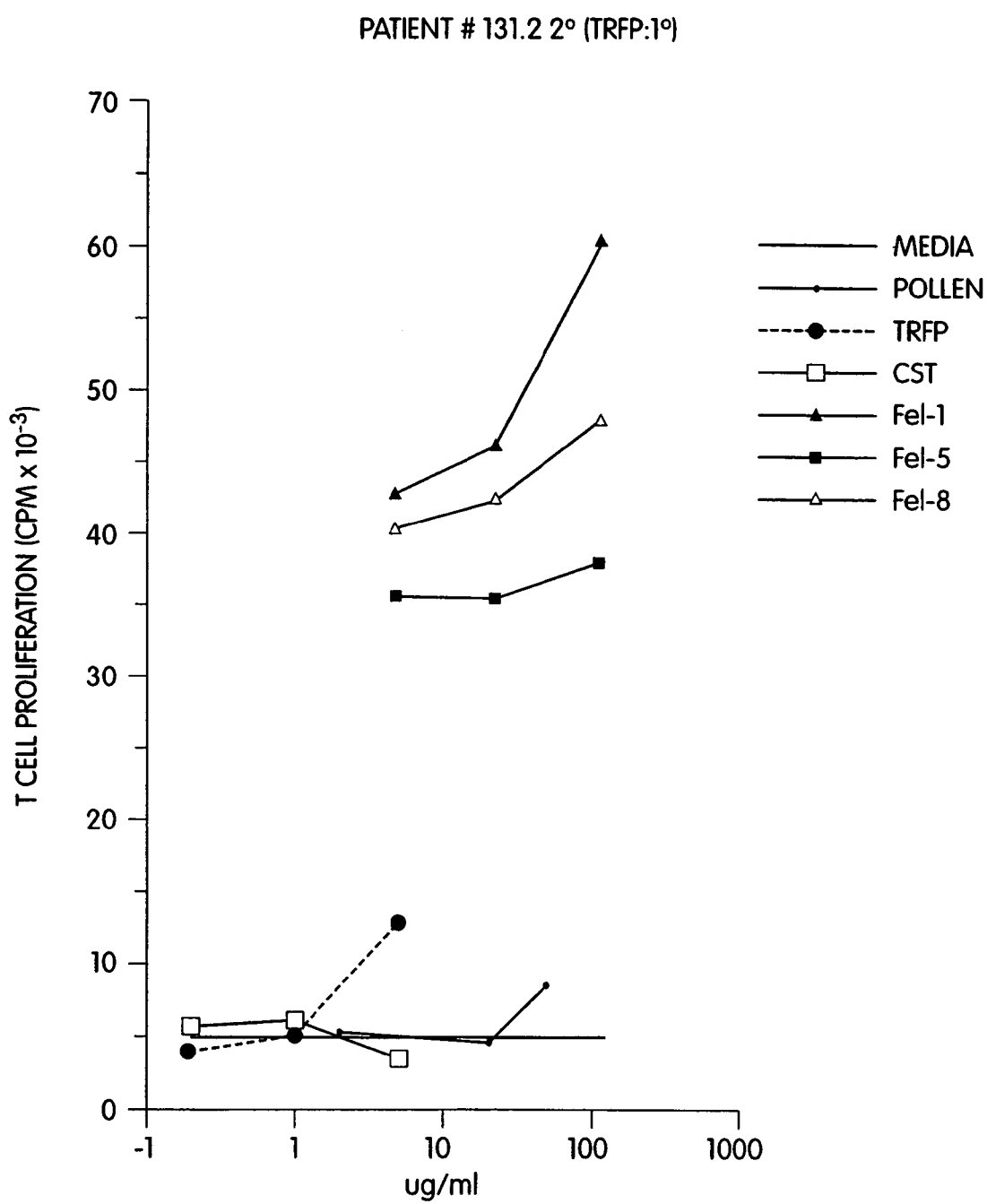
FIG. 8 is a graphic representation of the secondary T cell response of peripheral blood lymphocytes from patient 131 stimulated with various antigens and peptides.

As described herein, a cat protein allergen, human T cell reactive feline protein (TRFP) has been isolated and purified by affinity purification of vacuum cleaner bag house dust collected from several homes with cats. As used herein, "isolated" refers to the TRFP protein or peptides free of all other cat polypeptides or contaminants. The work described herein has resulted in isolation and purification of a TRFP protein; determination of the nucleotide sequence encoding TRFP and the amino acid sequence of TRFP (FIGS. 1-7); demonstration that TRFP is composed of two covalently linked peptide chains (designated chain 1 and 2); identification and isolation of T cell reactive peptides (i.e. peptides comprising at least one T cell epitope) and amino acid sequences present in the TRFP protein; and characterization of TRFP. It has also resulted in cloning and expression of TRFP in E. coli and characterization of the resulting recombinant TRFP proteins. Moreover, the work described herein has resulted in clinical research confirming that the work described herein has provided a therapeutic which has been shown to provide statistically significant clinical benefit to humans allergic to cat allergen in Phase II Clinical Trials. As described in Example 4, cDNA clones encoding all or part of TRFP chain 1 or chain 2 have been expressed in E. coli as recombinant fusion proteins. Of note is the finding that chain 1 of the two-chain TRFP protein has two alternative leader sequences and that chain 2 has two major forms (designated as long and short).

A monoclonal antibody reactive with Felis domesticus allergen I, known as Fel d I, was used to isolate a single protein from a vacuum cleaner bag preparation. The affinity purified T cell reactive protein isolated in this manner is referred to as human T cell reactive feline protein (human TRFP). TRFP has been shown to havebiological activity (human IgE binding ability) and to possess cross reactivity with rabbit anti-Fel d I antisera. The terms "antigenic" or "allergenic" as used interchangeably herein refers to those peptides or proteins which have the ability to induce an immune response (i.e. bind IgE and/or stimulate T-cells).

In addition to determining the amino acid sequence of chains 1 and 2 of the TRFP, a Fel d I protein preparation provided by Martin Chapman was analyzed and the protein was isolated and sequenced. Comparison of the amino acid sequence of the affinity purified TRFP with that of the published Fel d I protein sequence showed that there is a high degree of homology between the first 33 amino acid sequences at the amino terminus of Fel d I and chain 1 of TRFP.

The following is a description of the methods by which a single protein composed of two covalently linked chains was isolated from house dust, as well as a description of approaches used to identify and isolate DNA encoding the TRFP. Furthermore, a description of methods used to generate recombinant TRFP chains 1 and 2 are also presented. Additionally, peptides derived from the TRFP protein having T cell stimulating activity (i.e., the peptide comprises at least one T cell epitope) have been identified and are described herein.

Isolation of a Single Protein From a Vacuum Cleaner Bag Preparation

A protein preparation was extracted from the contents of vacuum cleaner bags by a method based on that of M. D. Chapman and co-workers. Chapman, M. D. et al., *J. Immunol.,* 140(3): 812-818 (1988). Monoclonal antibody reactive with Fel d I, produced by Chapman and co-workers, was used to identify a protein in the preparation. de Groot, H. et al., *J. Allergy Clin. Immunol.,* 82:778-786 (1988). Selected monoclonal antibodies (designated 1G9 and 6F9) that recognize Fel d I native protein were used to affinity purify a protein, which is referred to as human T cell reactive feline protein (TRFP) (also referred to as VCB or vacuum cleaner bag protein) from a house dust sample. This was carried out, using known techniques, by producing the desired monoclonal antibody, isolating it in large quantities from ascites and immobilizing it on Sepharose 4B (Pharmacia). The protein preparation was extracted from vacuum cleaner bags of house dust obtained from several homes with cats. Aqueous vacuum cleaner bag extract was first subjected to gel filtration and decolorization and, subsequently, affinity chromatography purification. Aqueous vacuum cleaner bag extract was passed over the monoclonal antibody-containing column and a protein species was eluted. The protein isolated in this manner was shown, using both Western blot and ELISA techniques, to bind human IgE, thus demonstrating that TRFP possesses allergenic activity. The affinity purified TRFP was subjected to a number of protein chemical procedures to derive primary amino sequence data. The sequences derived from TRFP are illustrated in FIGS. 6 and 7. The methods used in the protein sequence analysis are further described in Example 1. Under non-reducing conditions, Western blot analysis demonstrated the existence of a 40 kD and a 20 kD species, whereas a 10-18 kD and a 5 kD species was detected under reducing conditions.

The 5 kD band interacts with affinity purified antipeptide antisera raised against peptides derived from chain 1 protein sequence (anti-Fel 2 and anti-Fel 4), whereas the 10-18 kD band interacts with antipeptide antiserum raised against peptide derived from chain 2 protein sequence (anti-Fel 18). Hence, the 5 kD band and the 10-18 kD band are derived from the TRFP chain 1 and the chain 2, respectively. TRFP can exist as an aggregated form, as demonstrated by the approximately 40 kD molecular weight of the affinity purified TRFP (may be a dimer of the chain 1 and chain 2 heterodimer) and the approximately 130 kD species detected in gel filtration prior to affinity purification.

Identification of Clones Containing DNA Inserts Encoding the Human T Cell Reactive Feline Protein (TRFP)

Protein chemical analysis of affinity purified TRFP led to the determination that TRFP is composed of two covalently linked peptide chains (designated chain 1 and 2; see Example 1 and the materials and methods section and the discussion section in Morgenstern et al., *Proc. Natl. Acad. Sci., USA,* 88:9690-9694 (1991) for details). Without this information, cloning the full length TRFP protein was not possible. As described in the Examples and the cited paper, chemical analysis of TRFP chemical analysis of TRFP and the discovery that the protein was two covalently linked chains required elegant and uniques experimentation. Furthermore, chain 1 and chain 2, peptide sequence analysis led to the determination of considerable primary sequence data for both chain 1 (70 amino acids; see FIG. 6) and chain 2 (83 amino acids; see FIG. 7). The amino acid sequence data was used to devise various cloning strategies to enable the cloning and complete nucleotide sequence determination of cDNAs and genomic clones encoding the TRFP chains 1 and 2 (details provided in Examples 2 and 3).

In order to determine the best tissue source(s) to isolate mRNA for the cloning of TRFP, various cat tissues were examined by ELISA techniques using monoclonal antibodies (directed against Fel d I). It was determined that the several salivary glands and skin contain significant levels of TRFP, and thus, provide a valuable source from which to clone cDNA sequences encoding the TRFP (see Table 1, in which— indicates that an analysis was not done).

TABLE 1

| | Micrograms TRFP/gram tissue | | | | |
|---|---|---|---|---|---|
| Tissue | Cat 1 | Cat 2 | Cat 3 | Cat 4 | Cat 5 |
| Parotid | 1.03 | 1.41 | 0.81 | 0.32 | 0.30 |
| Mandibular | 0.41 | 2.39 | 7.50 | 2.50 | 4.66 |
| Sublingual | 0.77 | — | 0.50 | 3.18 | 3.82 |
| Zygomatic | — | — | 2.07 | 8.50 | 10.9 |
| Molar | — | — | 7.58 | 1.47 | 25.00 |
| Palate | — | — | 1.03 | 0.53 | 0.77 |
| Washed Skin | 5.80 | 2.30 | — | — | — |

As a result of the work described herein, cDNAs and genomic clones encoding chain 1 and chain 2 of TRFP have been cloned, isolated and sequenced; the encoded amino acid sequences of the protein has been deduced; and peptides derived from TRFP have been identified and isolated using known methods. The complete nucleotide sequences encoding both TRFP chains are shown in FIGS. 1-5. The hybridization pattern of individual genomic clones verified that the chain 1 and chain 2 cDNAs are products of different genes. Northern blot analysis of the cat salivary gland RNA also demonstrated the presence of the two separate mRNAs. Sequencing of the genomic clones confirmed the hybridization results. As described in Example 2, individual full-length PCR generated chain 1 clones were shown to have two different sequences at their 5' ends, suggesting that chain 1 has two alternative leader sequences. This was confirmed by the DNA sequence analysis of the chain 1 genomic clone, which demonstrated that the single chain 1 gene has both alternative leader sequences closely linked at the 5' end of the structural gene (see FIGS. 1, 2 and 6).

As described in Example 4, cDNA clones encoding all or a fragment of TRFP chain 1 or chain 2 were subcloned into *E. coli* expression vectors and the expressed recombinant TRFP proteins examined. Western blot analysis using rabbit antipeptide antisera directed against either chain 1 sequences or chain 2 sequences demonstrated appropriate binding specificity.

Uses of the Subject Human T Cell Reactive Feline Protein (TRFP) and DNA Encoding Same The materials resulting from the work described herein, as well as compositions containing these materials, can be used in methods of diagnosing, treating and preventing cat allergy. In addition, the cDNA (or the mRNA from which it was reverse transcribed) can be used to identify similar sequences in other species and, thus, to identify or "pull out" sequences that have sufficient homology to hybridize to the TRFP cDNA. Such sequences from other species might encode proteins useful in treating allergies to these animals in people. This can be carried out, for example, under conditions of low stringency and those sequences having sufficient homology (generally greater than 40%) can be selected for further assessment using the method described herein. Alternatively, high stringency conditions can be used. In this manner, DNA of the present invention can be used to identify, in other types of mammals (e.g., dog, rabbit, sheep, goat, horse), sequences encoding peptides having amino acid sequences similar to that of the TRFP. This can be done by hybridization or PCR cloning methods. Thus, the present invention includes not only the TRFP or peptide encoded by the present DNA sequences, but also other TRFP-like proteins or peptides encoded by DNA which hybridizes to DNA of the present invention.

Isolated purified native TRFP or a peptide derived therefrom encoded by the cDNA of the present invention can be used, for example, as "purified" TRFP, in a composition to treat cat-allergic individuals, in a method to diagnose cat allergy, or in the standardization of allergen extracts which are key reagents for the diagnosis and treatment of cat allergy. Through use of the protein or peptides of the present invention, preparations of consistent, well-defined composition and biological activity can be made and administered for therapeutic purposes (e.g., to modify the allergic response of a cat-sensitive individual to cat allergies). Such a protein or peptide (or modified version thereof, such as is described below) may, for example, modify B-cell response to cat-allergen, T-cell response to cat allergen or both responses. Purified TRFP (including purified native TRFP) or a peptide derived therefrom can also be used to study the mechanism of immunotherapy of cat allergy and to design modified derivatives, analogues or functional equivalents that are more useful in immunotherapy than are the unmodified ("naturally-occurring" or "native") protein or peptide.

As used herein, the functional equivalent of a peptide includes peptides having the same or enhanced ability to bind MHC; peptides capable of stimulating the same T cell subpopulations; peptides having the same or increased ability to induce T cell responses such as stimulation (proliferation or cytokine secretion), peptides having the same or increased ability to induce T cell unresponsiveness or reduced responsiveness, peptides having reduced IgE binding, and peptides which elicit minimal IgE synthesis stimulating activity. Minimal IgE stimulating activity refers to IgE synthesis stimulating activity that is less than the amount of IgE production elicited by purified native TRFP.

Peptide fragments of TRFP may be obtained, for example, by screening peptides recombinantly. produced from the corresponding fragment of the nucleic acid sequence of the invention coding for such peptides or synthesized chemically using techniques known in the art, or fragments may be produced by chemical cleavage of the native allergen as is known in the art. The allergen may be arbitrarily divided into fragments of a desired length with no overlap of the peptides, or preferably divided into overlapping fragments of a desired length. The fragments are tested to determine their antigenicity (e.g. the ability of the fragment to induce an immune response such as T cell proliferation, lymphokine secretion, or histamine release). Additionally, antigenic fragments comprising "cryptic epitopes" may be determined. Cryptic epitopes are those determinants in a protein antigen which, due to processing and presentation of the native protein antigen to the appropriate MHC molecule, are not normally revealed to the immune system. However, when a subject is primed with a peptide comprising a cryptic epitope, T cells obtained from the subject will proliferate in vitro in response to the peptide or the protein antigen from which the peptide is derived. Peptides which comprise at least one cryptic epitope derived from a protein antigen are referred to herein as cryptic peptides. To confirm the presence of cryptic epitopes in the above-described assay, antigen-primed T cells are cultured in vitro in the presence of each peptide separately to establish peptide-reactive T cell lines. A peptide is considered to comprise at least one cryptic epitope if a T cell line can be established with a given peptide and T cells are capable of proliferation upon challenge with the peptide and the protein antigen from which the peptide is derived.

If peptide fragments of TRFP are to be used for therapeutic purposes, then the fragments of TRFP which are of inducing T cell non-responsiveness are particularly desirable. As used herein, "T cell non-responsiveness", "T cell anergy", and "T cell tolerance" are used interchangeably to refer to T cells which have been down-regulated or rendered completely non-responsive to challenge with a protein or peptide of the invention. While not being limited to any theory, it is has been shown that peptides that are capable of eliciting a T cell response such as stimulation (i.e. proliferation or lymphokine secretion) when administered in non-immunogenic form (to an individual primed with the offending protein or a peptide thereof) are then capable of inducing T cell non-responsiveness when administered in non-immunogenic form (Jenkins, M. K., and Schwartz, R. H. *J. Exp. Med.* 165:302-319 (1987)). Additionally, peptide fragment that have been modified so that they no longer stimulate T cells but are capable of inducing T cell non-responsiveness are desirable to be used in a therapeutic treatment. Peptide fragments of TRFP which have minimal IgE stimulating activity are also desirable. Additionally, for therapeutic purposes, it is preferable to use TRFP or a fragment thereof which does not bind IgE specific for TRFP or bind such IgE to a substantially-lesser extent (i.e., at least 100-fold less binding and more preferably at least 1,000-fold less binding) than the purified native TRFP protein allergen binds such IgE. If the isolated TRFP or fragment thereof binds IgE, it is preferable that such binding does not result in the release of mediators (e.g., histamines) from mast cells or basophils.

Screening peptides of TRFP for the desired activity as described herein can be accomplished using one or more of several different assays. For example, in vitro, TRFP T cell stimulatory activity is assayed by contacting a protein or peptide known or suspected to contain a TRFP T cell epitope with an antigen presenting cell which presents appropriate MHC molecules in a T cell culture. Presentation of a peptide of TRFP in association with appropriate MHC molecules to T cells in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci. USA,* 86:1333 (1989) the pertinent portions of which are incorporated herein by reference. A kit for an assay for the production of interferon is also available from Genzyme Corporation (Cambridge, Mass.).

A common assay for T cell proliferation entails measuring tritiated thymidine incorporation into the DNA of dividing cells. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

In another embodiment, a TRFP peptide is screened for the ability to reduce T cell responsiveness. The ability of a peptide known to stimulate T cells, to inhibit or completely block the activity of a purified native TRFP protein or portion thereof and induce a state of T cell non-responsiveness or reduced T cell responsiveness, can be determined using subsequent attempts at stimulation of the T cells with antigen presenting cells that present native TRFP or portion thereof following exposure to a TRFP peptide. If the T cells are unresponsive to the subsequent activation attempts as determined by, for example, interleukin-2 synthesis and T cell proliferation, a state of unresponsiveness has been induced. See, e.g., Gimmi, et al. (1993) *Proc. Natl. Acad. Sci. USA*, 90:6586-6590; and Schwartz (1990) *Science*, 248:1349-1356, for assay systems that can be used as the basis for an assay in accordance with the present invention.

In yet another embodiment, peptides of TRFP, are identified by IgE binding activity. For therapeutic purposes, peptides of the invention preferably do not bind IgE specific for TRFP, or bind such IgE to a substantially lesser extent (e.g., at least 100 fold less and more preferably, at least 1000 fold less binding) than the corresponding purified native TRFP binds IgE. If a peptide of the invention is to be used as a diagnostic reagent, it is not necessary that the peptide or protein have reduced IgE binding activity compared to the native TRFP. IgE binding activity of peptides can be determined by, for example, an enzyme linked immunosorbent assay (ELISA) using, for example, sera obtained from a subject, (i.e., an allergic subject) that has been previously exposed to the native TRFP or portion thereof. Briefly, a peptide to be tested is coated onto wells of a microtiter plate. After washing and blocking the wells, antibody solution consisting of the plasma of an allergic subject who has been exposed to the peptide being tested or the protein from which it was derived is incubated in the wells. The plasma is generally depleted of IgG before incubation. A labeled secondary antibody is added to the wells and incubated. The amount of IgE binding is then quantified and compared to the amount of IgE bound by a purified native TRFP. Alternatively, the binding activity of a peptide can be determined by Western blot analysis. For example, a peptide to be tested is run on a polyacrylamide gel using SDS-PAGE. The peptide is then transferred to nitrocellulose and subsequently incubated with sera from an allergic subject. After incubation with the labeled secondary antibody, the amount of IgE bound is then determined and quantified.

Another assay which can be used to determine IgE binding activity of a peptide is a competition ELISA assay. Briefly, an IgE antibody pool is generated by combining plasma from TRFP allergic subjects that have been shown by direct ELISA to have IgE reactive with native TRFP. This pool is used in ELISA competition assays to compare IgE binding to native TRFP to the peptide tested. IgE binding for the native TRFP and the peptide being tested is determined and quantified.

If a peptide of TRFP binds IgE, and is to be used as a therapeutic agent, it is preferable that such binding does not result in the release of mediators (e.g., histamines) from mast cells or basophils. To determine whether a peptide which binds IgE results in the release of mediators, a histamine release assay can be performed using standard reagents and protocols obtained for example, from Amac, Inc. (Westbrook, Me.). Briefly, a buffered solution of a peptide to be tested is combined with an equal volume of whole heparinized blood from an allergic subject. After mixing and incubation, the cells are pelleted and the supernatants are processed and analyzed using a radioimmunoassay to determine the amount of histamine released.

Isolated, purified TRFP or preferred fragments thereof, when administered to a cat allergen-sensitive individual, or an individual allergic to an allergen immunologically cross-reactive with TRFP are capable of modifying the allergic response of the individual to a cat allergen or such cross-reactive allergen of the individual, and preferably are capable of modifying the B-cell response, T-cell response or both the B-cell and the T-cell response of the individual to the allergen. As used herein, modification of the allergic response of an individual sensitive to TRFP or cross-reactive allergen can be defined as non-responsiveness or diminution in symptoms to the allergen, as determined by standard clinical procedures (See e.g. Varney et al, *British Medical Journal*, 302:265-269 (1990)) including diminution in cat allergen induced asthmatic symptoms. As referred to herein, a diminution in symptoms includes any reduction in allergic response of an individual to the allergen after the individual has completed a treatment regimen with a peptide or protein of the invention. This diminution may be subjective (i.e., the patient feels more comfortable in the presence of the allergen). Diminution in symptoms can be determined clinically as well, using standard skin tests as is known in the art.

Isolated TRFP or fragment thereof is preferably tested in mammalian models of cat allergen sensitivity such as the mouse model disclosed in Tamura et al. (1986) *Microbiol. Immunol.* 30: 883-896, or U.S. Pat. No. 4,939,239; or the primate model disclosed in Chiba et al. (1990) *Int. Arch. Allergy Immunol.* 93: 83-88. Initial screening for IgE binding to the protein or fragments thereof may be performed by scratch tests or intradermal skin tests on laboratory animals or human volunteers, or in in vitro systems such as RAST (radioallergosorbent test), RAST inhibition, ELISA assay, radioimmunoassay (RIA), or histamine release.

The work described herein has resulted in identification of peptides derived from TRFP which have T cell stimulating activity (i.e., T cell proliferation when administered to an individual primed with the peptide or entire TRFP, lymphokine secretion and/or induction of T cell non-responsiveness) and, thus, comprise at least one T cell epitope. Peptide fragments of TRFP comprising at least one T cell epitope are particularly desirable. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T cell epitope is the basic element or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Exposure of cat sensitive patients to the isolated protein of the invention or to the peptide fragments of the invention which comprise at least one T cell epitope and are derived from protein allergens, in a non-immunogenic form, may cause unresponsiveness of appropriate T cell subpopulations such that they fail to respond or have a reduced response to the protein allergen and do not participate in stimulating an immune response upon such exposure.

While not intending to be limited to any theory, it is believed that T cell non-responsiveness (which includes reduced T cell responsiveness) is induced as a result of not providing an appropriate costimulatory signal sometimes referred to as a "second signal" Briefly, it is believed that stimulation of T cells requires two types of signals, the first is the recognition by the T cell via the T cell receptor of appropriate MHC-associated processed antigens on antigen presenting cells (APCs) and the second type of signal is referred to as a costimulatory signal(s) or "second signal" which may be provided by certain competent APCs. When a composition of the invention is administered without adjuvant, it is believed that competent APCs which are capable of producing the second signal or costimulatory signal are not engaged in the stimulation of appropriate T cells therefore resulting in T cell nonresponsiveness or reduced T cell responsiveness. In addition, there are a number of antibodies or other reagents capable of blocking the delivery of costimulatory signals such as the "second signal" which include, but are not limited to B7 (including B7-1, B7-2, and BB-1), CD28, CTLA4, CD40 CD40L CD54 and CD11a/18 (Jenkins and Johnson, *Current Opinion in Immunology,* 5:361-367 (1993), and Clark and Ledbetter, *Nature,* 367:425-428 (1994)) Thus, a peptide of the invention may be administered in nonimmunogenic form as discussed above, in conjunction with a reagent capable of blocking costimulatory signals such that the level of T cell nonresponsiveness is enhanced.

In addition, administration of the TRFP of the invention or fragment thereof which comprises at least one T cell epitope may modify the lymphokine secretion profile as compared with exposure to the naturally-occurring protein allergen or portion thereof (e.g. result in a decrease of IL-4 and/or an increase in IL-2). Furthermore, exposure to such protein allergen or fragment of such protein allergen may influence T cell subpopulations which normally participate in the response to the allergen such that these T cells are drawn away from the site(s) of normal exposure to the allergen (e.g., nasal mucosa, skin, and lung) towards the site(s) of therapeutic administration of the fragment or protein allergen. This redistribution of T cell subpopulations may ameliorate or reduce the ability of an individual's immune system to stimulate the usual immune response at the site of normal exposure to the allergen, resulting in a dimunution in allergic symptoms.

Peptides of varying sizes from within the structure of TRFP have been synthesized and purified by conventional techniques and examined for their ability to stimulate T cell lines and clones obtained from human cat allergic individuals. The methodologies used are described in Examples 5, 6 and 7.

Peptides from within the structure of TRFP have been shown to stimulate a proliferative response in TRFP primed T cell cultures. Indeed in certain cases (FIG. 8), the T cell proliferative response obtained with the peptides can substantially exceed that obtainable with TRFP or cat skin test allergen preparations. Such peptides comprise at least one T cell epitope of the TRFP protein.

It is also apparent (Tables 2 and 3) that certain areas of the TRFP sequence have weak T cell stimulatory activity (e.g., Fel 4-3, Fel 28-1); certain other areas have powerful activity (e.g., Fel 8-3, Fel 14). This range of activities may derive from purely primary sequence differences or from physicochemical differences induced by primary sequence changes. Key peptides from within the structure of TRFP which are highly reactive with T cells from cat allergic patients can be identified using the subject disclosure and known techniques (see Example 5 part B and FIG. 23).

Furthermore, it has been demonstrated that exposure of T cells in vitro to peptides comprising at least one T cell epitope can suppress a subsequent response to the allergen (TRFP) to a greater extent than that obtained with the allergen alone (Example 6, Table 4). This data points to the clear opportunity of selecting peptides identified by the current work and applying them in treatment paradigms in cat allergic patients designed to suppress their response to cat allergen exposure.

Peptides shown to have T cell stimulating activity and thus comprising at least one T cell epitope can be administered to an individual in the form of a therapeutic composition to reduce the individuals response to cat allergen. Such a therapeutic composition can comprise one or more of such peptides. A preferred composition comprises at least one peptide selected from the group consisting of peptide X (amino acid residues 7-30 from chain 1 of TRFP (SEQ. ID. NO: 17); also referred to as Fel 8-3 and shown in FIG. 17); peptide Y (amino acid residues 29-55 from chain 1 of TRFP (SEQ. ID. NO: 18); also referred to as Fel 30-4 and shown in FIG. 17); peptide Z (amino acid residues 14-39 frog chain 2 of TRFP (SEQ. ID. NO: 19); also referred to as Fel 31-2 and shown in FIG. 17); peptide A (amino acid residues 51-69 from chain 1 of TRFP (SEQ. ID. NO: 20) and shown in FIG. 17); peptide B (amino acid residues 74-92 from chain 2 of TRFP (SEQ. ID. NO: 21); also referred to as Fel 29 and shown in FIG. 17); peptide C (amino acid residues 51-66 from chain 1 of TRFP (SEQ. ID. NO: 22), also referred to as Fel 23 and shown in FIG. 17); and peptide D (amino acid residues 56-69 from chain 1 of TRFP (SEQ. ID. NO: 23); a modified form of Fel 21 and shown in FIG. 17), more preferably comprises at least one peptide selected from the group consisting of peptide X (SEQ. ID. NO: 17), peptide Y (SEQ. ID. NO: 18), peptide Z (SEQ. ID. NO: 19), peptide A (SEQ. ID. NO: 20) and peptide B (SEQ. ID. NO: 21) and most preferably comprises at least peptide X (SEQ. ID. NO: 17), or peptide Y (SEQ. ID. NO: 18) or peptide X (SEQ. ID. NO: 17) and peptide Y (SEQ ID NO:18). These therapeutic compositions can be administered in a therapeutically effective amount to an individual sensitive to *Felis domesticus* in order to reduce the allergic symptoms of the individual, i.e. treat the sensitivity. Additionally, two or more therapeutic compositions can be administered in a therapeutically effective amount to such individual to treat such sensitivity. These two or more therapeutic compositions can be administered simultaneously or sequentially.

As described in detail in Examples 8-15, T cell unresponsiveness has been induced in mice by subcutaneous or intravenous administration of peptide X or peptide Y separately or in combination.

The induction of T cell nonresponsiveness in mice was evidenced by decreases in peptide specific IL-2 production, IL-4 production, and antibody production. Decreases in the T cell activities that are expected to be associated with IgE production, T cell help for B cells and IL4 production have been shown. In addition, T cells specific for recombinant chain 1 of TRFP were tolerized by administering peptide X and peptide Y.

The invention further encompasses at least one therapeutic composition useful in treating allergy to cat which involves an immune response to TRFP comprising a sufficient percentage of the T-cell epitopes of the protein allergen such that in a substantial percentage of a population of individuals sensitive to the allergen, the response of such individuals to the allergen is substantially diminished, with the proviso that the therapeutic composition does not contain the entire protein antigen.

In addition, it has been shown in one experiment that exposure of T cells from cat allergic individuals to different epitope peptides from TRPF can produce distinctly different lymphokine secretion profiles (Example 7, Table 5). It is thus possible using the current invention to select for therapeutic application epitope peptides which drive a lymphokine secretion profile consistent with a therapeutically beneficial response upon treatment of cat allergic patients.

Administration of a TRFP protein or peptide of the present invention, such as isolated purified native TRFP free from all other polypeptides or contaminants, recombinant TRFP, modified TRFP, synthetically produced peptides of TRFP, alone or in combination, to an individual to be desensitized can be carried out using known techniques. The peptide or combination of two or more different peptides can be administered to an individual in a composition which also includes, for example, an appropriate buffer, a carrier and/or excipient. Such compositions will generally be administered by injection such as by subcutaneous injection, inhalation, transdermal application, intranasal application, oral application or rectal administration. For subcutaneous injection of peptides of the invention, it is preferred that such peptides be administered in soluble form.

The protein, peptide or antibodies of the present invention can also be used, in known methods, for detecting and diagnosing cat allergy. For example, blood obtained from an individual to be assessed for sensitivity to cat allergen is combined with an isolated peptide of TRFP or purified whole TRFP protein, under conditions appropriate for binding of components (e.g., antibodies, T cells, B cells) in the blood with the peptide. Subsequently, the extent to which such binding occurs is determined, using direct (e.g., ELISA assays) or indirect methods (e.g. determination of T cell activation).

It is also possible to modify epitopes of the TRFP, to combine epitopes, or to do both, for such purposes as enhancing therapeutic or preventive efficacy, stability (e.g., length of time for which they can be stored), and resistance to degradation in the body of TRFP peptides. Two or more TRFP epitopes can also be combined in order to enhance, for example, therapeutic effectiveness. For example, the amino acid sequences of two T cell epitopes present within the first 30 N-terminal amino acids can be produced and joined. Optionally, a linker may be used to join the T cell epitopes. The linker by which the epitopes are joined can be any non-epitope amino acid sequence or other appropriate linking or joining agent. The epitopes joined in this manner can be from the same chain of the TRFP or from different TRFP chains (e.g., one from chain 1 and one from chain 2). The resulting two-epitope construct can be used in treating cat-sensitive individuals. Alternatively, an epitope (or epitopes) present in the first chain of the TRFP and one (or more) present in the second chain can be joined to produce a construct which has greater therapeutic effectiveness than a single epitope peptide. Additionally, individual peptides can be physically mixed and administered as a therapeutant.

Through use of the protein and peptides of the invention, preparations of consistent, well-defined composition and biological activity can be made and administered for therapeutic purposes (e.g., to modify the allergic response of a cat allergen sensitive individual). Administration of such protein or peptides may, for example, modify B-cell response to TRFP, T-cell response to TRFP or both responses. Isolated peptides can also be used to study the mechanism of immunotherapy of cat allergy and to design modified derivatives or analogues useful in immunotherapy.

This invention enables the production of therapeutic treatments for cat allergic individuals which will possess similar or improved efficacy to that of current allergen immunotherapy without the adverse reactions normally associated with this form of therapy. Improved therapy could derive from use of purified and isolated TRFP or peptide expression products of the TRFP genes identified herein or appropriate modifications (mutations) thereof, or peptides derived from the structure of TRFP or modifications thereof.

For example, the purified isolated native TRFP or peptide can be modified using the polyethylene glycol method of A. Sehon and co-workers or in other ways which reduce the IgE reactivity of the native allergen and thereby decrease its adverse reaction potential.

Alternatively, the TRFP cDNAs defined herein, or portions thereof, can be expressed in appropriate systems to produce protein(s) or peptides with strong therapeutic activity, but greatly reduced ability to bind to IgE and thereby produce adverse reactions. To facilitate this, it is possible to add reporter group(s) to the chain 1 and/or 2 polypeptide backbone as an aid to efficient purification. One such reporter group is poly-histidine, which has been effectively used to purify recombinant proteins on immobilized metal ion affinity chromatography (Hochuli, E. et al., *Bio/Technology*, 6:1321-1325 (1988)). Specific cleavage sites can be introduced between the reporter group and the chain 1 and 2 polypeptide sequences, and cleavage at these sites can facilitate the isolation of TRFP chains or fragments free of irrelevant sequences. Another example of the modification of the TRFP chains 1 and 2 is the substitution of cysteine residues with another amino acid residue such as serine (or any other residue) to reduce disulfide complexes.

Site-directed mutagenesis of the TRFP cDNAs can also be used to modify the chain 1 and 2 structures. Such methods may involve PCR (Ho et al., *Gene* 77:51-59 (1989)) or total synthesis of mutated genes (Hostomsky, Z., et al., *Biochem. Biophys. Res. Comm.* 161:1056-1063 (1989)) since the two chains are each composed of coding sequences <400 bp. To enhance bacterial expression, the aforementioned methods can be used in conjunction with other procedures to change the mammalian codons in the constructs to ones preferentially used in *E. coli*.

Other modifications of the TRFP genes may include the construction of gene chimeras, where chains 1 and 2, or parts thereof, may be linked to form a single contiguous chain. For example, all or a portion of chain 1 may be linked with all or a portion of chain 2 cDNA and the resulting chimera may be produced as a recombinant hybrid (Horton et al., *Gene* 77:61-68 (1989)). It is also possible to construct multiple joined genes to promote stability of the expressed product or to enhance its therapeutic potential (Shen, et al., *Proc. Natl. Acad. Sci. USA* 81:4627-4631 (1984)).

Work by others has shown that high doses of allergens generally produce the best results (i.e., best symptom relief). However, many people are unable to tolerate large doses of allergens because of allergic reactions to the allergens. A peptide can be designed in such a manner to have the same or enhanced therapeutic properties as the corresponding naturally-occurring allergen but have reduced side effects (especially anaphylactic reactions) can be produced. These can be, for example, a peptide of the invention (e.g., one having all or a portion of the amino acid sequence of TRFP (SEQ. ID. NO: 1-2)) or a modified peptide, or peptide analogue.

Accordingly, the structure of a peptide of the invention can be modified for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose. For example, a peptide can be modified so that it maintains the ability to induce T cell unresponsiveness or reduced T cell responsiveness and bind MHC proteins without the ability to induce a strong proliferative response or possibly, any proliferative response when administered in immunogenic form.

Critical binding residues for the T cell receptor can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate or not affect T cell activity, but does not eliminate binding t the relevant MHC. In addition, those amino acid residues which are not essential for T cell receptor interaction can be modified by being replaced by another amino acid whose incorporation may enhance, diminish but not eliminate or not affect T cell activity but does not eliminate binding to relevant MHC. Many of the characteristics of peptides which bind to MHC Class II molecules are known. See e.g., Jorgensen, J. L. et al. (1992) *Annu. Rev. Immunol.* 10:835-873. For example, it is known that MHC Class II molecules preferably bind peptides having lengths of between eight to eleven amino acids, Ibid at 838, and contain amino acids at only about two or three positions which appear to influence binding to MHC molecules. In addition, peptide motifs shown to be involved in MHC Class II binding are taught by U.S. Pat. No. 5,019,384 to Gefter et al.

Additionally, many characteristics of the interaction between a T cell receptor and MHC molecules are known. For example, it is known that a core of five to seven critical amino acid residues are characteristic of most T cell determinants. Thus, peptides of the invention can be modified by replacing an amino acid shown to be essential to interact with the MHC protein complex with another, preferably similar amino acid residue (conservative substitution) whose presence is shown to enhance, diminish but not eliminate or not affect T cell activity. In addition; amino acid residues which are not essential for interaction with the MHC protein complex but which still bind the MHC protein complex can be modified by being replaced by another amino acid whose incorporation may enhance, not affect, or diminish but not eliminate T cell reactivity. Preferred amino acid substitutions for non-essential amino acids include, but are not limited to substitutions with alanine, glutamic acid, or a methyl amino acid.

In order to enhance stability and/or reactivity, peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention. Furthermore, peptides of the present invention can be modified using the polyethylene glycol (PEG) method of A. Sehon and coworkers (Wie et al. supra) to produce a protein or peptide conjugated with PEG. In addition, PEG can be added during chemical synthesis of a protein or peptide of the invention. Modifications of proteins or peptides or portions thereof can also include reduction/alyklation (Tarr in: *Methods of Protein Microcharacterization*, J. E. Silver ed. Humana Press, Clifton, N. J., pp 155-194 (1986)); acylation (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939,239; or mild formalin treatment (*Marsh International Archives of Allergy and Applied Immunology,* 41:199-215 (1971)).

To facilitate purification and potentially increase solubility of proteins or peptides of the invention, it is possible to add reporter group(s) to the peptide backbone. For example, polyhistidine can be added to a peptide to purify the peptide on immobilized metal ion affinity chromatography (Hochuli, E. et al., *Bio/Technology,* 6:1321-1325 (1988)). In addition, specific endoprotease cleavage sites can be introduced, if desired, between a reporter group and amino acid sequences of a peptide to facilitate isolation of peptides free of irrelevant sequences.

In order to successfully desensitize an individual to a peptide, it may be necessary to increase the solubility of a peptide for use in buffered aqueous solutions, such as pharmaceutically acceptable carriers or diluents, by adding functional groups to the peptide, terminal portions of the peptide, or by not including hydrophobic T cell epitopes or regions containing hydrophobic epitopes in the peptides or hydrophobic regions of the protein or peptide. For example, to increase solubility, charged amino acids or charged amino acid pairs or triplets may be added to the carboxy or amino terminus of the peptide. Examples of charged amino acids include, but are not limited to arginine (R), lysine (K), histidine (H), glutamic acid (E), and aspartic acid (D).

To potentially aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during recombinant construction of the peptide. The resulting peptide can be rendered sensitive to cathepsin and/or other trypsin-like enzymes cleavage to generate portions of the peptide containing one or more T cell epitopes.

Site-directed mutagenesis of DNA encoding a peptide or protein of the invention (e.g., TRFP or a fragment thereof) can be used to modify the structure of the peptide or protein by methods known in the art. Such methods may, among others, include PCR with degenerate oligonucleotides (Ho et al., *Gene,* 77:51-59 (1989)) or total synthesis of mutated genes (Hostomsky, Z. et al., *Biochem. Biophys, Res. Comm.,* 161: 1056-1063 (1989)). To enhance bacterial expression, the aforementioned methods can be used in conjunction with other procedures to change the eucaryotic codons in DNA constructs encoding protein or peptides of the invention to ones preferentially used in *E. coli*, yeast, mammalian cells, or other eukaryotic cells.

Using the structural information now available, it is possible to design TRFP peptides which, when administered to a cat allergen sensitive individual in sufficient quantities, will modify the individual's allergic response to cats. This can be done, for example, by examining the structure of TRFP, producing peptides (via a recombinant DNA expression system, chemical synthesis, chemical cleavage of the native allergen or otherwise) to be examined for their ability to influence B-cell and/or T-cell responses in cat allergen sensitive individuals and selecting appropriate peptides which contain epitopes recognized by the cells. In referring to an epitope, the epitope will be the basic element or smallest unit of recognition by a receptor, particularly immunoglobulins, histocompatibility antigens and T cell receptors where the epitope comprises amino acids essential to receptor recognition. Amino acid sequences which mimic those of the epitopes and which are capable of down regulating allergic response to TRFP can also be used.

It is now also possible to design an agent or a drug capable of blocking or inhibiting the ability of TRFP to induce an allergic reaction in cat sensitive individuals. Such agents could be designed, for example, in such a manner that they would bind to relevant anti-TRFP IgEs, thus preventing IgE-allergen binding and subsequent mast cell degranulation. Alternatively, such agents could bind to cellular components of the immune system, resulting in suppression or desensitization of the allergic response to cat allergens.

Peptides of the invention can also be used for detecting and diagnosing cat allergy. For example, this can be done by combining blood or blood products obtained from an individual to be assessed for sensitivity to cats with an isolated TRFP protein or peptide under conditions appropriate for binding of components in the blood (e.g., antibodies, T-cells, B-cells) with the protein or peptide(s) and determining the extent to which such binding occurs. Other diagnostic methods for allergic diseases which the protein or peptides of the invention can be used include radio-allergergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The presence in individuals of IgE specific for TRFP and the ability of T cells of the individual to respond to T cell epitope(s) of the protein allergen can be determined by administering to the individuals an Immediate Type Hypersensitivity test and a Delayed Type Hypersensivity test. The individuals are administered an Immediate Type Hypersensitivity test (see e.g. *Immunology* (1985) Roitt, I. M., Brostoff, J., Male, D. K. (eds), C. V. Mosby Co., Gower Medical Publishing, London, N.Y., pp. 19.2-19.18; pp. 22.1-22.10) utilizing purified native TRFP, a peptide of TRFP, or a modified form of the peptide, each of which binds IgE specific for the allergen. The same individuals are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would only be given to those individuals exhibiting a specific Immediate Type Hypersensitivity reaction. The Delayed Type Hypersensitivity test utilizes a modified form of TRFP or a portion thereof, TRFP produced by recombinant DNA techniques, or peptide derived from TRFP, each of which has the ability to stimulate human T cells and each of which does not bind IgE specific for the allergen in a substantial percentage of the population of individuals sensitive to the allergen (e.g., at least about 75%). After administration of the Delayed Type Hypersensitivity test, the extent to which a specific Delayed Type Hypersensitivity reaction occurs in the individual to the protein allergen or TRFP peptide indicating presence in the individual of T cells specific to T cell epitope(s) of the protein allergen or TRFP peptide is determined. Those individuals found to have both a specific Immediate Type Hypersensitivity reaction and a specific Delayed Type Hypersensitivity reaction are diagnosed as having sensitivity to a cat allergen and may, if need be, administered a therapeutically effective amount of a therapeutic composition comprising the modified form of TRFP or portion thereof, the TRFP produced by recombinant DNA techniques, or peptide, each as used in the Delayed Type Hypersensitivity test, and a pharmaceutically acceptable carrier or diluent.

It has been found that recombinant chain 1 of TRFP in a dimeric form has markedly reduced IgE binding, but maintains T cell reactivity (i.e., recombinant dimeric chain 1 contains peptides X and Y, both of which are known to contain at least one T cell epitope) and that mild alkali treated TRFP has markedly reduced IgE binding, but maintains T cell reactivity. Accordingly, recombinant chain 1 of TRFP in dimeric form or alkali treated TRFP can be used in the Delayed Type Hypersensitivity test described above, or in other diagnostic assays to determine sensitivity in an individual to T cell epitope(s) of TRFP and/or they can be used in therapeutic compositions to desensitize individuals to TRFP.

Peptides comprising at least two regions, each region comprising at least one T cell epitope of TRFP are also within the scope of the invention. Isolated peptides or regions of isolated peptides, each comprising at least two T cell epitopes of TRFP or use of more than one peptide having one T cell epitope of TRFP may be desirable for increased therapeutic effectiveness. Peptides which are immunologically related (e.g., by antibody or T cell cross-reactivity) to peptides of the present invention are also within the scope of the invention.

One aspect of this invention provides a method for selecting a peptide of TRFP suitable for pharmaceutical administration to an individual to treat cat allergy. To obtain isolated TRFP peptides, TRFP can be divided into non-overlapping peptides of desired length or overlapping peptides of desired lengths which can be produced by recombinant DNA techniques, or chemical synthesis or by chemical cleavage of the allergen. For example, a set of peptides having amino acid sequences which, when combined, encompass the entire amino acid sequence of TRFP can be produced. To determine peptides comprising at least one T cell epitope, isolated peptides are tested by, for example, T cell biology techniques, to determine whether the peptides elicit a T cell response or induce T cell non-responsiveness. Those peptides found to elicit a T cell response or induce T cell non-responsiveness are defined as having T cell stimulating activity. For use in pharmaceutical compositions, there are selected peptides comprising at least one T cell epitope, which peptides are capable of reducing T cell responsiveness or inducing T cell non-responsiveness.

Human T cell stimulating activity can be tested by culturing T cells obtained from a cat sensitive individual (i.e., an individual who has an IgE mediated immune response to a cat protein allergen) with a peptide derived from TRFP and determining whether proliferation of T cells occurs in response to the peptide as measured, e.g., by cellular uptake of tritiated thymidine. Stimulation indices for responses by T cells to peptides can be calculated as the maximum counts per minute (CPM) in response to a peptide divided by the control CPM. A stimulation index (S.I.) equal to or greater than two times the background level is considered "positive". Positive results are used to calculate the mean stimulation index for each peptide for the group of patients tested. For therapeutic purposes, preferred peptides of this invention comprise at least one T cell epitope and have a mean T cell stimulation index of greater than or equal to 2.0. A peptide having a mean T cell stimulation index of greater than or equal to 2.0 is considered useful as a therapeutic agent. Preferred peptides have a mean T cell stimulation index of at least 2.5, more preferably at least 3.5, more preferably at least 4.0, more preferably at least 5, even more preferably at least 7 and most preferably at least about 9. The experimental data described in the Examples was generated based on a preferred mean T cell stimulation index of at least 2.5.

For therapeutic purposes, preferred peptides are recognized by at least 10%, more preferably at least 20%, more preferably at least 30% and even more preferably at least 40% or more of individuals in a population of cat sensitive individuals. In addition, preferred TRFP peptides have a positivity index (P.I.) of at least about 100, more preferably at least about 250 and most preferably at least about 350. The positivity index for a peptide is determined by multiplying the mean T cell stimulation index by the percent of individuals, in a population of individuals sensitive to cat allergens (e.g., preferably at least 15 individuals more preferably at least 30 individuals or more), who have a T cell stimulation index to such peptide of at least 2.0. Thus, the positivity index represents both the strength of a T cell response to a peptide (S.I.) and the frequency of a T cell response to a peptide in a population of individuals sensitive to a cat allergen (see, for Example Table 2, infra).

In order to determine precise T cell epitopes by, for example, fine mapping techniques, a peptide having T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically.

For therapeutic purposes, peptides are selected based on various factors, including the strength of the T cell response to the peptide (e.g., stimulation index), the frequency of the T cell response to the peptide in a population of cat sensitive individuals, and the potential cross-reactivity of the peptide with other cat allergens. The physical and chemical properties of these selected peptides (e.g., solubility, stability) are examined to determine whether the peptides are suitable for use in therapeutic compositions or whether the peptides require modification as described herein.

To determine whether a peptide (candidate peptide) or a combination of candidate peptides are likely contain a sufficient percentage of T cell epitopes of TRFP to induce nonresponsiveness in a substantial percentage of a population of individuals sensitive to the protein antigen, an algorithm can be used. In accordance with one such algorithm, a human T cell stimulation index (discussed above) for the peptide(s) in an in vitro T cell proliferation assay is calculated for each individual tested in a population of individuals sensitive to TRFP. The remaining peptides in the in vitro T cell proliferation assay are overlapping peptides (overlapping by between about 5-10 amino acid residues) which cover the remainder of the protein not covered by the candidate peptide(s), which peptides are at least 12 amino acids long and which are preferably no longer than 30 and more preferably no longer than 25 amino acid residues in length. A human T cell stimulation index for each such remaining peptide in the set of peptides produced in the in vitro T-cell proliferation assay with T-cells obtained from each individual in the population of individuals tested is calculated and added together. For each individual, the human T cell stimulation index for the candidate peptide(s) is divided by the sum of the human T cell stimulation indices of the remaining peptides in the set of peptides tested to determine a percent. This percent is obtained for at least twenty (20) and preferably at least thirty (30) individuals sensitive to the protein antigen of interest and a mean percent is determined (the percentage of positive T cell responses (S.I. greater than or equal to 2.0) in response to the candidate peptide or combination of candidate peptides). A mean percent of about 10% or greater for the candidate peptide(s) together with a percent positive of at least about 60%, preferably about 75% and more preferably about 90%, or most preferably 100%, indicates that the candidate peptide(s) selected is likely to contain a sufficient percentage of T cell epitopes to induce T cell non responsiveness in a substantial percentage of a population of individuals sensitive to TRFP.

Additionally, for therapeutic purposes, preferred T cell epitope-containing peptides of the invention do not bind immunoglobulin E (IgE) or bind IgE to a substantially lesser extent (i.e., preferably at least 100-fold less or more preferably at least 1,000-fold less) than the protein allergen from which the peptide is derived binds IgE. The major complications of standard immunotherapy are IgE-mediated responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotactic factors). Thus, anaphylaxis in a substantial percentage of a population of individuals sensitive to TRFP could be avoided by the use in immunotherapy of a peptide or peptides which do not bind IgE in a substantial percentage (e.g., at least about 75%) of a population of individuals sensitive to TRFP, or if the peptide binds IgE, such binding does not result in the release of mediators from mast cells or basophils. The risk of anaphylaxis could be reduced by the use in immunotherapy of a peptide or peptides which have reduced IgE binding. Moreover, peptides which have minimal IgE stimulating activity are desirable for therapeutic effectiveness.

A preferred isolated peptide of the invention comprises at least one T cell epitope of TRFP and accordingly the peptide comprises at least approximately seven amino acid residues. For purposes of therapeutic effectiveness, therapeutic compositions of the invention may comprise peptides having at least two T cell epitopes of TRFP, and accordingly, the peptide comprises at least approximately eight amino acid residues and preferably at least twelve amino acid residues. Alternatively, the individual sensitive to TRFP may be administered more than one peptide of the invention comprising at least one T cell epitope. Additionally, therapeutic compositions comprising preferred isolated peptides of the invention preferably comprise a sufficient percentage of the T cell epitopes of the entire protein allergen such that a therapeutic regimen of administration of the composition to an individual sensitive to cats, results in T cells of the individual being rendered non-responsive to the protein allergen. Peptides of the invention produced by chemical synthesis comprising up to approximately forty-five amino acid residues in length, and most preferably up to approximately thirty amino acid residues in length are particularly desirable as increases in length may result in difficulty in peptide synthesis. Peptides of the invention may also be produced by recombinant DNA techniques as described above or by chemical cleavage of the native allergen.

Another embodiment of the invention provides peptides comprising at least two regions, each region comprising at least one T cell epitope of TRFP and accordingly each region comprises at least approximately seven amino acid residues.

These peptides comprising at least two regions can comprise as many amino acid residues as desired and preferably comprise 14 amino acid residues of TRFP, or if recombinantly produced preferably about 30 amino acid residues and most preferably at least about 40 amino acid residues of TRFP. If desired, the amino acid sequences of the regions can be produced and joined directly (or optionally by a linker) to increase sensitivity to processing by antigen-presenting cells. Such linker can be any non-epitope amino acid sequence or other appropriate linking or joining agent. To obtain preferred therapeutic peptides comprising at least two regions, each comprising at least one T cell epitope, the regions are arranged in a configuration different from a naturally-occurring configuration of the regions in TRFP, to reduce the possibility of IgE binding. For example, the regions containing T cell epitope(s) can be arranged in a noncontiguous configuration. Noncontiguous is defined as an arrangement of regions containing T cell epitope(s) which is different than that of an amino acid sequence present in TRFP from which the regions are derived. Furthermore, the noncontiguous regions containing T cell epitopes can be arranged in a non-sequential order (e.g., in an order different from the order of the amino acids of the native TRFP from which the region containing T cell epitope(s) are derived in which amino acids are arranged from an amino terminus to a carboxy terminus). A peptide comprising at least two ligands for use as a therapeutic can comprise at least about 15%, at least about 30%, at least about 50% or up to about 100% of the T cell epitopes of TRFP.

The individual peptide regions can be produced and tested to determine which regions bind immunoglobulin E specific for TRFP and which of such regions would cause the release of mediators (e.g., histamine) from mast cells or basophils. Those peptide regions found to bind immunoglobulin E and cause the release of mediators from mast cells or basophils in greater than approximately 10-15% of the allergic sera tested are preferably not included in the peptide regions arranged to form preferred peptides of the invention.

In the situation where the T cell epitopes of TRFP are unknown or ill-defined (e.g., some or all of the peptide regions of TRFP which have human T cell stimulating activity have not been defined by standard T cell biology techniques or the precise human T cell epitopes of TRFP have not been defined by fine mapping techniques), a peptide comprising two or more regions can be obtained by reviewing the known protein structure of TRFP and theoretically dividing the allergen into at least two peptide regions of desired lengths. For example, the protein sequence of TRFP can be systematically divided into at least two non-overlapping peptide regions of desired lengths, or at least two overlapping peptide regions of desired lengths and theoretically arranged to form at least one peptide in which the at least two regions are rearranged in a noncontiguous and preferably nonsequential order. This division into peptide regions can be arbitrary, can be made according to an algorithm, or can be wholly or partially based on regions of TRFP known to comprise at least one T cell epitope.

According to this method, peptides comprising two or more regions of TRFP can then be produced by recombinant DNA techniques or by chemical synthesis and the ability of the peptide to stimulate human T cells determined. The individual peptide regions can also be produced separately and tested to determine which regions bind immunoglobulin E specific for TRFP and which of such regions would cause the release of mediators (e.g. histamine) from mast cells or basophils.

Particularly preferred peptides comprising two or more regions of T cell reactivity of TRFP for use in treating sensitivity to Felis domesticus are selected from peptides X (SEQ. ID. NO: 17), Y (SEQ. ID. NO: 18), Z (SEQ. ID. NO: 19), A (SEQ. ID. NO: 20), B (SEQ. ID. NO: 21) and C (SEQ. ID. NO: 22), and modifications thereof. Preferred peptides comprise peptide YZX and peptide A YZXB. Throughout this application, the letters X, Y, Z, A, B, and C refer respectively to peptide X, peptide Y, peptide Z, peptide A, peptide B, and peptide C. When the letters are used together (e.g., YZX), a peptide comprising peptide Y, peptide Z and peptide X linked by peptide bonds from amino to carboxy terminus in the sequential order specified is meant (i.e., YZX refers to a peptide comprising the amino acid sequence of peptide Y linked, without any intervening amino acid residues, to the amino acid sequence of peptide Z linked, without any intervening amino acid residues, to the amino acid sequence of peptide X). The peptides of the invention, e.g., YZX, can comprise additional amino acid residues at either the amino or carboxy terminus of the peptide. Preferably, additional amino acid residues which may be added to either the amino or carboxy terminus of the peptide do not exceed 30 amino acid residues and more preferably, do not exceed 5 amino acid residues. Amino acids which may be added to either the carboxy or amino terminus of the peptide include charged amino acids, i.e. arginine (R), lysine (K), histidine (H), glutamic acid (E) or aspartic acid (D), or amino acids with reactive side chains, i.g., cysteine (C), asparagine (N), or glutamine (Q), or amino acids with sterically small side chains, e.g., alanine (A) or glycine (G).

As described in the Examples which follow, chains 1 and 2 of the human. T cell Reactive Feline Protein (TRFP) (FIGS. 1 and 2) have been recombinantly expressed in E. coli and purified. T cell epitope studies using overlapping peptide regions derived from the TRFP amino acid sequence were used to identify multiple T cell epitopes in each chain of TRFP. As also described in the Examples, DNA constructs were assembled in which three regions (designated peptide X, peptide Y and peptide Z), each containing at least one major human T cell epitope of TRFP were linked in six possible combinations to produce six DNA constructs encoding peptides comprising the three regions in six different configurations. Since peptide X shares 5 amino acids at its carboxy terminus with 5 amino acids at the amino terminus of peptide Y, peptides XYZ and ZXY could have been constructed with or without duplication of the 5 amino acids. In the following Examples, the peptides were assembled contiguously, without duplication of the 5 amino acid sequence. In addition to the three regions X, Y and Z, other regions; each containing at least one human T cell epitope, could also be included in the peptides and DNA constructs having four or more regions (of N! configurations, where N=the number of regions) produced. Alternatively, one or more regions can be substituted for peptide X, peptide Y, or peptide Z, such as peptide A, B or C, to produce for example peptide AXY.

Another aspect of this invention pertains to a multipeptide formulation suitable for pharmaceutical administration to cat sensitive individuals. The multipeptide formulation includes at least two or more peptides of TRFP having human T cell stimulating activity in an in vitro T cell proliferation assay (i.e., comprising at least one T cell epitope). Special considerations when preparing a multipeptide formulation include maintaining the solubility and stability of all peptides in the formulation at a physiologically acceptable pH. This requires choosing one or more pharmaceutically acceptable carriers such as excipients which are compatible with all the peptides in the multipeptide formulation. For example, suitable excipients include sterile water, sodium phosphate, mannitol or both sodium phosphate and mannitol or any combination thereof. Additionally due to the potential for dimerization of the peptides in a multipeptide formulation, there may also be included an agent such as EDTA to prevent dimerization. Alternatively, any material or procedures known in the art to prevent dimerization may be used. A preferred multipeptide formulation includes at least one first peptide and at least one second peptide of TRFP each having human T cell stimulating activity and soluble at a physiologically acceptable pH and selected from the group of peptides X (SEQ. ID. NO: 17), Y (SEQ. ID. NO: 18), Z (SEQ. ID. NO: 19), A (SEQ. ID. NO: 20), B (SEQ. ID. NO: 21) and C (SEQ. ID. NO: 22), and modifications thereof. In a preferred embodiment, the multipeptide formulation includes Peptide X (SEQ. ID. NO: 17), Peptide Y (SEQ. ID. NO: 18) and modifications thereof, and sodium phosphate and mannitol. In this embodiment, it is preferred that Peptide X (SEQ. ID. NO: 17) and Peptide Y (SEQ. ID. NO: 18) are in the form of a lyophilized powder which is reconstituted in a physiologically acceptable carrier, such as sterile water, prior to use. As an illustrative example, a multipeptide formulation comprising two active peptides, peptide X and peptide Y was produced and used in Phase II human clinical trials. Peptide X and Peptide Y were combined during manufacturing to produce a vial containing a sterile, pyrogen free, lyophilized powder having the following composition:

| | |
|---|---|
| Active: | 0.75 mg peptide X and 0.75 mg peptide Y or |
| Inactives: | 0.05 M Sodium Phosphate pH 5.7 |
| | 5% w/v Mannitol, U.S.P. |
| Diluent: | Sterile Water for Injection, U.S.P. (initial reconstitution) |
| | 0.9% Sodium Chloride for Injection |
| | (dilution beyond initial reconstitution) |

Preparation of this Multipeptide Formulation Required Reconstitution of the Vials with sterile water for injection. In another embodiment, the multipeptide formulation further includes at least one third peptide of TRFP, such as Peptide A (SEQ. ID. NO: 20) or Peptide C (SEQ. ID. NO: 22), having human T cell stimulating activity and soluble at a physiologically acceptable pH. The multipeptide formulation of the invention can be provided in the form of a kit, including instructions for use.

DNA to be used in any embodiment of this invention can be cDNA obtained as described herein or, alternatively, can be any oligodeoxynucleotide sequence that codes for all or a portion of the amino acid sequence represented in FIGS. 1-7, 17 and 18, or the functional equivalent thereof. Such oligodeoxynucleotide sequences can be produced chemically or mechanically, using known techniques. A functional equivalent of an oligonucleotide sequence is one that is capable of hybridizing to a complementary oligonucleotide sequence to which the sequence (or corresponding sequence portions) of FIGS. 1-7, 17 and 18, hybridizes and/or that encodes a product (e.g., a polypeptide or peptide) having the same functional characteristics of the product encoded by the sequence (or corresponding sequence portion) of FIGS. 1-7, 17 and 18. Whether a functional equivalent must meet one or both criteria will depend on its use (e.g., if it is to be used only as an oligoprobe, it need meet only the first criterion and if it is to be used to produce an allergen, it need meet only the second criterion).

The structural information that is available or can be deduced from the amino acid sequences of FIGS. 1-7, 17 and 18 (e.g., DNA, protein/peptide sequences), can also be used to identify or define T cell epitope peptides and/or B cell epitope peptides which are of importance in cat allergic reactions and to elucidate the mediators or mechanisms (e.g., interleukin-2, interleukin-4, gamma interferon) by which these reactions occur. This knowledge should make it possible to design peptide-based cat allergen therapeutic agents or drugs which can be used to modulate these responses.

Another aspect of the invention pertains to an antibody specifically reactive with TRFP, or a fragment thereof. The antibodies of this invention can be used to standardize allergen extracts or to isolate the naturally-occurring or native form of TRFP. For example, by using proteins or fragments thereof based on the cDNA sequence of TRFP, anti-protein/anti-peptide antisera or monoclonal antibodies can be made using standard methods. A mammal such as a mouse, a hamster or rabbit can be immunized with an immunogenic form of such protein or an antigenic fragment which is capable of eliciting an antibody response. Techniques for conferring immunogenicity on a protein or peptide include conjugation to carriers or other techniques well known in the art. TRFP or fragment thereof can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-TRFP antisera can be obtained and, if desired, polyclonal anti-TRFP antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, (*Nature* (1975) 256:495-497) as well as other techniques such as the human B cell hybridoma technique (Kozbar et al., *Immunology Today* (1983) 4:72) and the EBV-hybridoma technique to produce human monoclonal antibodies (Cole et al., *Monoclonal Antibodies and Cancer Therapy* (1985) Alan R. Liss, Inc. pp. 77-96). Hybridoma cells can be screened immunochemically for production of antibodies specifically reactive with TRFP and the monoclonal antibodies isolated.

The term antibody as used herein is intended to include fragments thereof which are also specifically reactive with TRFP. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-TRFP portion.

Another aspect of this invention provides T cell clones and soluble T cell receptors specifically reactive with TRFP or a fragment thereof. Monoclonal T cell populations (i.e., T cells genetically identical to one another and expressing identical T cell receptors) can be derived from an individual sensitive to TRFP, followed by repetitive in vitro stimulation with TRFP or portion thereof in the presence of MHC-matched antigen-presenting cells. Single TRFP MHC responsive cells can then be cloned by limiting dilution and permanent lines expanded and maintained by periodic in vitro restimulation. Alternatively, TRFP specific T-T hybridomas can be produced by a technique similar to B cell hybridoma production. For example, a mammal, such as a mouse can be immunized with TRFP or fragment thereof, T cells from the mammal can be purified and fused with an autonomously growing T cell tumor line. From the resulting hybridomas, cells responding to TRFP or fragment thereof are selected and cloned. Procedures for propagating monoclonal T cell populations are described in *Cellular and Molecular Immunology* (Abul K. Abbas et al. ed.), W. B. Saunders Company, Philadelphia, Pa. (1991) page 139. Soluble T cell receptors specifically reactive with TRFP or fragment thereof can be obtained by immunoprecipitation using an antibody against the T cell receptor as described in *Immunology: A Synthesis* (Second Edition), Edward S. Golub et al., ed., Sinauer Associates, Inc., Sunderland, Mass. (1991) pages 366-269.

T cell clones specifically reactive with TRFP or fragment thereof can be used to isolate and molecularly clone the gene encoding the relevant T cell receptor. In addition, a soluble T cell receptor specifically reactive with TRFP or fragment thereof can be used to interfere with or inhibit antigen-dependent activation of the relevant T cell subpopulation, for example, by administration to an individual sensitive to a cat allergen. Antibodies specifically reactive with such a T cell receptor can be produced according to the techniques described herein. Such antibodies can be used to block or interfere with the T cell interaction with peptides presented by MHC.

The present invention will now be further illustrated by the following Examples, which are not intended to be limiting in any way. The contents of all references, patents and published patent applications cited throughout this application are hereby incorporated by reference.

EXAMPLE 1

Isolation and Protein Sequence Analysis of the T Cell Reactive Feline Protein (TRFP)

Monoclonal Affinity Purification of a T Cell Reactive Feline Protein From House Dust Extract A house dust sample collected from several homes with cats was used to isolate and purify TRFP. Monoclonal antibodies 1G9 or 6F9 (obtained from M.D. Chapman) were coupled to Sepharose 4B and used for the purification according to a published protocol. Chapman, M. D., et al., *J. Immunology*, 140(3):812-818, (1988). The purified TRFP was decolorized by loading it on a Phenyl-Sepharose column (Pharmacia) with 4N NaCl, then eluted with 2M and 1M NaCl. Decolorized TRFP was recovered by dialyzing the 2M and 1M salt eluates against distilled water and lyophilized. Decolorization was also carried out by passing the house dust extract through a Sephacryl 200 column (Pharmacia) before the affinity purification.

Preparation of TRFP Peptides

Affinity purified TRFP was first reduced with dithiothreitol and then alkylated with 4-vinyl pyridine. After desalting with a Sephadex G10 column, the reduced and alkylated TRFP was cleaved chemically with cyanogen bromide (CNBr) or enzymatically with one of the following enzymes: endoproteinase Glu-C (Boehringer Mannheim), endoproteinase Asp-N (Boehringer Mannhein), endoproteinase Lys-C (Boehringer Mannhein). The affinity purified TRFP was also digested by trypsin (Worthington) without reduction and alkylation. The digestion products were separated on an Aquaport RP300 column (C8) with acetonitrile gradient in 0.1% trifluoroacetic acid (TFA). The individual peaks were subjected to the protein sequencer.

Peptide and Protein Sequence Analysis

An Applied Biosystems Model 477A gas phase sequencer with on-line phenylthiohydantoin (PTH) amino acid analysis (Model 120A) was used. A modification of extraction program, multiple butylchloride extractions, was used to improve the amino acid recovery. O-phthalaldehyde was used in blocking of primary amines when proline was located at the amino terminus. Brauer, A. W., et al., *Anal. Biochemistry*, 137:134-142, (1984). In situ alkylation was performed by using the non-nucleophilic reductant, tributylphosphine with concomitant alkylation by 4-vinyl pyridine in ethylmorpholine buffer. Andrews, P. C. and Dixon, J. E., *Anal. Biochemistry*, 161:524-528 (1987). The N-terminal protein sequence analysis of the intact TRFP protein revealed that there is one major amino acid sequence and several minor amino acid sequences. The major sequence (chain 1 in FIG. 6) corresponds to the published Fel d I N-terminal 33 amino acid residues with two significant differences. Chapman, M. D., et al., *J. Immunology*, 140(3):812-818, (1988). The most prevalent minor sequence (at 55% the level of the major sequence) was designated as chain 2 (FIG. 7). The other minor sequences were various N-terminal truncated forms of chain 2. Since the 4th residue of chain 1 and the 7th residue of chain 2 were proline, o-phthaladehyde was applied before the 4th cycle or the 7th cycle of Edman degradation to block out chain 2 or chain 1 sequences, respectively. The protein sequence information of chain 1 (68 N-terminal amino acid residues) and chain 2 (58 N-terminal amino acid residues) was further enhanced by an additional OPA blocking before cycle 32 and cycle 37 for chain 1 and chain 2, respectively. The protein sequences were confirmed and expanded by sequence analysis of enzymic and chemical digested peptides. Time dependent in situ CNBr digestion of TRFP on the sequencer glass filter disk could provide additional protein sequence information. Simpson, R. J. and Nice, E. C., *Biochem. International*, 8:787-791 (1984). Prior to the in situ CNBr digestion, five sequencer cycles were performed and then the protein sample was treated with acetic anhydride to block all amino groups. These steps removed the N-terminal five residues from both chains and blocked the amino groups of the next residue from both chains and any other peptide in the sample. After 5 hours of in situ CNBr digestion, one major peptide sequence, CB-1, and three minor peptides which had 60% (CB-2), 38% (CB-3), and 12% (CB-4) signal levels of the major peptide sequence were identified. CB-1 started from residue 43 of chain 2 and extended the N-terminal sequence of chain 2 to 68 residues. CB-2 was identical to a purified CNBr peptide sequence of chain 2 (75-80). CB-3 corresponded to the peptide sequence 65-68 of short form chain 2. CB-4 corresponded to the peptide sequence 50-66 of chain 1. A tryptic peptide TRYP-1 (short form chain 2, 58-80) connected the 68 residue N-terminal peptide with an endopeptidase Asp-N generated peptide, D-10 (chain 2, 72-83), and extended the chain 2 to 83 amino acid residues. An endopeptidase Lys-C generated peptide, K13 (chain 1, 64-70), extended chain 1 to 70 amino acid residues. Other enzymic and CNBr generated peptides confirmed the N-terminal sequences of chain 1 and chain 2. The sequences of a short tryptic peptide, TRYP-2 (long form chain 2, 58-69), and an endopeptidase Asp-N peptide, D-10, revealed that there was sequence polymorphism in chain 2 residues 65 to 72. In summary, the primary amino acid sequence of TRFP chains 1 and 2 derived by protein sequencing methods is presented in FIGS. 6 and 7.

There is a potential N-glycosylation site present in the cDNA deduced amino acid sequence, $Asn_{33}$-$Ala_{34}$-$Thr_{35}$. The protein sequence analysis identifies the $Ala_{34}$ and $Thr_{35}$ of chain 2; however, nothing can be identified at the position 33. It suggests that post-translation modification occurs at $Asn_{35}$ of chain 2 and the modification is stable to the trifluor acetic acid treatment during protein sequencing. The hypothesis was confirmed by treating TRFP with N-peptidase F (Boehringer Mannheim) which reduced the size of chain 2 to 7-12 kD in SDS-PAGE/Western immunoblot. Moreover, both chains can be modified by β-elimination which implies they may have O-linked glycosylation. The two chains are covalently linked together (approximately 20 kD) through disulfide bond(s).

EXAMPLE 2

Cloning of cDNAs Encoding Chains 1 and 2 of the Human T cell Reactive Feline Protein (TRFP)

MOPAC (and derived methods) have been used to isolate both partial and full-length cDNAs encoding the TRFP chains 1 and 2. The PCR methods used are described in detail below.

Cloning of TRFP Chain 1 cDNAs

First strand cDNA synthesis was performed with 1 μg of poly A plus RNA isolated from a pooled sample of cat parotid and mandibular glands using oligo dT primer.

MOPAC PCR amplification (Lee et al. *Science* 239:1288-1291 (1988)) of an internal portion of chain 1 was carried out using a sense/antisense pair of degenerate oligonucleotide primers encoding amino acids 1-6 and 50-54 of chain 1, respectively (see below). These oligonuclotides (primers 1 and 2) were used with a Perkin Elmer/Cetus PCR kit to amplify an aliquot of the above cDNA using the following cycles:

| | |
|---|---|
| 94° C. 1 min | (denaturation) |
| 45° C. 1 min. 30 sec. | (annealing) |
| 72° C. 1 min. | (polymerization) 5 Cycles |
| 94° C. 1 min | (denaturation) |
| 55° C. 1 min. 30 sec. | (annealing) |
| 72° C. 1 min. | (polymerization) 20 Cycles |

One tenth of the above PCR reaction was fractionated on a 3% NuSieve Agarose gel. A DNA band of the predicted size (172 base pairs) was observed. This gel was then "Southern" blotted onto GeneScreen Plus nylon membrane under denaturing conditions and hybridized to $^{32}$p end-labeled chain 1 specific oligonucleotide probe (Fel 1) in 6×SSC at 35° C., and washed in 2×SSC at 48° C. The 173 base pair band hybridized to the chain 1 specific probe.

The remainder of the PCR reaction was restriction digested with Cla I and Xho I and fractionated over a preparative 3% NuSieve agarose gel and the 173 base pair band excised. The fragment was ligated into Cla I/Xho I digested Bluescript plasmid (Stratagene), and subjected to Sanger/dideoxy DNA sequence analysis using a Sequenase kit (US Biochemicals). The data from this analysis shown in FIG. 1 demonstrated that the sequence of the PCR amplified DNA fragment, when translated, is in agreement with an internal portion of the protein sequence of chain 1 of TRFP.

The 3' end of the chain 1 cDNA encoding TRFP was cloned according to the RACE PCR method. Frohman, M. A., Dush, M. K., and Martin, G. R. *Science* 85: 8998-9002 (1988).

First strand cDNA synthesis was performed with 1 μg of poly A plus RNA isolated from a pooled sample of cat parotid and mandibular glands using the EDT primer with Superscript reverse transcriptase.

RACE PCR amplification of the carboxy terminal portion of chain 1 was carried out using primer 3 and the ED primer as the 5' and 3' specific primers, respectively. Primers were used with a Perkin Elmer/Cetus PCR kit to amplify an aliquot of the above cDNA using the following cycle:

| | |
|---|---|
| 94° C. 1 min. | (Denaturation) |
| 55° C. 1 min. 30 sec. | (Annealing) |
| 72° C. 1 min. | (Polymerization) 30 Cycles |

One tenth of the above PCR reaction was fractionated on a 2% agarose gel. After "Southern" blotting of the gel onto GeneScreen Plus nylon membrane and hybridization to a chain 1 specific oligonucleotide probe (Fel 1), as above, no bands that could be candidates for cDNAs encoding the 3' portion of the TRFP Chain 1 were detected.

A second PCR reaction with cycling identical to that used for the first amplification was performed with a $^1$/$_{100}$th aliquot of the initial PCR reaction products as template and primer 4 (encoding amino acids just 3' of those encoded in primer 3) and the ED oligonucleotide as primers. This "nested" PCR reaction served to specifically reamplify products from the primary PCR reaction derived from TRFP chain 1 cDNA.

One tenth of this second PCR reaction was fractionated on a 2% agarose gel. After "Southern" blotting of the gel onto GeneScreen Plus nylon and hybridization to a chain 1 specific oligonucleotide probe, as above, a DNA band about 350 base pairs in length was detected.

The remainder of the second PCR reaction was restriction digested with Cla I and Xba I, and fractionated over a preparative 1% SeaPlaque agarose gel and the 350 base pair band excised. The fragment was ligated into Cla I/Xba I digested Bluescript plasmid (Stratagene), and subjected to Sanger/dideoxy DNA sequence analysis using a Sequenase Kit (US Biochemicals). The data from this analysis shown in FIG. 1 demonstrates the sequence of PCR amplified 350 base pair DNA fragment, when translated, is in agreement with the protein sequence at the carboxy terminus of chain 1 of TRFP. The DNA sequence analysis also reveals a stop codon adjacent to the cysteine codon at position 72, indicating the protein sequence analysis of chain 1 of TRFP had been done in its entirety. In addition, 3' untranslated DNA sequence of the 350 base pair fragment contains a prototypical polyadenylation signal characteristic of the 3' end of a cDNA.

Primers and Probes

```
primer 1 (SEQ. ID. NO:33)
              T  A  A
5'- TATCGATGAAATTTG C CC T GC T GT- 3'
    Cla I primer 2 (SEQ. ID. NO:34)
             G  T  T  A
5'- GCTCGAG A TC C TC C TC T GTCAT- 3'
    Xho I primer 3 (SEQ. ID. NO:35)
5'- GGAATTCATCGATGTGAAGAGGGATCTATTC- 3'
    EcoRI Cla I primer 4 (SEQ. ID. NO:36)
5'- GGATCGATGAATTCTATTCCTGACGGGAACCC- 3'
    Cla I EcoR I EDT primer (SEQ. ID. NO:37)
5'- GGAATTCTCTAGACTGCAGGT 15 - 3'
    EcoR I Xba I Pst I
```

-continued

```
ED primer (SEQ. ID. NO:38)
5'- GGAATTCTCTAGACTGCAGGT- 3'
      EcoRI Xba I Pst I Fel 1 probe (SEQ. ID. NO:39)
              G
       T  GT  A   G   G
5' - GA_CGA_ATA_CGT_TGA_ACA_AGT- 3'
              C
```

Cloning of TRFP chain 2 cDNAs

First strand cDNA was synthesized with a commercial kit using oligo (dT) priming of mRNA prepared from a pool of the parotid/mandibular glands of five cats. An internal sequence of chain 2 was determined using MOPAC.

Two redundant oligomers were synthesized based on protein sequence of human T cell reactive feline protein Chain 2:

```
                        C
                        G
                G       GA   CT
5' CGGAATTCAA_AATGGCIGA_AAC_TTG_TCC
   (Oligomer #56 (SEQ. ID. NO:40)),
``` which corresponds to coding strand sequence encoding amino acids 2-8 (KMAETCP) and

```
                G  GT      T  T
5'CGGGCTGCAGTA_ACA_ATC_CTGIAT_CTT_CTTCAT
   (Oligomer #57 (SEQ. ID. NO:41)),
``` which corresponds to non-coding strand sequence complementary to amino acids 42-48 (MKKIQDCY; (SEQ. ID. NO: 42)). Oligomer 56 had an Eco RI restriction site added (underlined) and oligomer 57 had a Pst I restriction site added (underlined) for cloning purposes. Inosine (I) was used once in each oligomer to reduce the redundancy of the final oligomers as described in Knoth, et al. *Nucl. Acids Res.* 16:10932. (1988). PCR was performed using 100 pmol of each primer plus first strand cDNA using the following conditions for amplification:

Denature at 94° C. for 1 minute; primer anneal at 45° C. for 1.5 minutes; elongate at 72° C. for 2 minutes; repeat cycle 4 times.

Denature as above; anneal at 55° C. for 1.5 minutes; elongate as above; repeat second cycle 19 times (total of 25 cycles).

Two cDNA clones containing Chain 2 sequence were identified. Both clones had identical sequence. The prototype clone is F2.m.

The carboxy terminus of the chain 2 cDNA encoding TRFP was cloned according to the RACE PCR method. First strand cDNA was synthesized from mRNA as described above.

Oligomers used in amplification of chain 2 were:

Oligomer #59 (SEQ. ID. NO: 43) 5' GGATCGATGAAT-TCGGTGGCCAATGGAAATG, which corresponds to coding strand sequence encoding amino acids 19-23 (VANGN) of chain 2 and contained Cla I and Eco RI restriction sites for cloning purposes.

Oligomer #61 (SEQ. ID. NO: 44) 5' ATTACTGTTGGACT-TGTCCCT, which corresponds to amino acids 23-28 (LLLDLS; (SEQ. ID. NO: 45)) of Chain 2, and ED/EDT primers described above.

Two PCR reactions were carried out using "nested primers." The primary PCR reaction used 100 pmol of oligomer 59 and 100 pmol of the ED and EDT primers in a 3:1 ratio. Amplification conditions were the same as those used in obtaining internal Chain 2 sequence. 0.01 volume of the primer PCR was reamplified using 100 pmol of oligo #61 (a "nested" primer) and 100 pmol of the ED primer using the standard conditions.

The amplified fragment was cloned and sequenced to give the carboxy terminus of Chain 2. There are two prototype clones: F15.a and F15.d. F15.a matched one protein sequence of the dominant protein sequence for Chain 2 while F15.d matched a second protein sequence. F15.a has been called the "Long" sequence and F15.d has been called the "Short" sequence. There are 7 clustered amino acid differences between F15.a and F15.d including 5 amino acid changes and two amino acid deletions in F15.d relative to F15.a (see FIGS. 6 and 7).

Chain 2 has been isolated from the mRNA from two cat skins as well as from mRNA from pooled salivary glands. The skin samples were sampled separately. Skin A (one of the five cats used in making the salivary gland pool) had mRNA encoding only the short form of Chain 2. Skin B (from a sixth cat not part of the five used in making the salivary gland pool) contained mRNA for both the Short and Long forms of Chain 2 in a 3:1 (S:L) ratio. A third form of Chain 2 has been found in the skin. This is called "ST" for Short Truncated (FIG. 5). ST has 16 contiguous amino acid differences from the short form and has deleted the last 10 amino acids of the Short sequence. Examples of this clone have been found in mRNA from both Skin A and Skin B. Chain 2 Long is the dominant form of Chain 2 in the salivary glands (23/24 clones). Chain 2 short is the dominant form of chain 2 in the skin (20/25 clones from two cats), while the Long form (0/13 clones in Skin A and 3/12 clones in Skin B) and the ST form (2/25 clones from two cats) appear to be minor forms. A summation of the complete nucleotide sequence of TRFP chains 1 and 2 derived by the methods cited above is presented in FIGS. 1-5.

Polymorphism in the long form of chain 2 was detected in the skin mRNA from one cat. This polymorphism involved the substitution of a Leucine for Isoleucine at amino acid 55 and a Threonine for a Methionine at position 74.

Cloning the $NH_2$ Terminals of TRFP Chain 1 and Chain 2

First and second strand cDNA was synthesized with a commercial kit using oligo dT priming of mRNA prepared from a pool of the parotid/mandibular glands of five cats. The double-stranded cDNA was blunted and then blunt-end ligated to annealed oligomers #68 and #69 (see below). These oligomers, described in Rafnar, et. al., *J. Biol. Chem.*, (1991) 266:1229-1236 were designed to utilize the "Anchored PCR" as described by Frohman, et. al. (1988) *Proc. Natl. Acad. Sci. USA* 85:8998-9002 and modified by Roux and Dhanarajan (1990) *BioTech.* 8:48-57. These oligonucleotides are not entirely homologous and, thus, will not self-prime. The oligomers will blunt end to every cDNA.

Oligomer #68 (SEQ. ID. NO: 46). Template, Blunt Anchor

5' GGGTCTAGAGGTACCGTCCGATCGATCATT

Oligomer #69 (SEQ. ID. NO: 47). Linker, Blunt Anchor

5' p-AATGATCGATGCT

Oligomer #64 (SEQ. ID. NO: 48). Anchor Primer (AP) was

5' GGGTCTAGAGGTACCGTCCG

33

Cloning the NH₂ Terminal of T RFP Chain 2

Two oligomers based on internal chain 2 nucleotide sequence were synthesized:

Oligomer #60 (SEQ. ID. NO: 49). 5' CGGG<u>CTCGAG</u>CTGCAGCTGTTCTCTCTGGTTCAGT, which corresponds to non-coding strand sequence complementary to that encoding amino acids 35-40 (TEPERT; (SEQ. ID. NO: 50)), and Oligomer #70 (SEQ. ID. NO: 51). 5' GGG<u>CTGCAG</u>ATTCTAGTCAGCCTGATTGA, which corresponds to non-coding strand sequence of the 3' UT region. Both oligomers matched the antisense strand sequence and contained Pst I and Xho I restriction sites (underlined, Oligomer 60) or Pst I (underlined, Oligomer 70) for cloning purposes.

Two PCR reactions were carried out using "nested primers." Amplification conditions were the same as those used for MOPAC. The 1° amplification reaction was done with oligomers #64 (AP) and #70. 0.01 volume of the 1° PCR product was reamplified with oligomers #64 and #60 (which is "nested," i.e. internal, relative to oligo—. #70). Amplified material was recovered, cloned and sequenced.

Cloning the NH₂ Terminal of TRFP Chain 1

One oligomer based on internal chain 1 sequence was synthesized:

Oligomer #66 (SEQ. ID. NO: 52), 5' GGGCTCGAGCTGCAGTTCTTCAGTATTCTGGCA, corresponds to non-coding strand sequence complementary to that encoding amino acids 38-43 (ARILKN; (SEQ. ID. NO: 53)) of chain 1. The restriction sites Pst I and Xho I were added for cloning purposes.

Two PCR reactions were carried out using "nested primers." Amplification conditions were the same as those used for MOPAC. 1° PCR was performed with primer 2 (described above) and #64 (AP). 0.01 vol of the 1° PCR product was reamplified with oligomers #64 and #66 (which is "nested," i.e., internal, relative to primer 2). Amplified material was recovered from the 2° PCR, cloned and sequenced. Two different 5' sequences were obtained and designated Leaders A and B (FIGS. 1 and 2).

Chain 1 with Leader A is a dominant sequence in both salivary gland and skin mRNA. It was not possible to detect chain 1 with Leader B sequence in the mRNA preparation from Skin A. Chain 1 with Leader B sequence was a minor component of the mRNA in both the pooled salivary gland and Skin B preparations.

EXAMPLE 3

Screening of a Cat Genomic DNA Library to Identify Clones Containing DNA Encoding the TRFP An EMBL4 cat genomic library, using cat liver DNA as starting material, was constructed using recommended procedures described in Frischauf, A.-M. et al. *J. Mol. Biol.* 170:827-842 (1983). The EMBL4 cat genomic library was screened using ³²P-radiolabelled chain 1 and chain 2 cDNA as probes. The library was plated out and screened, yielding individual genomic clones that hybridized to either chain 1 or chain 2 cDNA probes, but not to both. This hybridization pattern verified that the chain 1 and chain 2 cDNAs are products of different genes. Northern blot analysis of the cat salivary gland RNA probed with 32P-radiolabelled TRFP chain 1 or 2 cDNA also demonstrated the presence of the two separate mRNAs. The DNA sequence of the genomic clones

34

(designated CTGch1 and CTGch2) was determined and confirmed the hybridization results.

Individual full length PCR generated chain 1 clones (Example 2) were shown to have two different sequences at their 5' end (see FIGS. 1 and 2). One interpretation is that chain 1 has two alternative leader sequences. The DNA sequence of the chain 1 genomic clone (CTGch1) has confirmed this interpretation and demonstrated that the single chain 1 gene possesses both alternative sequences closely-linked at the 5' end of the structural gene.

The DNA sequence of the chain 2 genomic clone (CTGch2) demonstrated the presence in the cat genome of different gene segments encoding the long and short forms of chain 2 (see FIGS. 3 and 4). The isolation of two genes encoding the TRFP chain 2 is consistent with the tissue specific expression of the two different mRNA forms in cat skin and salivary gland (FIGS. 3, 4 and 7; see Example 2).

Of note is that comparison of the genomic sequences to that of isolated cDNAs demonstrated that the TRFP has sequence microheterogeneity.

EXAMPLE 4

Expression of Recombinant TRFP Chains 1 and 2 cDNA clones encoding all or parts of TRFP chain 1 or chain 2 have been subcloned into *E. coli* expression vectors, specifically pSEM-1, -2 and -3 (Knapp, S. Broker, M. and E. Amann. *BioTechniques* 8: 280-281. (1990). These vectors carry a truncated form of the *E. coli* lac Z gene (lacZ'), encoding the N-terminal 375 amino acids of Beta-galactosidase (Beta-gal). cDNA clones encoding chain 1 and chain 2 of TRFP were altered using PCR methods such that the 5' end possessed an inframe poly-histidine sequence followed by an asp-pro acid-sensitive bond. Cultures containing the chain 1 or 2 expression constructs produce substantial quantities of recombinant fusion protein products upon IPTG induction. The presence of the poly-histidine reporter group has allowed the recombinants to be highly purified using immobilized metal-ion affinity chromatography (Houchuli, E., et al., *Biotechnology*, 6: 1321-1325 (1988)). Mild-acid cleavage of the Asp-Pro site leads to the release of intact full-length TRFP chain 1 or chain 2 protein. Standard protein purification methods lead to substantial quantities of recombinant protein free of irrelevant sequences. Protein sequence analysis of the purified peptide have verified the authenticity of the sequence. Rabbit anti-peptide antisera directed against either chain 1 sequence (Fel 1, (SEQ. ID. NO: 54) EITPAVKRDVDLFLTGT; Fel 2, (SEQ. ID. NO: 55) DVDLFLTGTPDEYVEQV; Fel 4, (SEQ. ID. NO: 56) NARILKNCVDAKMTEEDKE), or chain 2 sequences (Fel 18, (SEQ. ID. NO: 57) LLLDLSLTKVNATEPERTAMKKIQDC), have been generated. The anti-peptide antisera react with the recombinant proteins (described above) on Western blots.

Recombinant chain 1 and chain 2 peptides, and fragments or modifications thereof, can be used as desensitizing therapeutants.

EXAMPLE 5

T Cell Studies with Purified T Cell Reactive Protein

Synthesis of Peptides:

Synthetic peptides derived from the TRFP sequence were synthesized using standard Fmoc/tBoc synthetic chemistry and purified by reverse phase HPLC. Tables 2 and 3 indicate the peptides used in these studies. Other peptides referred to in the following Examples are shown in FIGS. 17 and 18. The peptide names are consistent throughout.

Part A:

T Cell Responses to TRFP and Synthetic Peptides

Peripheral blood mononuclear cells (PBMC) were purified from 60 ml of heparinized blood from cat allergic patients. PBMC were subsequently treated as described below, although in individual cases, the length of time of cultivation with IL-2 and/or IL-4 and the specific peptides used for stimulation varied.

10 ml of PBMC from patient 131 at $10^6$/ml were cultured at 37° C. for 7 days in the presence of 5 µg purified TRFP/ml RPMI-1640 supplemented with 5% pooled human AB serum. Viable cells were purified by Ficoll-Hypaque centrifugation and cultured for three weeks at 5 units recombinant human IL-2/ml and 5 units recombinant human IL-4/ml. The resting T cells were then restimulated (secondary) with 5 µg TRFP at $2\times10^5$/ml in the presence of irradiated (3500 Rads) autologous PBMC at a concentration of $5\times10^5$/ml for three days, purified by Ficoll-Hypaque centrifugation and grown in 5 units IL-2 and 5 units IL-4/ml for two weeks. For assay, $2\times10^4$ resting secondary T cells were restimulated (tertiary) in the presence of $5\times10^4$ irradiated (3500 Rads) autologous PBMC or $2\times10^4$ transformed B cells (20,000 Rads) with various concentrations of allergens or their fragments in a volume of 200 microliters in a 96-well round bottom assay plates for 3 days. Each well then received 1 µCurie tritiated (methyl) thymidine for 16 hours. The counts incorporated were collected onto glass fiber filters and processed for liquid scintillation counting.

Antigens used: T cell reactive feline protein (TRFP), Hollister-Stier cat epithelium skin test reagent (CST), IPC ragweed pollen extract (pollen), and synthetic peptides derived from TRFP protein sequence (See FIGS. 6 and 7). Positive T cell proliferation is for these experiments was considered to be greater than 2.5 times the media control (T cells and antigen presenting cells alone).

Alternatively, PBMC were treated as follows: The primary stimulated cells were cultured in IL-2/IL-4 for two weeks. The resting T cells derived from this culture were tested in a secondary assay with some, but not all, of the above allergens. The results of these assessments are shown in Tables 2 and 3. FIG. 8 demonstrates that T cells from patient 131 respond to T cell epitopes present in the Fel 1, 5 and 8 peptides. This type of epitope analysis has allowed the definition of T cell epitopes present in TRFP. Using a larger panel of patients, we have demonstrated the dominant epitopes in a heterogeneous population by deriving a positivity index (PI). The PI is derived from the average stimulation index of the responding population multiplied by the percentage of individuals that demonstrate a positive response to that peptide. This analysis is shown in Table 2 and 3.

This data demonstrates that while most of the TRFP protein contains T cell epitopes capable of stimulating T cells from some individuals, there are major differences in the strength of the elicited T cell response obtained with different portions of the TRFP molecule. The data has shown that each epitope works in some individuals and that each individual has a characteristic response pattern

TABLE 2

Response of Cat Allergic Patients to Chain #1 TRFP Peptides

| Peptide | Amino acid | PI[1] | SI[2] | N[3] |
|---|---|---|---|---|
| Fel 1[4] | 1-17, 3T | 392 | 5.6 | 121 |
| 1-2 | 1-17 | 311 | 7.4 | 83 |
| 1-3 | 1-17 | 422 | 6.2 | 26 |
| 1-4 | 6-17 | 816 | 9.6 | 32 |
| 1-5 | 8-17 | 286 | 5.2 | 25 |
| 1-6 | 10-17 | 312 | 5.2 | 26 |
| Fel 2 | 9-25 | 416 | 7.3 | 30 |
| Fel 3[6] | 18-33, 31P, 32D | 674 | 9.5 | 123 |
| 3-1 | 18-33 | 638 | 9.4 | 40 |
| 3-10 | 18-31 | 504 | 6.9 | 28 |
| 3-11 | 18-30 | 863 | 10.4 | 12 |
| 3-15 | 18-29 | 1040 | 10.4 | 13 |
| 3-13 | 18-28 | 690 | 11.5 | 14 |
| 3-14 | 18-27 | 260 | 6.2 | 10 |
| Fel 8 | 1-30 | 1393 | 18.1 | 86 |
| 8-1 | 5-33 | 1374 | 15.1 | 47 |
| 8-2 | 6-33 | 1353 | 15.2 | 47 |
| 8-3 | 7-33 | 1437 | 16.9 | 47 |
| Fel 14 | 18-43 | 1054 | 13.7 | 125 |
| 14-1 | 23-36 | 871 | 9.9 | 88 |
| 14-3 | 25-36 | 621 | 6.9 | 90 |
| 14-4 | 26-36 | 474 | 6.0 | 79 |
| 14-5 | 27-36 | 286 | 5.4 | 53 |
| 14-2 | 29-42 | 336 | 4.6 | 60 |
| Fel 4 | 37-55 | 601 | 7.7 | 120 |
| 4-1 | 37-52 | 822 | 9.9 | 20 |
| 4-2 | 37-49 | 378 | 6.2 | 15 |
| 4-3 | 37-46 | 185 | 3.7 | 13 |
| Fel 30-1 | 25-49 | 268 | 5.6 | 23 |
| 30-2 | 25-48 | 248 | 4.2 | 22 |
| 30-3 | 25-47 | 230 | 4.8 | 23 |
| 30-4 | 29-55 | 1079 | 11.6 | 44 |
| 30-5 | 29-54 | 792 | 11.0 | 43 |
| 30-6 | 29-53 | 415 | 6.2 | 43 |
| 30-7 | 26-55 | 339 | 5.3 | 14 |
| 30-8 | 28-55 | 262 | 4.1 | 14 |
| Fel 15 | 44-60 | 440 | 11.0 | 60 |
| Fel 23 | 51-66 | 343 | 6.6 | 63 |
| Fel 21[5] | 56-70, 70R | 360 | 5.8 | 66 |

[1] PI: Average SI of all responding patients tested multiplied by the percent of those patients with a positive response.
[2] SI: Average of the cpm of T cell and antigen presenting cell proliferation to the antigen divided by cpm of T cells and antigen presenting cells alone from responding patients. An SI of >2.5 is considered positive.
[3] N: Number of patients tested.
[4] Amino acid 3 changed to T.
[5] Amino acid 70 changed to R.
[6] Amino acids 31 and 32 changed to P and D, respectively.

TABLE 3

Response of Cat Allergic Patients to Chain #2 TRFP peptide

| Peptide | Amino acid | PI | SI | N |
|---|---|---|---|---|
| Fel 16 | 1-22 | 283 | 5.9 | 52 |
| Fel 17 | 12-33 | 421 | 6.1 | 114 |
| Fel 32-1 | 12-24 | 442 | 6.6 | 21 |
| 32-2 | 14-24 | 424 | 5.3 | 20 |
| 32-3 | 16-24 | 270 | 3.7 | 22 |
| Fel 18 | 23-48 | 466 | 6.3 | 99 |
| Fel 33-1 | 26-36 | 340 | 5.4 | 63 |
| 33-2 | 26-38 | 210 | 4.2 | 50 |
| 33-3 | 26-40 | 235 | 5.0 | 47 |
| Fel 31-1 | 14-40 | 733 | 9.4 | 36 |
| 31-2 | 14-39 | 599 | 8.1 | 35 |
| 31-3 | 14-38 | 598 | 8.3 | 36 |
| 31-4 | 14-37 | 622 | 8.4 | 35 |
| 31-5 | 14-36 | 539 | 7.6 | 37 |
| 31-6 | 15-40 | 295 | 4.4 | 33 |
| 31-7 | 15-36 | 267 | 5.8 | 33 |
| Fel 20-1 | 34-59 | 395 | 5.9 | 79 |

TABLE 3-continued

Response of Cat Allergic Patients to Chain #2 TRFP peptide

| Peptide | Amino acid | PI | SI | N |
|---|---|---|---|---|
| Fel 25 | 49-68 | 350 | 7.6 | 56 |
| Fel 28 | 60-82 | 94 | 3.6 | 43 |
| Fel 28-1[1] | 60-82 | 176 | 5.5 | 44 |
| Fel 29 | 74-92 | 259 | 5.5 | 47 |

[1]Based on short form chain 2 sequence (C2S)

Part B:

T Cell Proliferation Assay with Purified TRFP and Various Peptides Conducted Using T cells from a Panel of 42 Cat Allergic Patients.

Peripheral blood mononuclear cells (PBMC) were purified from 60 ml of heparinized blood from 42 allergic patients. PBMC were subsequently treated as described below, although in individual cases, the length of time of cultivation with IL-2 and/or IL-4 and the specific peptides used for stimulation varied.

5 ml of PBMC from patients at $2 \times 10^6$/ml were cultured at 37° C. for 6 days in the presence of 10 µg purified TRFP/ml RPMI-1640 supplemented with 5% pooled human AB serum. Viable cells were purified by Ficoll-Hypaque centrifugation and cultured for two to three weeks at 5 units recombinant human IL-2/ml and 5 units recombinant human IL-4/ml. For assay, $2 \times 10^4$ resting secondary T cells were restimulated (secondary) in the presence of $5 \times 10^4$ irradiated (3500 Rads) autologous PBMC or $2 \times 10^4$ transformed B cells (20,000 Rads) with various concentrations of allergens or their fragments in a volume of 200 microliters in a 96-well round bottom assay plates for 3 days. Each well then received 1 µCurie tritiated (methyl) thymidine for 16 hours. The counts incorporated were collected onto glass fiber filters and processed for liquid scintillation counting.

Antigens used: T cell reactive feline protein (TRFP), and synthetic peptides derived from TRFP protein sequence (See FIGS. 6 and 7). Positive T cell proliferation for these experiments was considered to be greater than 2.0 times the media control (T to cells and antigen presenting cells alone).

This data demonstrates that while most of the peptides tested are capable of stimulating T cells from some individuals, T cells from this population of 42 cat allergic patients respond most strongly to peptides X and Y as indicated by their comparatively high S.I.s and Positivity Index (P.I.).

EXAMPLE 6

Induction of T Cell Non-Responsiveness by a TRFP T Cell Epitope Containing Peptide Exposure of peptide specific T cells to their specific peptide can induce T cell non-responsiveness to the protein containing the T cell epitopes (Jenkins, M. K., and Schwartz, R. H. *J. Exp. Med.* 165:302-319 (1987)). While not intending to be limited to any theory it is possible that any strong T cell epitope can be used to induce unresponsiveness or tolerance to the whole allergen. This would result in the inability of the individual to respond to a natural allergen exposure. The individual would not respond by the stimulation of helper T cells. The lack of helper T cells would result in an altered lymphokine response and/or the absence of an IgE response and, consequently, a reduced allergic response to cat allergens.

Patient 155 TRFP secondary primed T cells ($2.5 \times 10^6$) were rested and cultured with ($2.5 \times 10^6$) irradiated autologous Epstein Barr Virus transformed B cells (EBV) in 1 ml of complete RPMI with 10% AB serum in 12×75 mm polypropylene snap cap tubes and increasing amounts of antigen over 5 consecutive days. The T cell cultures were exposed to 5 µg/ml purified native TRFP on day 0 and 5 µg/ml, 10 µg/ml, 10 µg/ml and 20 µg/ml thereafter. The peptide treated cultures were exposed to 1 µg/ml peptide on day 0 and 1 µg/ml, 1 µg/ml, 2 µg/ml and 5 µg/ml thereafter. In addition, 0.5 ml of fresh media was replaced on day 2. The cells were then washed and set up for a proliferation assay with $2 \times 10^4$ T cells and $2 \times 10^4$ irradiated (2500 Rad) autologous EBV and various doses of antigen. T cell proliferation was measured as incorporation of tritiated thymidine at day 9. The induction of in vitro unresponsiveness or tolerance is demonstrated in Table 4. This experiment demonstrates the ability of TRFP and peptides thereof to induce anergy or tolerance in antigen specific T cell lines.

TABLE 4

Antigen Response of a TRFP-primed T cell culture exposed to a Fel 8-3 or TRFP

| Tolerance treatment: | T cell proliferation (cmp) following Antigenic challenge: | | | |
|---|---|---|---|---|
| | — | TRFP | Fel 8-3 | Ragweed Peptide |
| — | 1,530 | 58,890 | 58,150 | 2,130 |
| Fel 8-3 | 1,270 | 12,320 | 3,850 | 5,130 |
| TRFP | 2,190 | 33,160 | 36,030 | 6,670 |
| Ragweed Pep. | 920 | 64,050 | 45,020 | 3,590 |

EXAMPLE 7

Cytokine Profiles of T Cells Responsive to TRFP or Synthetic Peptides from the TRFP Protein Sequence Peripheral blood mononuclear cells (PBMC) were purified from cat-allergic patients as described in Example 5. Five× $10^6$ PBMC were cultured at $2 \times 10^6$/ml for 36 hours in the presence of medium only, 20 µg purified TRFP/ml or 50 µg peptide/ml. The cells were then washed two times with phosphate buffered saline (PBS, pH 7.2) and lysed with 2 ml 0.4 M guanidinium isothiocyanate, 0.5% Sarkosyl, 5 mM sodium citrate, 0.1 M 2-mercaptoethanol, pH 7.0. The lysate was then forced through a 26 gauge needle to shear genomic DNA, and was layered onto a 2 ml cushion of 5.7 M CsCl, 0.01 M EDTA, pH 7.5 in diethylpyrocarbonate (DEPC)-treated water. The lysate was centrifuged at 35,000 RPM in a Beckman SW41 rotor for 18 hours at 20° C. The RNA pellet was resuspended in 0.4 ml TE (10 mM Tris, 1 mM EDTA), pH 7.5, 0.1% SDS, and then extracted three times with 0.5 ml phenol/ 0.2 ml chloroform. The RNA was then precipitated on dry ice with 2.5 volumes ice-cold ethanol, 1/10 volume 3 M sodium acetate, pH 5.2 in DEPC-treated water, rinsed once with 70% ethanol in DEPC-treated water, and dried. The RNA pellet was resuspended in 2 µl TE., pH 7.5 in DEPC-treated water.

Total cellular RNA was converted to cDNA using the Superscript kit (BRL, Bethesda, Md.). Two µl of RNA were added to one µl oligo (dT)12-18 (500 µg/ml) and 9 µl water. The sample was heated to 70° C. for 10 minutes and ice quenched. Four µl 5× buffer were added to the sample along with 2 µl 0.1 M DTT and 1 µl dNTP mix (10 mM each, dATP, dCTP, dGTP, dTTP). One µl reverse transcriptase (200U) was added and the reaction was carried out for one hour at 42° C. The reaction was terminated by incubation of the sample at 90° C. for five minutes and stored at −80° C.

Ten-fold serial dilutions of T cell cDNA in 10 mM TRIS, pH 7.5 were amplified using the standard kit and protocol recommended by Perkin Elmer-Cetus (Redwood City, Calif.). Each sample received 26.65 µl water, 5 µl ×PCR buffer, 8 µl of dNTP mix (1.25 mM each of dATP, dCTP, dGTP and dTTP), 0.1 µl alpha 32P-dCTP (3000 Ci/mmol), 0.25 µl AmpliTaq, 5 µl cDNA and 5 µl cytokine-specific 5' and 3' primers (20 micromolar). The primers used for most cytokines and the beta-actin control were purchased from Clontech (Redwood City, Calif.). The human IL-4 primers were purchased from Research Genetics (Huntsville, Ala.) and had the following sequences: 5' hIL-4 primer (SEQ. ID. NO: 58):

5'-GTC-CAC-GGA-CAC-AAG-TGC-GAT-ATC-ACC-3'
3' hIL-4 primer (SEQ. ID. NO: 59):
5'-GTT-GGC-TTC-CTT-CAC-AGG-ACA-GGA-ATT-C-3'

The reactions were carried out after overlaying each sample with one drop of mineral oil, with the following program in a programmable thermal cycler (MJ Research, Cambridge, Mass.)

| Step | Temperature | Time |
| --- | --- | --- |
| 1 | 94° C. | 1 min |
| 2 | 60° C. | 1 min |
| 3 | 72° C. | 2 min |
| 4 | cycle to step 1 | 29 times |
| 5 | 72° C. | 7 min |
| 6 | 4° C. | hold |

The PCR products were extracted once with 25 µl chloroform and 25 µl of each sample were then electrophoresed on an 8% polyacrylamide gel at 250 V. The gel was dried and exposed to pre-flashed x-ray film. Several exposures of each gel were then scanned using a Shimadzu flying spot laser densitometer. Values on the linear portion of the titrations were then compared to the medium control values to obtain a stimulation index for each sample. Primers for beta-actin were included as a control for general cDNA levels in each sample. Where the medium control values are not detectable, the lowest measurable response was set at 1.00. In other experiments, levels of cytokine cDNA can be compared directly with previously amplified cytokine specific cDNAs as standards. Thus, absolute levels of particular cytokine cDNAs can be compared from one sample to another and from one experiment to another. Results of one experiment are shown in Table 5. In this experiment, IL-2, IL-4 and IFN-gamma levels were measured. As shown, in this particular cat-allergic patient, peptides such as Fel 18 generate more IL-4 than certain other TRFP-derived peptides (Fel 14 and Fel 17). This analysis will be expanded to studies of other cytokines involved in the generation of allergic responses, such as IL-5, IL-8, IL-9, TGF-beta. Samples of cDNA from each treatment can also be saved for later analysis once additional cytokines are identified and sequenced. Peptides generating a spectrum of cytokines favorable for the generation of allergic responses can be avoided for therapeutic use in the treatment of cat allergy. Similarly, TRFP-derived peptides that are shown to generate cytokines which dampen the allergic response, such as IFN-gamma and IL-10, can be selected for treatment of cat allergy.

In another set of experiments, following a different methodology, T-cell proliferation, IL-2 production and IL-4 production for four cat allergic patients was studied. These experiments examined the ability of peptides comprising epitopes of TRFP to induce in vitro proliferation of T cells from cat allergic patients and whether this proliferation can be linked to the synthesis of the cytokines, interleukin 2 (IL-2) and interleukin 4 (IL-4).

In addition the peptides shown in Tables 2 and 3, peptides Fel-32 (SEQ. ID. NO: 60), Fel-33 (SEQ. ID. NO: 24), Fel-34 (SEQ. ID. NO: 25), Fel-35 (SEQ. ID. NO: 26), Fel-36 (SEQ. ID. NO: 27), Fel-37 (SEQ. ID. NO: 28), Fel-38 (SEQ. ID. NO: 29), Fel-38-1 (SEQ. ID. NO: 30), Fel-39 (SEQ. ID. NO: 31), and Fel-39-1 (SEQ. ID. NO: 32) as shown in FIG. 18 were included in these experiments.

Human T cell lines from four cat allergic patients (patients 688, 730, 738, and 807) were isolated. Heparinized peripheral blood specimens were obtained from cat allergic patients and the mononuclear cell fraction was purified by Ficoll-Hypaque centrifugation. An aliquot of these cells ($2 \times 10^6$) was stimulated in vitro with purified native TRFP (10 µg/ml) and grown in the presence of recombinant IL-2 and IL-4. The T cell line was then rested in culture until ready for secondary proliferation assay.

Two$\times 10^4$ cells were cultured in 200 µl medium containing various concentrations of test antigens with $5 \times 10^4$ γ-irradiated autologous Epstein-Barr Virus transformed cells as antigen presenting cells. After 3 days of culture, each microwell was pulsed overnight with 1 µCurie tritiated thymidine, and the amount of radioactivity incorporated was measured by liquid scintillation counting. The stimulation index (S.I.) for each antigen was then calculated. The S.I. is defined as the maximal counts/min for each antigenic stimulation divided by the medium control counts/min.

Two$\times 10^6$ rested T cells were cultured in 1 ml of medium containing 20 mg/ml of test antigen with $2 \times 10^6$ γ-irradiated autologous Epstein-Barr Virus transformed cells as antigen presenting cells. Identical controls received no antigen. After a 20 hour incubation, cells were separated from medium by centrifugation. The IL-2 in the medium was measured by proliferation of the IL-2 dependent T cell line, CTLL-3. Cultures of $1 \times 10^4$ CTLL-3 were exposed to three dilutions (25%, 5%, 1%) of sample supernatants, incubated for 20 hours, and harvested after 4 hour pulse with 1 µCurie tritiated thymidine. The IL-2 bioassay is sensitive to 2 pg/ml L-2. IL-4 was measured by an ELISA purchased from R&D Systems, Minneapolis, Minn. The IL-4 ELISA is sensitive to 16 pg/ml IL-4. The stimulation indices for IL-2 and IL-4 production were calculated by dividing the amount of IL-2 or IL-4 contained in the medium from stimulated T cells divided by the amount of IL-2 or IL04 released by non-stimulated T cells.

The data from the experiments with individual patients 688, 730, 738, and 807 is not shown. The data from the combined panel of the four patients is shown in FIGS. 21A-C and FIG. 22. The results indicates that T-cells from cat allergic individuals respond to various peptides derived from the TRFP molecule. The stimulation index (S.I.) profile for T cell proliferation is similar to both the IL-2 production profile, and the IL-4 production profile for each of the patients (i.e., the same peptides shown to induce T cell proliferation were found to induce IL-2 and IL-4 production.) These results show that T-cell proliferation, IL-2 and IL-4 production are suitable methods for defining peptides which have T cell stimulating activity.

Furthermore, none of the epitopes stimulate IL-4 to the exclusion of IL-2. There do not appear to be peptides comprising epitopes which stimulate only IL-4, which is the cytokine responsible for IgE synthesis and subsequent allergic symptoms. However, one peptide, Fel 4, induces more IL-4 than IL-2 in this panel of four patients. The data from the individual patients and shown for the combined panel of patients in FIGS. 21A-C and 22 also show that interleukin production favors IL-4 as opposed to IL-2 when T cell lines from cat allergic individuals were cultured by TRFP.

TABLE 5

IL-2, IFN-γ and IL-4 Measurements by PCR
Patient 409 primary 36 hour culture

| Treatment | STIMULATION INDEX | | | RATIO | |
|---|---|---|---|---|---|
| | IL-2 | IFN-γ | IL-4 | IL-2/IL-4 | IFN/IL-4 |
| Medium | — | 1.0 | 1.0 | | |
| TRFP | — | 2.1 | 3.8 | | 0.9 |
| Fel 8 | 1.0 | 1.8 | 0.3 | 3.3 | 6.0 |
| Fel 14 | 106.9 | 75.0 | 1.9 | 56.3 | 39.5 |
| Fel 4 | — | 25.8 | 10.0 | | 2.6 |
| Fel 21 | 23.9 | 41.6 | 3.2 | 7.5 | 13.0 |
| Fel 17 | 315.1 | 82.4 | 7.5 | 42.0 | 11.0 |
| Fel 18 | 4.6 | 5.6 | 12.0 | 0.4 | 0.5 |
| Fel 20-1 | — | 12.0 | 4.6 | | 2.6 |
| Fel 25 | 2.9 | 12.7 | 2.5 | 1.2 | 5.1 |
| Fel 28 | — | 3.8 | 0.5 | | 7.6 |
| Fel 29 | 1.2 | 3.0 | 1.1 | 1.1 | 2.7 |

EXAMPLE 8

Subcutaneous and Intravenous Administration of Peptide Y Induces T Cell Non-responsiveness in Mice Four groups of five BDF1 (C57BL/6J×DBA/2J) mice (females, 6-8 weeks of age), were injected either subcutaneously in a single dorsal site between the forelimbs or intravenously through one of the tail veins. For each injection site on day 0 and day 5, one group of animals was injected with 300 μg peptide Y in Phosphate Buffered Saline (PBS) and the other was injected with PBS alone. On day 10, each animal was challenged with 100 μg peptide Y in 200 ml Complete Freuds adjuvant (CFA) in four sites, two subcutaneous sites at the base of the tail and two subcutaneous sites on the thigh. The animals were sacrificed by cervical dislocation on day 20 and inguinal and popliteal nodes were removed and placed in rinsing buffer, cold RPMI 1640 containing 1% Fetal Bovine Serum (FBS). The nodes were rinsed with rinsing buffer and forced through a fine stainless steel mesh, using a glass pestal to suspend them in rinsing buffer. The suspended cells were rinsed two times by centrifugation at 1500 rpm for 10 minutes and resuspended with rinsing buffer. An aliquot of suspended cells from each animal was counted on a Coulter Counter Model ZB.

The cells ($4\times10^6$/ml) were incubated in culture media (RPMI media containing 10% FBS, 2 mM L-glutamine, 50 U/ml penicillin, 50 μg/ml streptomycin, and $5\times10^{-5}$ M 2-mercaptoethanol) and with either 150 μg/ml peptide Y (FIG. 10) or alone. The 0.2 ml cultures were done in triplicate in flat bottom 96 well plates (Costar) at 37° C. and 5% $CO_2$. After 24 hours, 50 ml of the media from each well was placed in separate round bottom 96 well plates (Costar) and was frozen overnight at −20° C. to eliminate carryover of live cells. The supernatants were tested after thawing for their ability to support the growth of CTLL-2, an IL-2 dependent T cell clone (ATCC TIB#214). CTLL-2 in log phase growth were rinsed 2 times by centrifugation at 1000 rpm for 10 minutes, aspiration of the media, and resuspension of the pellet with culture media. CTLL were added to the warmed culture supernatants ($5\times10^3$ CTLL cells/well) and the IL-2 assay was incubated at 37° C. and 5% $CO_2$. After 24 hours, 1 μCi/ml $^3$H-thymidine was added in 50 μl/well and the CTLL cells were incubated an additional 4-6 hours, then they were harvested with a Tom-Tec 96-well cell harvester. The $^3$H-incorporation in each well was counted by a Betaplate Model 1205 scintillation counter. Background counts were not subtracted.

Figure 9:
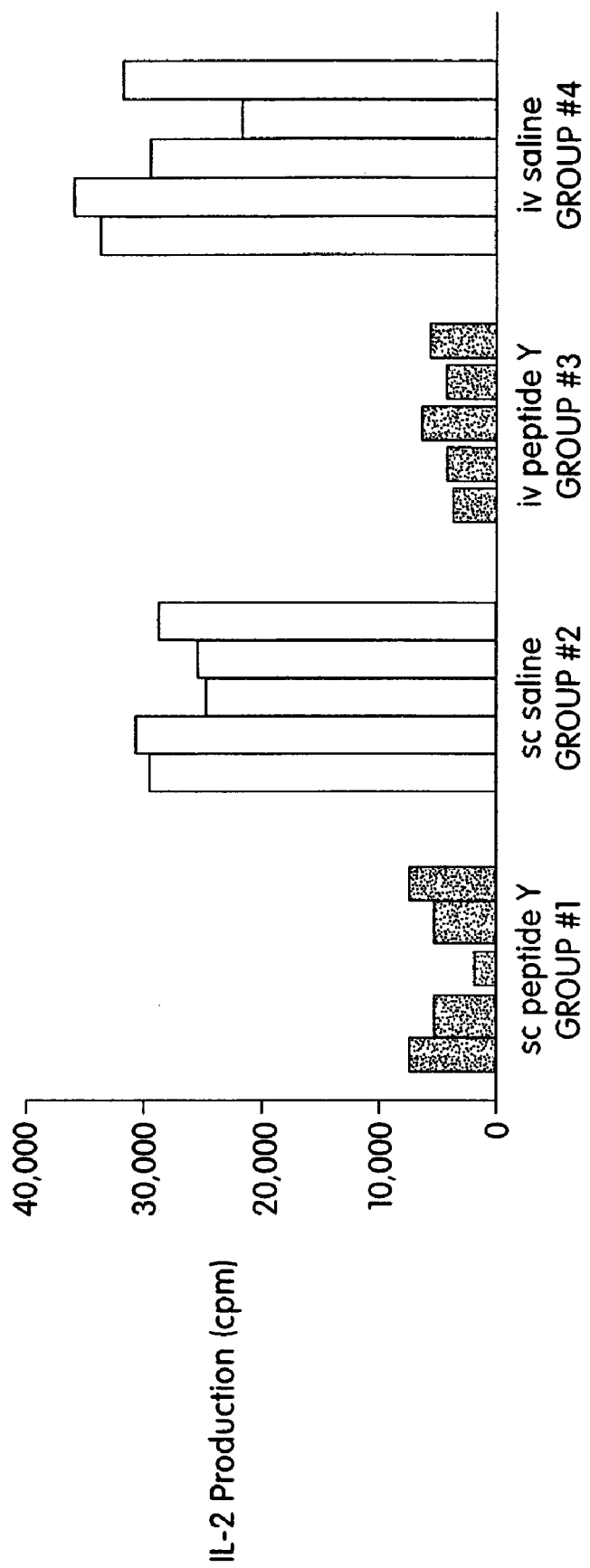
FIG. 9 a graphic representation of the induction of T cell unresponsiveness (tolerance) in mice by administration of peptide Y subcutaneously or intravenously followed by challenge with peptide Y. Lymph node cells were isolated, cultured in vitro with peptide Y and cell culture supernatants tested for the ability to support the growth of CTLL-2, an IL-2 dependent T cell clone.

Each bar on FIG. 9 represents the arithmetic mean of triplicate in vivo cultures from one mouse. After in vivo challenge with peptide Y in CFA, lymph node cells from mice which were administered saline by either route specifically responded to challenge with peptide Y in vitro, as shown by IL-2 production (white bars). In contrast, draining lymph node cells isolated from mice who were administered peptide Y intravenously and subcutaneously exhibited a decreased specific IL-2 secretion following challenge with peptide Y in vivo. (dark bars). The results of this experiment demonstrate that subcutaneous and intravenous administration of peptide Y results in T cell non-responsiveness as shown by the decrease in antigen specific production of IL-2.

EXAMPLE 9

Subcutaneous Administration of Peptide Y Response for Induction of Tcell Unresponsiveness in Mice In another experiment, $BDF_1$ mice were tolerized with various doses of peptide X and peptide Y prior to challenge with the peptide in order to determine the lowest dose necessary for the induction of non-responsiveness. Seven groups of mice, each group containing three $BDF_1$ mice, were injected subcutaneously with 0.2 ml PBS containing from 0-500 mg/ml peptide Y (FIG. 10) or peptide X (FIG. 11). Each group of animals was injected at a single dorsal site under the skin between the forelimbs on both day 0 and on day 5. On day 10 all of the animals received a challenge injection of 100 μg peptide Y or peptide X in 200 μl CFA as described above. On day 20 the animals were sacrificed and draining lymph nodes were removed as described above. The lymph node cells were suspended, rinsed, and cultured as above with or without 150 μg/ml of peptide Y or peptide X, as appropriate. The supernatants from the cultures were assayed for IL-2 as described above.

Figure 10:
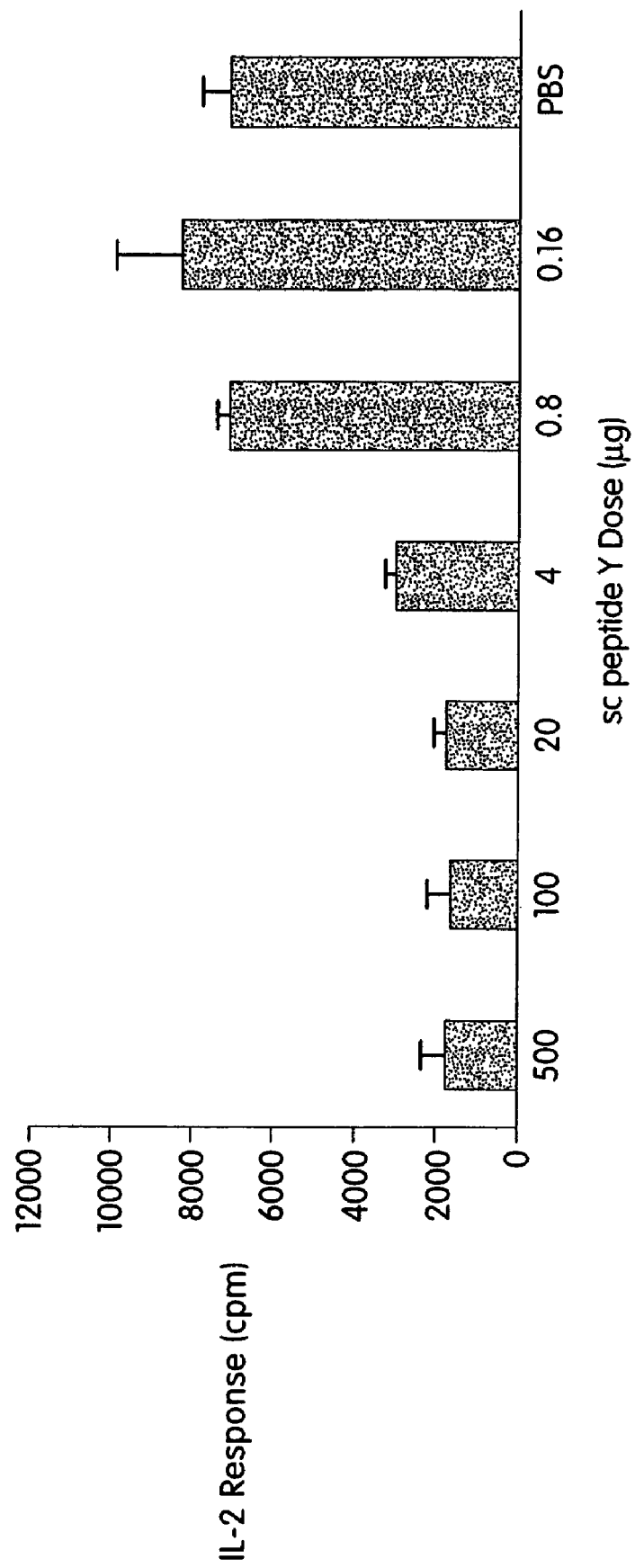
FIG. 10 is a graphic representation of the dose response necessary to induce T cell unresponsiveness with subcutaneous administration of peptide Y in mice.
Figure 11:
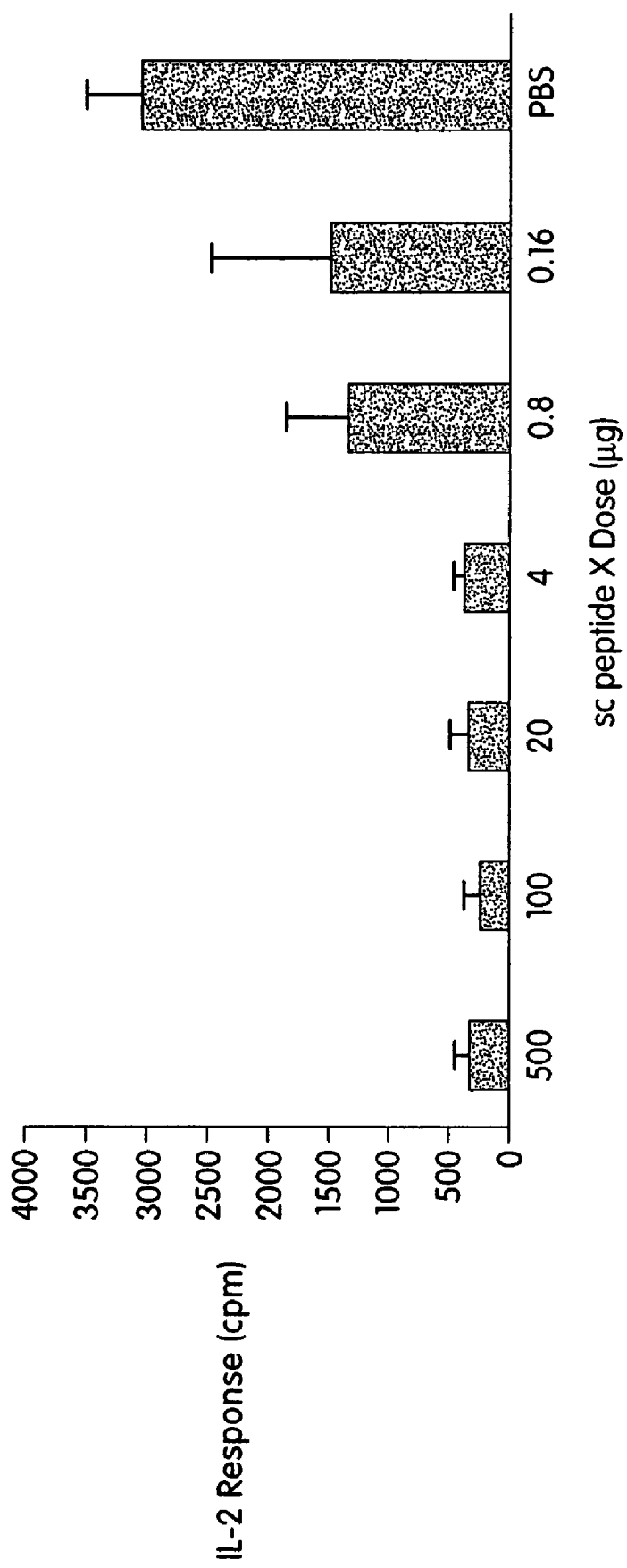
FIG. 11 is a graphic representation of the dose response necessary to induce T cell unresponsiveness with subcutaneous administration of peptide X in mice.

Each bar in FIGS. 10 and 11 represents the average of triplicate cultures of pooled lymph node cells from three mice. The baseline for control cultures (i.e., cells cultured without peptide X or peptide Y) for the IL-2 assay were approximately 1500 cpm (FIG. 10) and approximately 300 cpm (FIG. 11). The dose of peptide per injection needed to completely decrease peptide-specific IL-2 production is between 4 and 20 μg/dose for these experiments using two injections (day 0 and day 5). The results demonstrate that $BDF_1$ strain mice can be tolerized at the T cell level with small doses of peptide X or peptide Y.

EXAMPLE 10

Subcutaneous Administration of a Combination of Peptide X and Peptide Y Induces T Cell Non-responsiveness in Mice In order to determine whether peptide X and peptide Y can induce non-responsiveness when injected in combination, $B6CBAF_1$ mice (C57BL/6J×CBA/J) were tolerized and challenged with a mixture of the two peptides. $B6CBAF_1$ mice respond well to both peptide X and peptide Y, as measured by peptide-specific IL-2 production from lymph node cells isolated from mice who were challenged with either peptide. In this experiment, one group of five B6CBAF$_1$ mice was injected with 300 µg/dose each of peptide X and of peptide Y. The animals were injected at a single dorsal site under the skin between the forelimbs on days 0 and 5. On day 10 the animals received a challenge dose of 100 µg each peptide X and peptide Y in 270 µl total CFA in above location. On day 20 the animals were sacrificed and draining lymph nodes were removed as described above. The lymph node cells were isolated, suspended, rinsed, and cultured as above with or without 150 µg/ml of peptide Y, peptide X, or a combination of peptide X and peptide Y. The supernatants from the cultures were assayed for IL-2 as described above.

Figure 12:
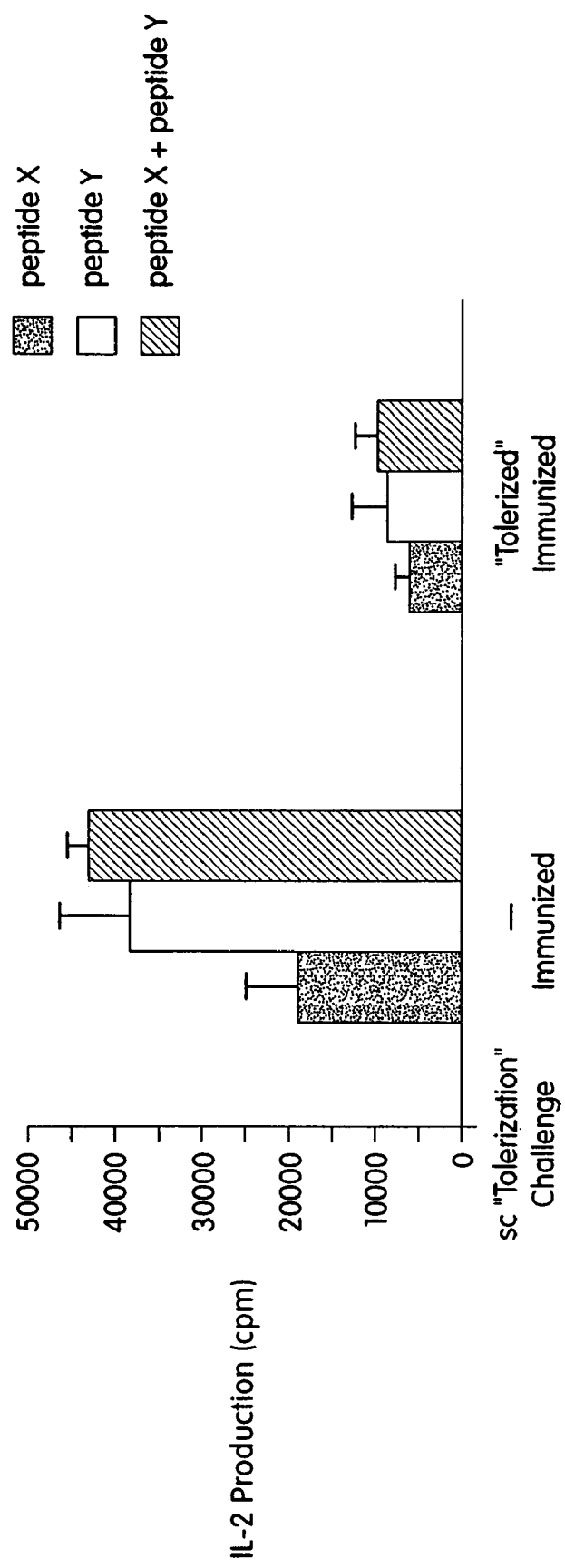
FIG. 12 is a graphic representation of the induction of T cell unresponsiveness in mice by administration of a combination of peptide X and peptide Y subcutaneously followed by challenge with both peptide X and peptide Y. Lymph node cells were isolated, cultured in vitro with a combination of peptide X and peptide Y or with peptide X or peptide Y separately and cell culture supernatants tested for the ability to support the growth of CTLL-2.
Figure 13:
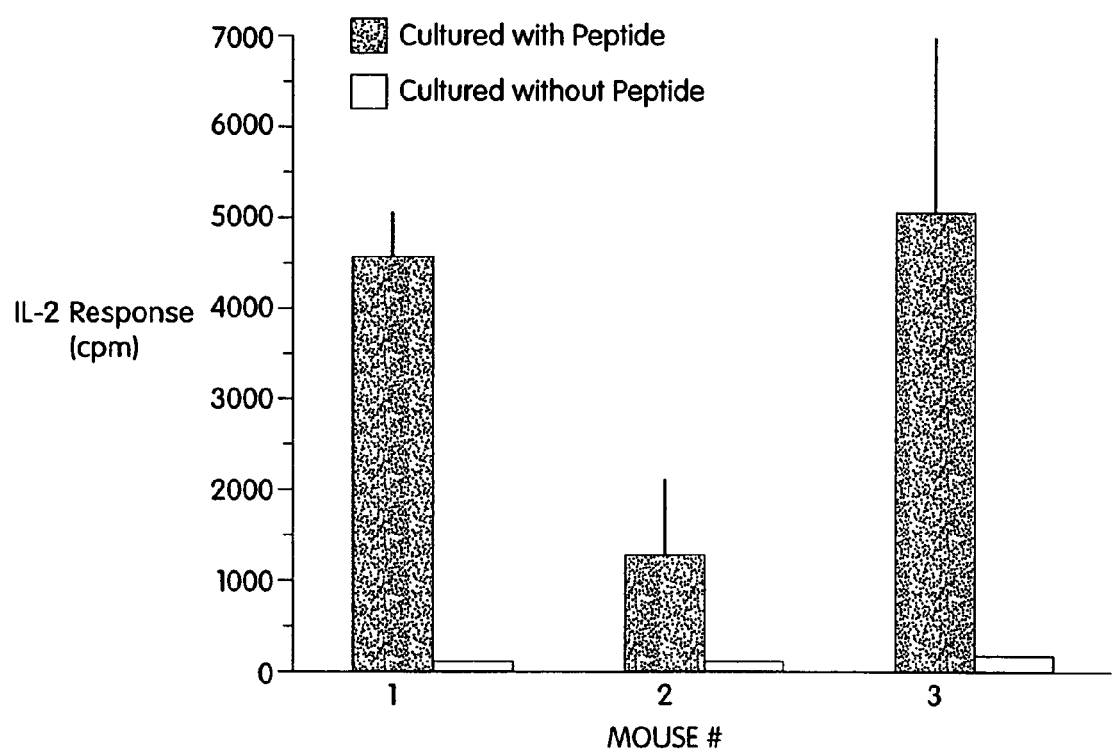
FIG. 13 is a graphic representation of the response of mice preimmunized with TRFP upon administration of peptide Y.

Each bar in FIG. 12 represents the arithmetic average of cpm values of triplicate cultures of pooled draining lymph nodes of five animals. Tolerization of animals with a combination of peptide X and peptide Y results in T cell unresponsiveness in these animals against both of the peptides, presented in vitro either separately or together.

EXAMPLE 11

Peptide Y Specific T Cell Response in Mice Preimmunized with TRFP is Tolerized by Peptide Y When Administered Subcutaneously In order to demonstate that subcutaneous administration of peptide Y can induce T cell nonresponsiveness in primed mice, mice were immunized with purified native whole protein, TRFP, so that there would be T cell response to peptide Y derived from the TRFP protein. Peptide Y in the native protein structure is obscured by the protein conformation. Thus, following TRFP administration, the mice do not produce antibody specific for peptide Y.

Figure 14A:
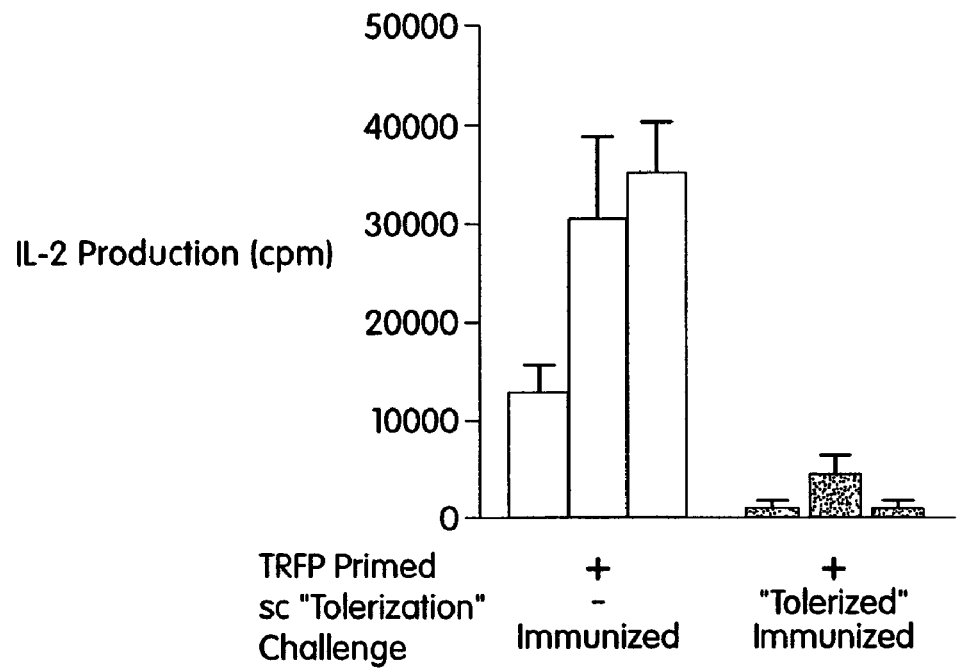
FIG. 14 is a graphic representation of the induction of T cell unresponsiveness in mice primed with TRFP and tolerized with peptide Y. Lymph node cells were isolated, cultured in vitro with peptide Y and cell culture supernatants tested for the ability to support the growth of CTLL-2.
Figure 14B:
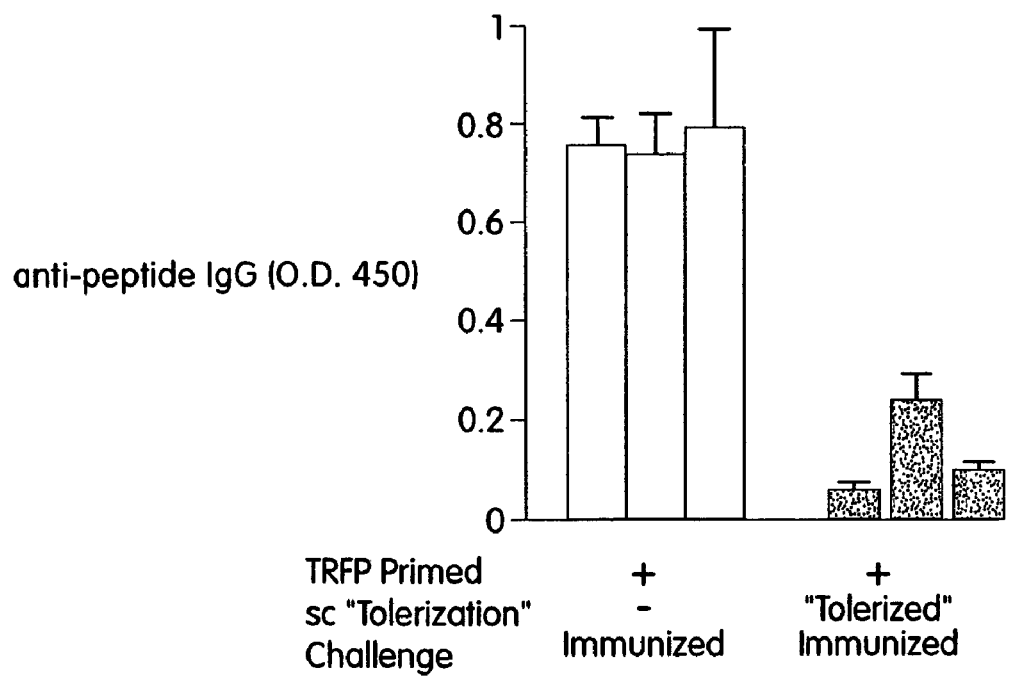

BDF$_1$ mice were each immunized with 100 µg TRFP in 200 µl IFA (Incomplete Freund's Adjuvant) in a single site intraperitoneally. After four months, the mice were bled and grouped according to their anti-TRFP IgG antibody levels as follows. The mice were warmed with an infra-red lamp and bled through one of the tail veins by nicking the vein with a razor blade (Gilette Platinum Plus). The blood was allowed to drip into a serum separating tube (Microtainer, Becton-Dickenson) and allowed to clot. The sera was then separated from the clot by centrifugation at 13,000 rpm. The sera was stored at −20° C. until use. The sera was assayed for TRFP-specific IgG by ELISA. For the IgG assay, immunoaffinity purified TRFP was coated onto Nunc Polysorp 96-well plates by incubation of 50 μl/well of 2 μg/ml TRFP in PBS. Unless mentioned, each incubation step in this protocol was performed for 1 hour at 37° C. After rinsing with PBS, the wells were incubated with 0.5% gelatin in PBS to block excess binding to the plate. The plates were rinsed with PBS containing 0.05% Tween 20. Sera were diluted 1/500 in PBS and incubated in triplicate on the plates. After rinsing, the bound mouse antibody was detected by incubation with biotinylated goat anti-mouse IgG (Southern Biotechnology Associates) diluted 1/10000 in PBS. The plates were rinsed and streptavidin conjugated to horse radish peroxidase (Southern Bio. Ass.) diluted 1/10000 was added for 20 minutes and incubated at room temperature. TMB peroxidase substrate (Kirkegaard and Perry) was used according to directions supplied. The resulting O.D. values were read by an ELISA reader (Bio-Tek modal #310) at 450 nm to quantitate the complexes bound to TRFP protein on the plates. The mice were matched for O.D. of the developed ELISA wells using the 1/500 dilution of each sera and separated into two matched groups of three animals. The range of the values for the TRFP specific IgG of 1/500 dilution sera from these animals was between 1.7 and 2.2.

To determine whether T cells from these TRFP primed mice respond to peptide Y, three TRFP primed, anti-TRFP antibody positive mice (not in the IgG matched groups above, but with similar IgG levels) were sacrificed by cervical dislocation and the spleens were removed and placed in rinsing buffer. Spleens were used because interperitoneal injection leads to strong T cell responses in the spleen. The spleens were suspended and rinsed as detailed above for lymph node cells. The cells were cultured as above with 150 μg/ml peptide Y or with media alone. After 24 hours the supernatants were removed and tested for the presence of IL-2 as previously described. The peptide Y specific IL-2 production shows that these mice responded to peptide Y 4 months after TRFP priming in IFA (FIG. 13).

In addition, TRFP IgG matched groups of mice were tolerized with peptide Y. The unresponsiveness of these animals to peptide Y was then shown by their failure to specifically secrete IL-2 in vitro following an in vivo challenge with peptide Y. The IgG matched groups were tolerized and challenged with peptide Y as follows. One of the two IgG matched groups was injected subcutaneously on days 0 and 5 (day 109 and day 114 after TRFP priming) with 0.2 ml PBS containing 300 μg peptide Y. The other group was injected with PBS only. Both groups were injected at a single dorsal site between the forelimbs. On day 10 (day 119 after TRFP priming) both groups of animals were challenged with 100 μg peptide Y as described above. On day 20 (day 129 after TRFP priming) the animals were sacrificed and the draining lymph nodes were removed as described above. The lymph nodes were suspended, rinsed, and cultured as described above with 150 μg/ml peptide Y (FIG. 14A-B, left panel) or with media alone. After 24 hours, the supernatants of the cultures were tested for IL-2 as described above.

Each bar in the left panel of FIG. 14A-B represents the mean of triplicate cultures of one mouse. This experiment demonstrates that T cells specific for peptide Y can be tolerized in animals which have been preimmunized with TRFP and demonstate a peptide Y specific T cell response at the time of tolerization.

EXAMPLE 12

Subcutaneous Tolerization With Peptide Y Decreases the Peptide Specific Antibody Response in Animals Preimmunized with TRFP The ability of mice to mount an antibody response to peptide Y can be used as an assay for peptide Y specific T helper cell activity. As shown in Example 11, immunization of BDF1 mice with TRFP generates antibodies specific for whole TRFP, with no detectable antibodies specific for peptide Y. The two matched groups of mice described above were bled at the time of sacrifice (ten days after peptide Y/CFA challenge). The serum was separated as previously described. The sera were assayed both for IgG antibody binding specifically to peptide Y. For the IgG assay, immunoaffinity purified peptide Y was coated onto Nunc Polysorp 96-well plates by incubation of 50 μl/well of 20 μg/ml peptide Y in PBS. Each incubation step in this protocol lasts 1 hour at 37° C. The wells were incubated with gelatin in PBS for blocking excess binding to the plate. Sera were diluted in PBS in a range from 1/300 to 1/8100 and incubated in triplicate on the plates. After rinsing, the bound mouse antibody was detected by incubation with biotinylated goat anti-mouse IgG (Southern Biotechnology Associates). Streptavidin conjugated to horse radish peroxidase (Southern Biotechnology Associates) was added to detect antigen bound biotinylated antibody-complexes. TMB peroxidase substrate (Kirkegaard and Perry) was used according to directions supplied and the resulting O.D. values were read by an ELISA reader (Bio-Tek model #310) at 450 nm to quantitate the horse radish peroxidase-containing complexes bound to peptide Y on the plates. The O.D. 450 of the ELISA wells of the sera at 1/900 are shown in FIG. 14. The data from the other sera dilutions were consistent with the data from the 1/900 sera dilution. The peptide Y tolerized animals made little antibody specific for peptide Y in the 10 days after peptide Y/CFA challenge, much less than the animals that were not tolerized. These results suggest that the tolerization of TRFP preimmunized animals with peptide Y reduces peptide Y specific T cell helper activity for antibody production.

The sera were assayed for the presence of peptide Y specific IgM, IgE, and IgG isotypes. The ELISA used to detect antigen specific binding of IgG1, IgG2a, IgG2b, IgG3 and IgM isotypes were similar to the IgG assay described above with the only difference being the biotinylated anti-immunoglobulin used to detect the bound isotype. These assays employed biotinylated goat anti-IgG1 (#1070-08), Southern Biotechnology Associates), anti-IgG2a (#1080-08, SBA), anti-IgG2b (1090-08, SBA) anti-IgG2 (1100-08, SBA), and anti-IgM (1020-08, SBA). Antigens bound IgE was detected similarly, but using biotinylated EM95, a rat monoclonal antibody specific for mouse IgE. (Baniyash M, Eshhar Z, *Eur J. Immunol.* 14:799, 1984). Biotinylated goat anti-rat Ig was used as an added signal amplification step in the IgE ELISA. No binding above background was detected in assays for peptide Y specific IgG2a, IgG3, or IgE. IgG1 was the major isotype seen in the animals which were injected with saline only, with a titer of 1/2700 for all three animals. Of the peptide Y tolerzied animals, two had an IgG1 titer of 1/300 and one had no binding above background. The titers for IgM and IgG2b were similarly effected. The sera from all of the tolerized animals had no IgG2b binding above background while each of the saline control animals had serum titers of 1/300. The peptide Y tolerized animals all had serum IgM titers of 1/300 while the saline controls all had serum IgM titers of 1/900.

Thus the sc peptide injected in saline decreased the antibody response in these primed animals without changing the isotype distribution of the anti-peptide antibody.

EXAMPLE 13

Administration of Peptide Y to Mice Preimmunized with TRFP has No Effect on Antibody Specific for TRFP The animals described in Example #12 which were tolerized to peptide Y had a preexisting antibody response to whole TRFP protein. The anti-TRFP IgG response of these animals before and after the "tolerization" injection (i.e., peptide Y in PBS vs. PBS alone) and the challenge injection (i.e., peptide Y in CFA) was compared. This comparison allows a determination of whether this T cell tolerization has an immediate effect on the TRFP specific IgG levels. The anti-TRFP antibody assay was followed as detailed above. The mouse sera was diluted from 1/500 to 1/13,500 for this assay. The data from the 1/4500 sera dilution is shown in Table 6. Each sera was assayed in duplicate wells and the values were averaged. The background in this assay was about 0.1. The data show that there was no significant change in the quantity of antibody specific for TRFP in any of these mice in this time frame. Thus, tolerization of the T cells specific for peptide Y had no effect on the anti-TRFP antibody in the 20 days following tolerization.

TABLE 6

ELISA analysis of specific IgG binding of mouse sera to TRFP

|  | ELISA O.D.-sera sampled before "tolerization" and challenge | ELISA O.D.-sera sampled after "tolerization and challenge |
|---|---|---|
| "tolerization" with PBS only |  |  |
| mouse #1 | 0.842 | 0.782 |
| mouse #2 | 0.580 | 0.503 |
| mouse #3 | 0.725 | 0.693 |
| "tolerization" with peptide Y in PBS |  |  |
| mouse #1 | 0.670 | 0.492 |
| mouse #2 | 0.687 | 0.654 |
| mouse #3 | 0.686 | 0.585 |

The values given are averages of duplicate wells of 1/4500 dilutions of the sera.

EXAMPLE 14

Subcutaneous Administration of Peptide Y Induces Non-responsiveness in Il-2 and Il-4 Producing T Cells in Mice Primed with TRFP There are several phenotypic classes of T helper cells which can be differentiated by their production of lymphokines. $Th_1$ cells produce IL-2 and γ-interferon, as well as other lymphokines. $Th_2$ cells produce IL-4 and other lymphokines. IL-2 production is easily measured from primary in vitro lymph node cultures through the IL-2 dependent CTLL-2 cell line. Similarly, IL-4 can be measured with cultures of the IL-4 dependent CT4S cells (provided by W. Paul). However, production of IL-4 from primary in vitro culture is low and not reproducible. In order to determine whether tolerization with peptide Y effects both types of T helper cells, we pooled lymph node cells from the two groups of mice (described previously) that were tolerized, challenged, and assayed for T cell unresponsiveness. The cells ($2\times10^7$ total) were cultured in 5 ml culture media containing 30 μg/ml peptide Y. After 21 days incubation at 37° C. and 5% $CO_2$, the cells were rinsed two times with culture media and replated at $4\times10^6$ cells/ml in triplicate 0.2 ml wells with or without 150 μg/ml peptide Y for both the IL-2 production assay and the IL-4 production assay. Samples (50 μl each) of the supernatants for the IL-2 assay were removed at 24 hours and assayed as detailed above. Samples for the IL-4 assay were removed at 48 hours and stored at 4° C. until use (2 days minimum). The IL-4 content was assayed by the ability of the supernatants to support the growth of the CT4S line. CT4S cells ($1\times10^4$/well) were added to the warmed culture supernatants and incubated 40 hours at 37° C. and 5% $CO_2$. $^3$H-thymidine (1 μCi/50 ml culture media/well) was added for an additional 8 hours of culture to quantitate CT4S growth through incorporation of the thymidine into DNA. The cells were harvested after freezing the plates to dislodge the slightly adherent CT4S cells. The plates were harvested and counted identically to the IL-2 assays detailed above.

Figure 15A:
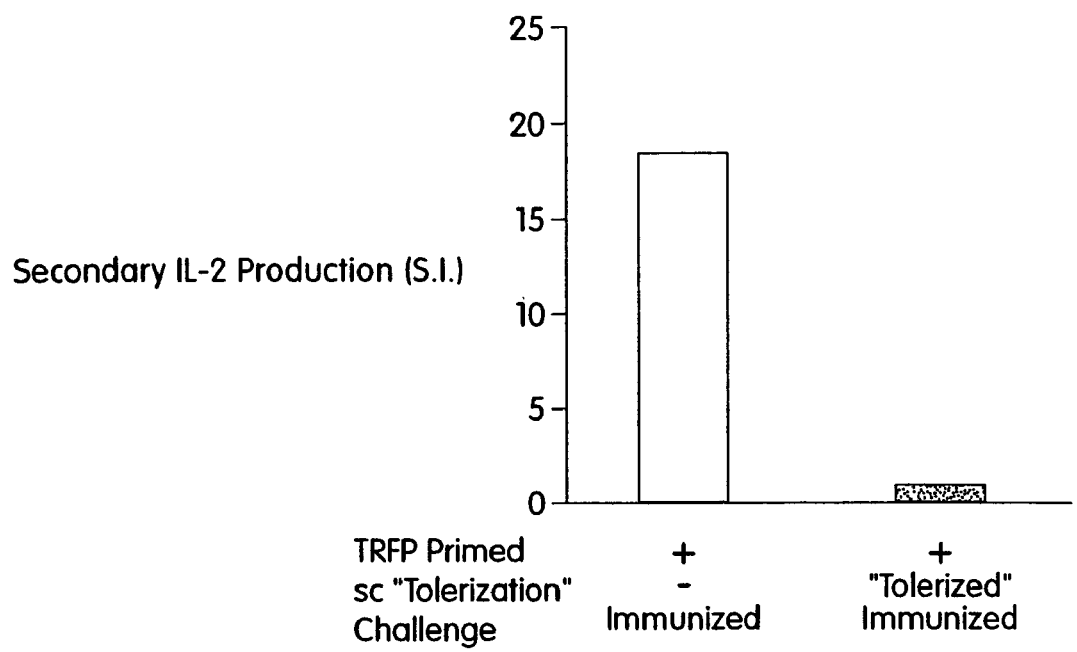
Figure 15B:
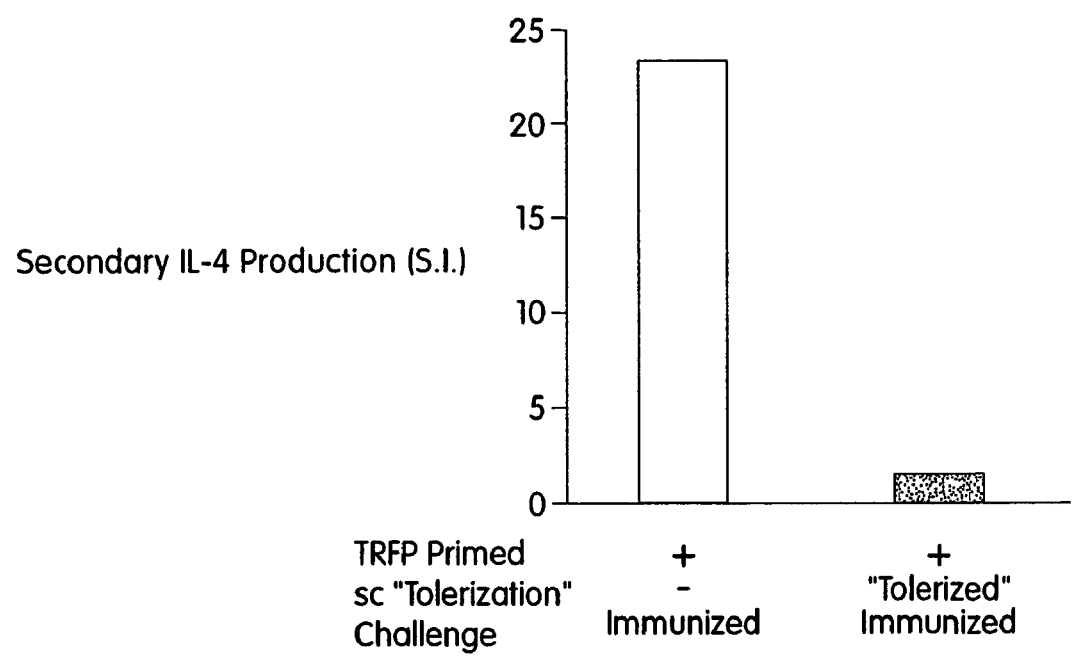
FIG. 15B is a graphic representation of the induction of IgG unresponsiveness in mice primed with TRFP and tolerized with peptide Y. A sera sample was obtained and assayed for binding to peptide Y in a standard ELISA assay.
Figure 16:
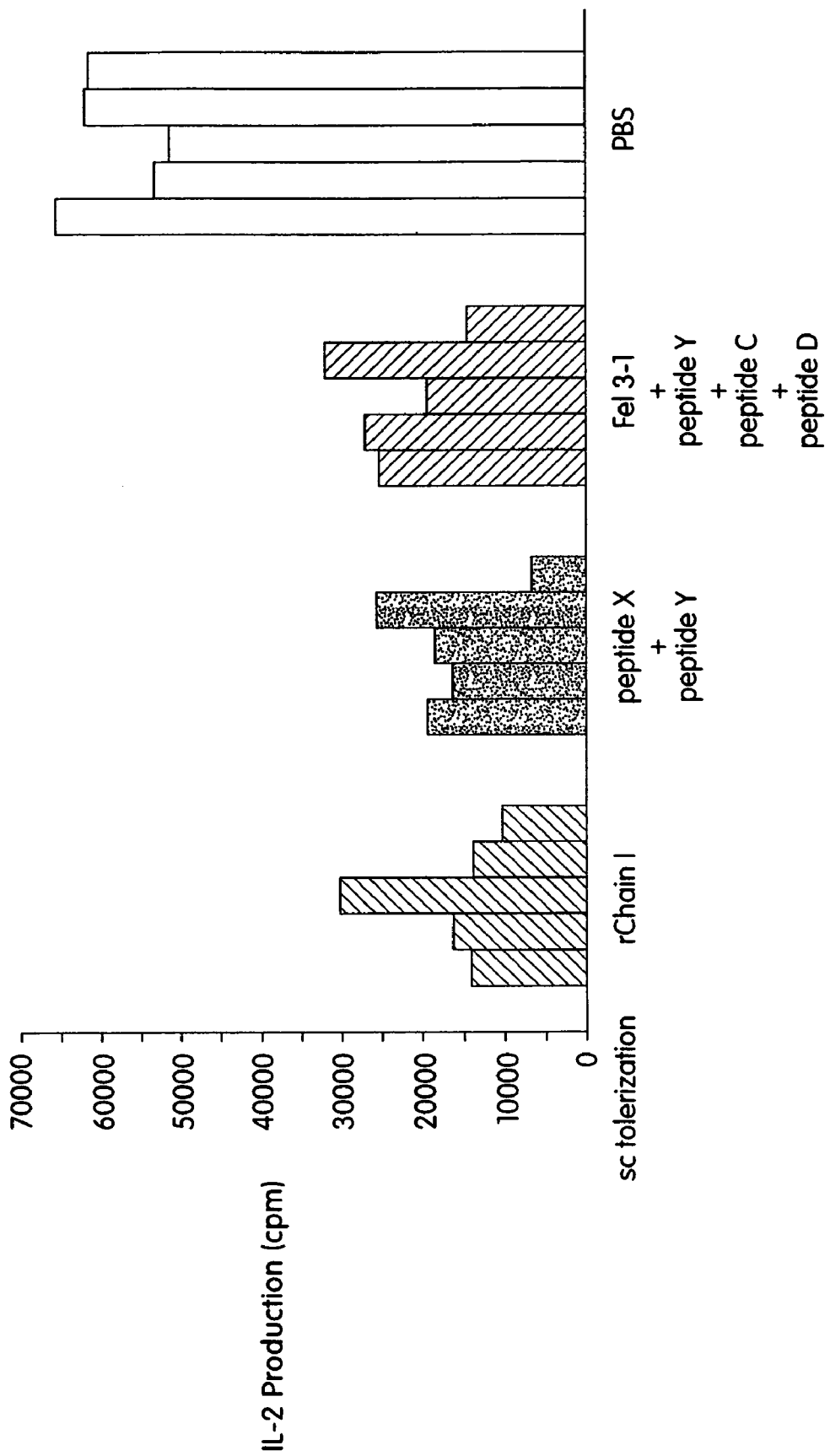
FIG. 16 is a graphic representation of the induction of T cell unresponsiveness in mice with recombinant chain 1 of TRFP (peptide Y and peptide X) peptides Fel 3-1, peptide Y, IPC-5 and IPC-6. The mice were challenged with recombinant chain 1 of TRFP. Lymph node cells were isolated, cultured with recombinant chain 1 of TRFP and cell culture supernatants tested for the ability to support the growth of CTLL-2.
Figure 19:
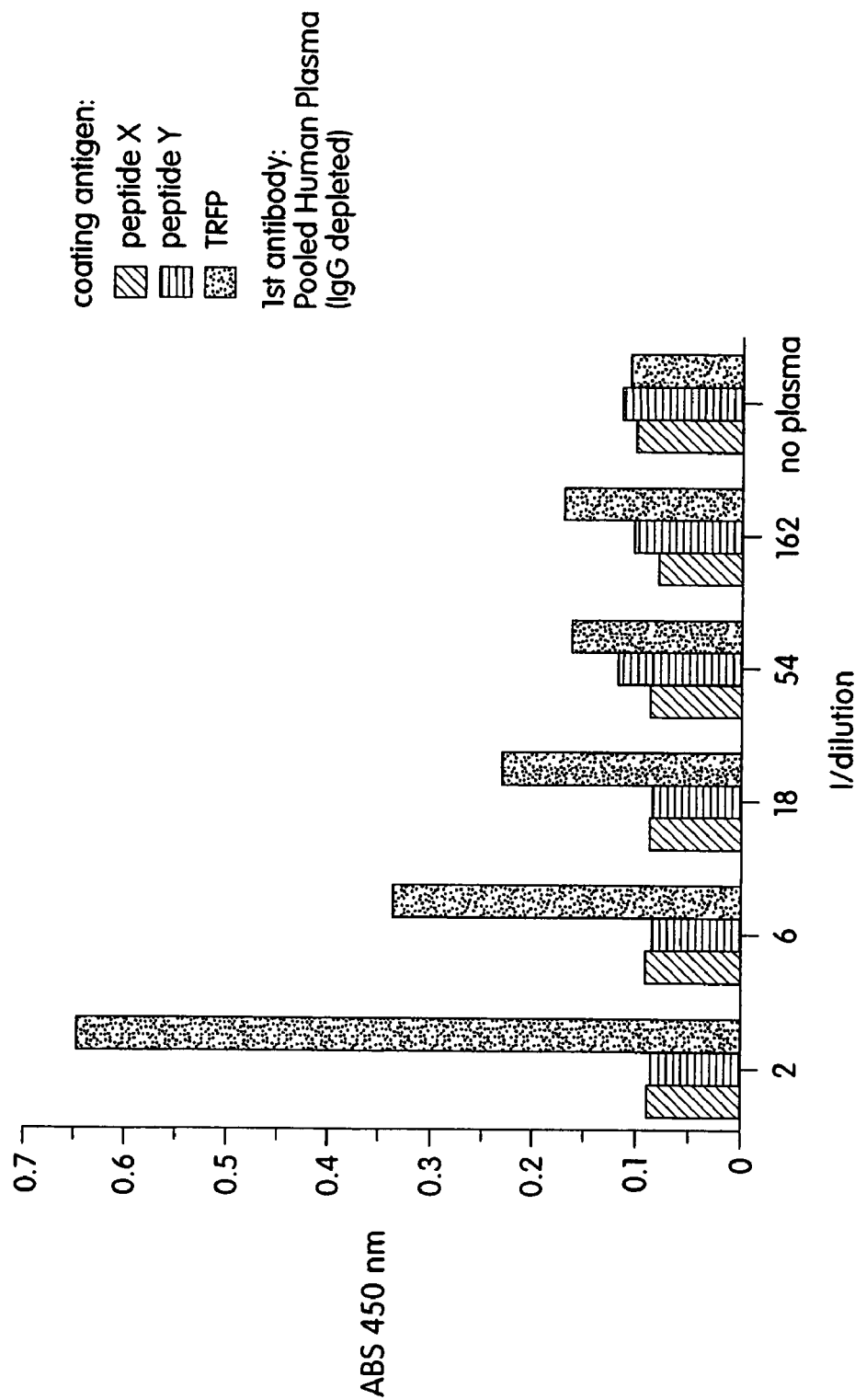
FIG. 19 is a graphic representation of the results of direct binding studies of human IgE to TRFP, peptide X (SEQ. ID. NO: 17) and peptide Y (SEQ. ID. NO: 18).

For both the secondary IL-2 and the secondary IL-4 assays (FIG. 15), the average number of counts from the triplicate 150 μg/ml peptide Y wells was divided by the average number of counts from the wells without peptide Y to determine a stimulation index. This was necessary because the no antigen background in the secondary cultures is more variable than in primary cultures. The peptide tolerization decreased the peptide specific production of both IL-2 and IL-4 in these secondary in vitro cultures. These data suggest that tolerization with peptide Y decreases the antigen specific production of both IL-2 and IL-4. The effect indicates a tolerogenic effect by administration of peptide Y on both classes of T helper cells.

EXAMPLE 15A

Subcutaneous Administration of Peptide X and Peptide Y Decreases T Cell Response to Recombinant Chain 1 of TRFP Four groups of $B6CBAF_1$ mice were "tolerized" by subcutaneous injection with either PBS alone or PBS containing recombinant chain 1 of TRFP; PBS containing peptide X and peptide Y; or PBS containing peptides Fel 3-1, peptide Y, IPC-5, and IPC-6. The mice were injected with 150 μg/dose of either the TRFP chain 1 or each of the peptides (days 0 and 5). The PBS alone and the PBS/peptides were injected in 300 μl/dose. The PBS/chain 1 of the TRFP protein was injected in 100 μl/dose. All tolerizing doses were at a single site under the dorsal skin between the forelimbs. On day 10 all of the animals received a challenge injection of 100 μg recombinant chain 1 of TRFP in 200 μl CFA as described above. On day 20 the animals were sacrificed and draining lymph nodes were removed as described above. The lymph node cells were suspended, rinsed, and cultured as above with or without 150 μg/ml recombinant chain 1 of TRFP. The lymph node cell cultures in this experiment were each 0.1 ml. The supernatants from the cultures were assayed for IL-2 as described above.

Each bar in FIG. 16 represents the average of IL-2 produced by triplicate cultures of lymph node cells from five individual mice. IL-2 assays from cultures of these lymph node cells without peptide was approximately 500 cpm. The results show that tolerization with peptide X and peptide Y and tolerization with chain 1 of TRFP is effective in decreasing IL-2 production specific for chain 1 of TRFP after in vivo challenge with the chain 1 protein TRFP. The results indicate that tolerization with two peptides from chain #1 (peptide X and peptide Y) are as effective as tolerization with four peptides from chain #1 (Fel 3-1, peptide Y, peptide C and peptide D) or as effective as tolerization with TRFP chain #1 itself.

EXAMPLE 14B

Duration of Peptide Inhibitory Effects on T Cell Function in Lonterm Primed Mice Mice were injected with recombinant TRFP Chain 1 (rCh1) in Incomplete Freund's Adjuvant. Three months later all the mice were primed to rch1 as judged by their development of significant titers of anti-rch1 antibody. Primed mice were injected twice with IPC-2 in saline, followed by an injectino of peptide Y in adjuvant. Lymph nodes from these mice were restimulated 7 days later with peptide Y. Cells were taken from mice injected at different times with peptide Y in adjuvant following the final subcutaneous injection of peptide Y. FIG. 25 shows that the inhibitory effects of subcutaneous peptide injection on T cell function on primed mice are observable up to 56 days later.

EXAMPLE 16

IgE Binding Studies With Peptide X and Peptide Y

The objective of these studies was to analyze the extent of human IgE binding to peptide X and peptide Y derived from the TRFP chain #1 sequence. An ELISA assay had been previously performed to quantitate IgE binding to TRFP with cat allergic patient plasma as the source of IgE. This assay format was then extended to analyze the potential for anti-TRFP IgE to bind peptides X and Y. These assays also included equal mixtures of the two peptides and each peptide separately conjugated to HSA (human serum albumin). Dot blot assays on some of these antigens were also run as an alternative means of detecting IgE binding. The clinical implications would be that if these peptides bind a significant portion of anti-TRFP IgE, adverse allergic reactions would be more likely during treatment of an allergic individual.

ELISA

The basic format of these ELISA assays was a direct binding assay wherein the antigen was coated onto the wells of a 96 well microtitre dish and then antibodies in solution are added and assayed for the binding capacity. The protocol for these assays was as follows:

Corning assay plates (#25882-96) were coated with 10 μg/ml of each coating antigen; affinity purified TRFP, peptide X, or peptide Y, peptide X and peptide Y mixed, peptide X/HSA, or peptide Y/HSA in PBS (phosphate buffered saline), at 50 μg/well and incubated overnight at 4° C. The peptides were conjugated to HSA (human serum albumin) by two different methods based on their chemical structure. The conjugation reaction with peptide X used the reagents and protocol of the Pierce Imject Immungen EDC conjugation kit (Pierce, Rockland, Ill.). Peptide Y was conjugated to HSA through its cysteine residue using the sulfo-SMCC reagent (Pierce). Both conjugates were filter purified and dialyzed against PBS. In the ELISA assay, the unbound coating antigens were removed and the wells were blocked with 0.5% gelatin in PBS, 200 μl/well for 2 hours at room temperature. The antibody solution was a pool of plasma samples from 20 patients that were skin test positive for commercial cat extract which was serially diluted with PBS-Tween 20 (PBS with 0.05% nonionic detergent Tween-Sigma, St. Louis Mo.) and 100 μl/well was added and incubated overnight at 4° C. (plasma dilutions are tested in duplicate). This plasma pool had been depleted of most of the IgG antibodies by extraction with Protein G-Agarose (GammaBind G-Agarose, Genex Corp. Gaithersburg, Md.). The second antibody (biotinylated goat anti-Human IgE, 1:1000 Kirkegaard & Perry Laboratories Inc. Gaithersburg, Md.), was added at 100 μl/well for one hour at room temperature. This solution was removed and streptavidin-HRPO, 1:1000, (Southern Biotechnology Associates, Inc., Birmingham, Ala.) was then added at 100 μl/well for one hour at room temperature (all wells were washed three times with PBS-Tween between each incubation step). TMB Membrane Peroxidase Substrate system (Kirkegaard & Perry Laboratories) was freshly mixed, and added at 100 μl/well. The color was allowed to develop for 2-5 minutes. The reaction was stopped by the addition of 100 ml/well of 1 M phosphoric acid. Plates are read on a Microplate EL 310 Autoreader (Biotek Instruments, Winooski, Vt.) with a 450 nm filter. The absorbance levels of duplicate wells were averaged. The graphed results (log of the dilution vs absorbance) of the ELISA assays are shown in FIG. 19.

FIG. 19 is the graphic representation of ELISA assays for TRFP, peptide X and peptide Y IgE binding. Because IgE antibody is the least abundant antibody in human plasma the first dilution, 1:2 in PBS, shows an absorbance reading of 0.65 for TRFP binding. Although clearly positive for binding, this is still a low initial absorbance reading. Positive binding is defined as absorbance readings that are greater than or equal to two times the background level. Some individual patients have much higher levels of anti-TRFP IgE which is reflected in the higher absorbance readings (data not shown). This pool of IgE depleted plasma represents an average of all the different patients anti-TRFP IgE. This assay can accurately detect the relative quantity of anti-TRFP IgE reactive with the coated TRFP antigens. The two peptide antigens, peptide X and peptide Y, do not demonstrate any specific IgE binding at any of the dilutions examined. The negative control for these binding assays is the level of binding to wells which have had no antigen coated on them. For the positive control for the presence of peptide coated on the wells was an ELISA using anti-peptide antisera against either peptide X or peptide Y was used.

Table 7 shows the percent positive binding as summarized data from different numbers of cat allergic patients. A smaller set of patients was examined for IgE binding to the mix of peptides and the peptides conjugated to HSA. Again the positive control for the presence of peptides or peptide conjugates was binding of anti-peptide antisera (now shown).

TABLE 7

Summary of Analysis of Direct IgE Recognition of peptide X and peptide Y

| Antigens tested: | Positive Binding | N |
| --- | --- | --- |
| ELISA* | | |
| TRFP | 100% | 12 |
| Peptide X | 0% | 12 |
| Peptide Y | 0% | 12 |
| Peptide X + Peptide Y | 0% | 4 |
| Peptide X/HSA | 0% | 3 |
| Peptide Y/HSA | 0% | 3 |
| Dot Blot | | |
| TRFP | 100% | 8 |
| Peptide X | 0% | 8 |
| Peptide Y | 0% | 8 |

IgE binding studies using a similar protocol as described above were carried out using peptides Fel 8-1, Fel 31-1, Fel 31-2, Fel 31-4, and Fel 31-3. None of these peptides showed IgE binding.

Dot Blots:

The dot blot assay is similar to ELISA in that is a direct binding assay with the antigen bound to a solid phase matrix. In the case of the dot blot assay the matrix is nitrocellulose paper and results are based on autoradiography with $^{125}$I-Streptavidin binding to a biotin labeled second antibody.

Dot blot protocol: Antigen; TRFP, peptide X and peptide Y, were coated on 0.1 mm nitrocellulose sheet using 96-well dot blot manifold (Biorad, Richmond, Calif.) for 45 min. at room temperature in 100 μl sample volumes. TRFP was coated at 2, 0.2 and 0.02 μg/dot and the peptides at 10, 1 and 0.1 μg/dot. Wells were then washed with 200 μl PBS. After equilibration of blots with Tween solution, (Tris-HCL; pH 7.5 0.025M NaCl 0.17 m Tween-20 0.5%) all sections were blocked with 1% nonfat dry milk, 1% fetal calf serun/Tween solution for 1-1.5 hour. Patient plasma was used at 10% (v/v) in 1% milt/Tween solution and preabsorbed on blank strips of nitrocellulose for 1 hour. After preabsorption, the diluted patient plasma sample was incubated with the antigen bearing dot blot overnight at room temperature (RT). Nitrocellulose dot blot was incubated in biotinylated goat anti-human IgE (1:2500) in Tween solution for 2 hours RT. After washing, the sections were incubated in 1 μCi $^{125}$I-Streptavidin, 1 hour. Following removal of unbound label by extensive washing, the blots were exposed to film for 16 hours.

The summarized results of the dot blot assays are shown in Table 7. At all concentrations the peptide antigen dots were negative for specific IgE binding and with this patient set all were positive for TRFP binding.

Conclusion:

By using the direct binding ELISA method we have clearly demonstrated IgE binding to affinity purified TRFP. With this same assay we detect no specific binding of cat allergic IgE to peptide X and peptide Y. For further demonstration of lack of peptide binding, a mixture of the two peptides as the coating antigens was examined. This mixture was negative for detectable, specific IgE binding as were the individual peptides which has been conjugated to human serum albumin. The rationale for including these forms was to check that the lack of binding was not just due to some conformation of the peptide as it is directly bound to the plate. These results are correlated with those from the dot blot assay wherein a distinctly different matrix is used that includes a different endpoint readout (i.e., autoradiography versus enzymatic color development). No direct IgE binding to Fel 8-3 and Fel 30-4 was detected.

EXAMPLE 17

Histamine Release Analysis Comparing TRFP to Peptide X and Peptide Y

The objective of the histamine release analysis was to directly assay the effects of peptides or TRFP in an in vitro allergic response system. The release of histamine through IgE recognition and IgE receptor crosslinking on live cells directly assays the allergic potential of a protein antigen. The aim of these studies was to compare this allergenic potential between the known allergen TRFP and peptide X and peptide Y.

The histamine release assay used for these studies is based on the detection of an acylated derivative of histamine using a specific monoclonal antibody (Morel, A. M. and Delaage, M. A.; 1988, *J. Allergy Clin. Immunol.* 82:646-654.) This assay was performed as two separate protocols: 1) the release of histamine from basophils present in heparinized whole blood in the presence of different concentrations of antigens and 2) the actual assaying of histamine present in the supernates of the release reactions following cell removal by centrifugation. The reagents for this histamine radioimmunoassay are supplied commercially as a kit by Amac Inc. (Westbrook, Me.).

Whole blood was drawn from cat allergic patients using heparinized syringes or vacutainers. The antigens, affinity purified TRFP, peptide X and peptide Y, were diluted to 2x concentration in PACM (PIPES buffer 25 mM, NaCl 110 mM, KCl 5.0 mM, human serum albumin 0.003%, CaCl$_2$ 5 mM, MgCl$_2$ 2 mM, pH 7.3) buffer with 0.2 ml in each 1.5 ml polypropylene tube. the same volume of blood, 0.25 mls, was added to each tube and the reactions were started by inversion. The buffer control consisted of whole blood with just buffer and no added antigen. The release reactions were then carried out at 37° C. for 30 minutes. After this incubation the tubes were centrifuged at 1500 RPM for 3 minutes and the supernates were carefully removed. It was important to spin gently so that there would be no cell lysis giving misleading results. For the total histamine release values a 100 µl blood sample was boiled for 3 minutes in a total volume of 1 ml with PACM buffer. At this point the supernates were either frozen at −20° C. for later analysis or processed immediately.

For the RIA analysis, a 50 µl aliquot of the release supernatant was diluted 1:4 with Histamine release buffer (supplied with the kit from Amac Inc.) Then 100 µl of each diluted supernatant was added to the tubes containing the acylation reagent (a lyophilized powder). Immediately after the addition of each supernatant, 50 µl of acylation buffer was added and the tube mixed by vortexing until the reactants were completely dissolved. The acylation reactions were allowed to go to completion at R.T. for $\geq$30 minutes. A set of histamine standards was supplied with the kit and these all were processed by the acylation reaction (i.e., 100 µl of each standard and 50 µl of acylation buffer in each acylation reaction tube.) Then 50 µl of each acylation reaction was added to the bottom of a monoclonal antibody coated 12×75 mM plastic tube. This monoclonal antibody recognizes the acylated histamine derivative as its epitope. Finally, 500 µls of $^{125}$I labelled tracer was added to each tube on ice and the binding reaction was carried out overnight at 4° C. ($\geq$18 hrs). The binding reactions were stopped by aspiration of the solutions from each tube. Then they were counted on a gamma counter (Cobra 5005, Beckman Inc.) for two minutes/tube.

Following the quantitation of $^{125}$I label/tube the standard curve is generated from the histamine standard counts and plotted on semi-log paper. Because this is a competition assay, with labelled $^{125}$I tracer competing with the standards or unknowns for cell supernatants, the lower the recorded counts the greater the amount of cold acylated histamine in the binding assay. The data points were then generated by reading off the values on the plotted standard curve of counts versus histamine concentration (in nM).

This type of analysis for histamine is a very sensitive, accurate method of measurement.

Figure 20:
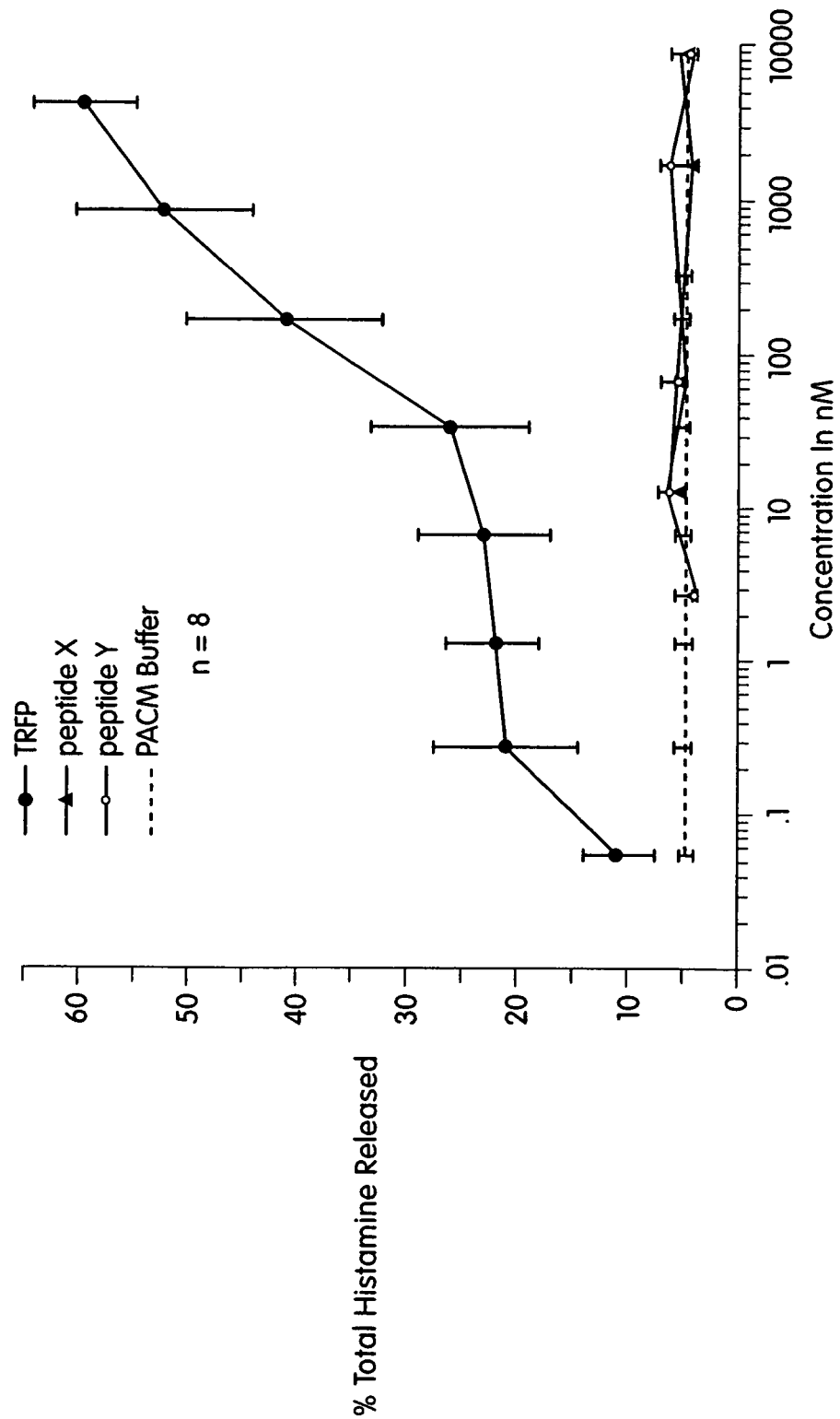
FIG. 20 is a graphic representation of the results of histamine release from basophils in response to TRFP, peptide X (SEQ. ID. NO: 17) and peptide Y (SEQ. ID. NO: 18).
Figure 21A:
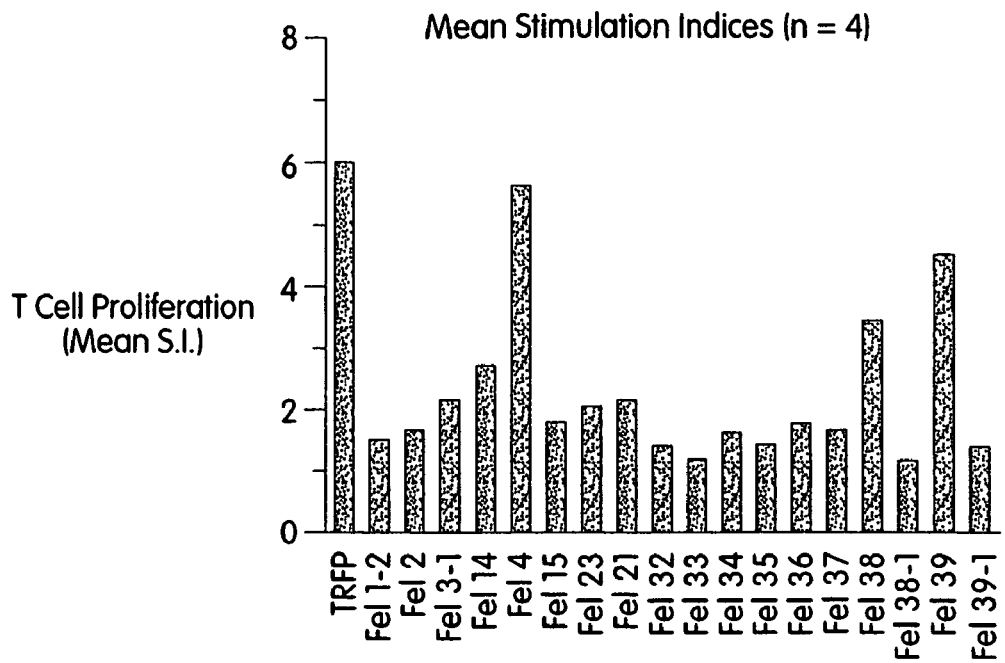
FIGS. 21A-C is a graphic representation of depicting the response of T cells from patients #688, #730, #738, and #807 primed in vitro to TRFP and analyzed for response to various peptides derived from TRFP as measured by IL-2 production and IL-4 production.
Figure 21B:
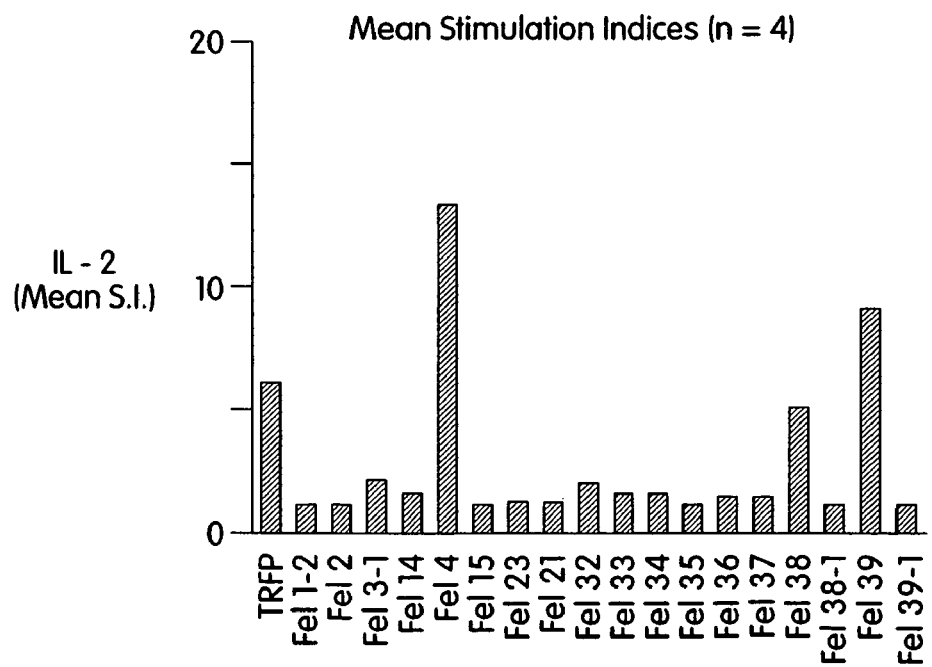
Figure 21C:
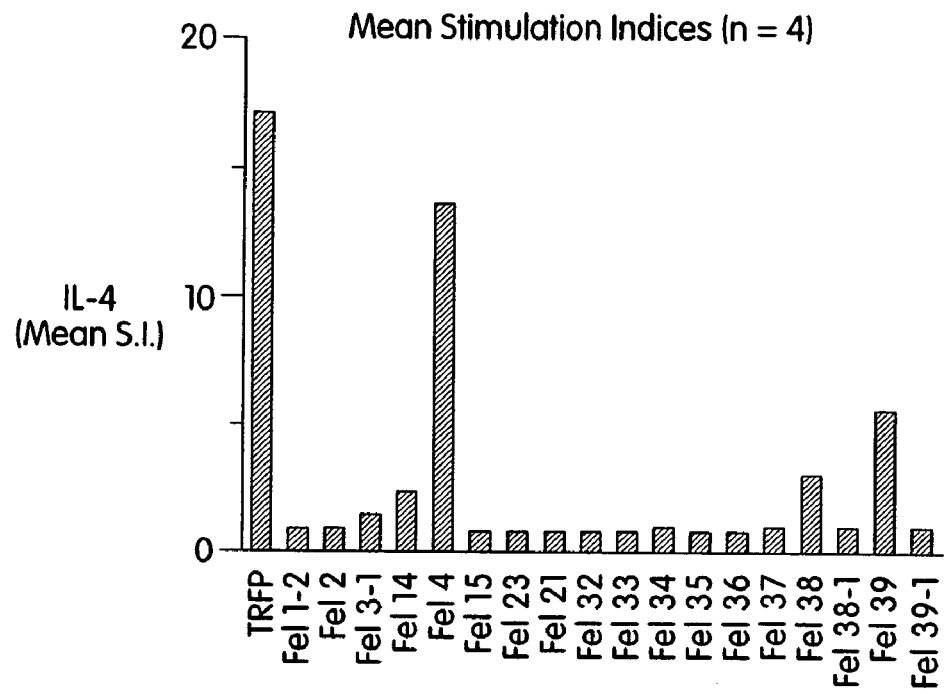
Figure 22:
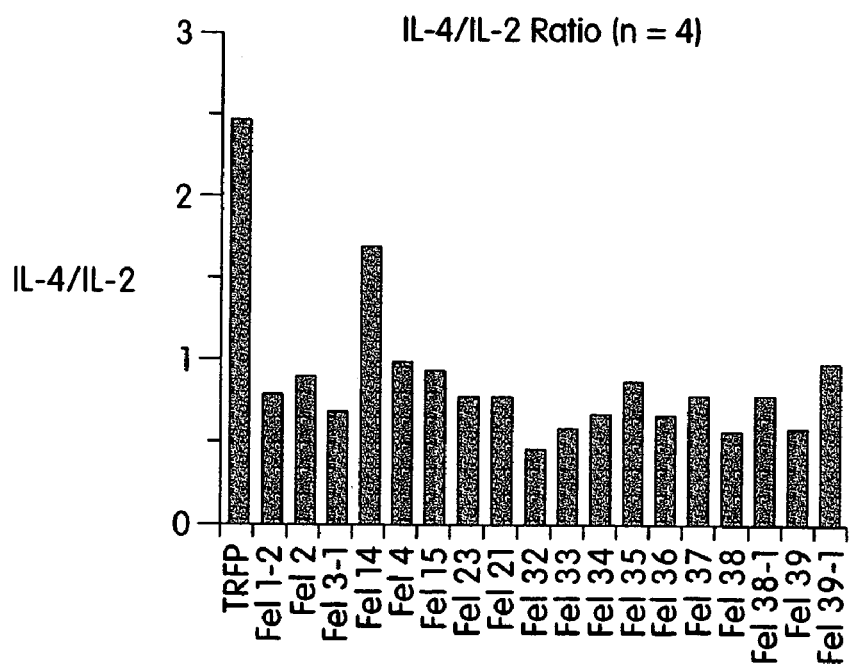
FIG. 22 is a graph depicting the ratio of IL4 production to IL-2 production by T cell lines from cat allergic patients, #688, #730, #738, and #807 in response to various peptides derived from TRFP.
Figure 23:
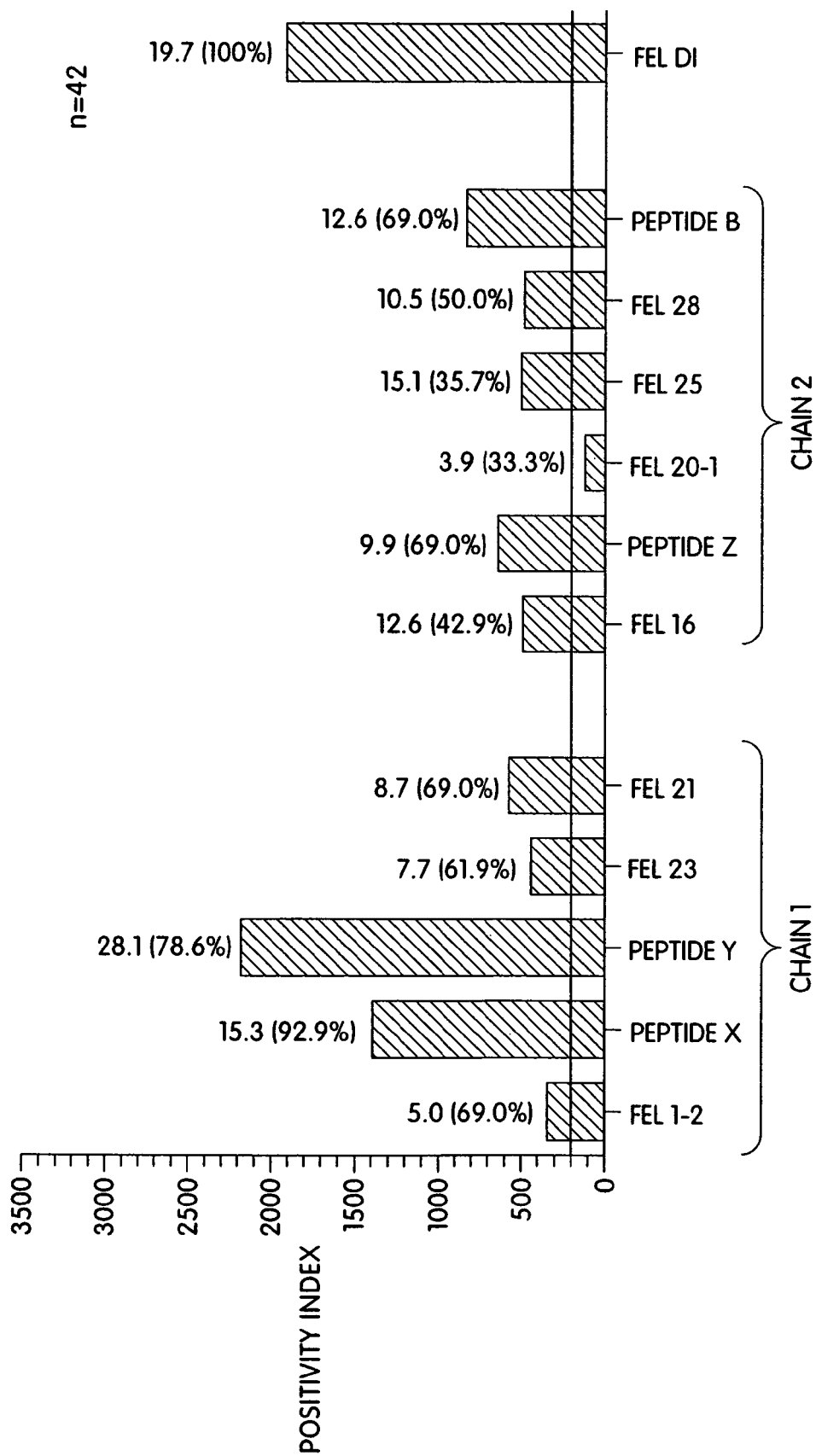
FIG. 23 is a graphic representation depicting the response of T cells from 42 patients (n=42) primed in vitro with purified native TRFP and analyzed for T cell response to selected peptides of the invention derived from TRFP, by the percent response with an S.I. of at least 2 within the individuals tested (above each bar), the mean stimulation index (S.I.) (above each bar), and the positivity index (Yaxis) which is the mean S.I. multiplied by the percent response.
Figure 24A:
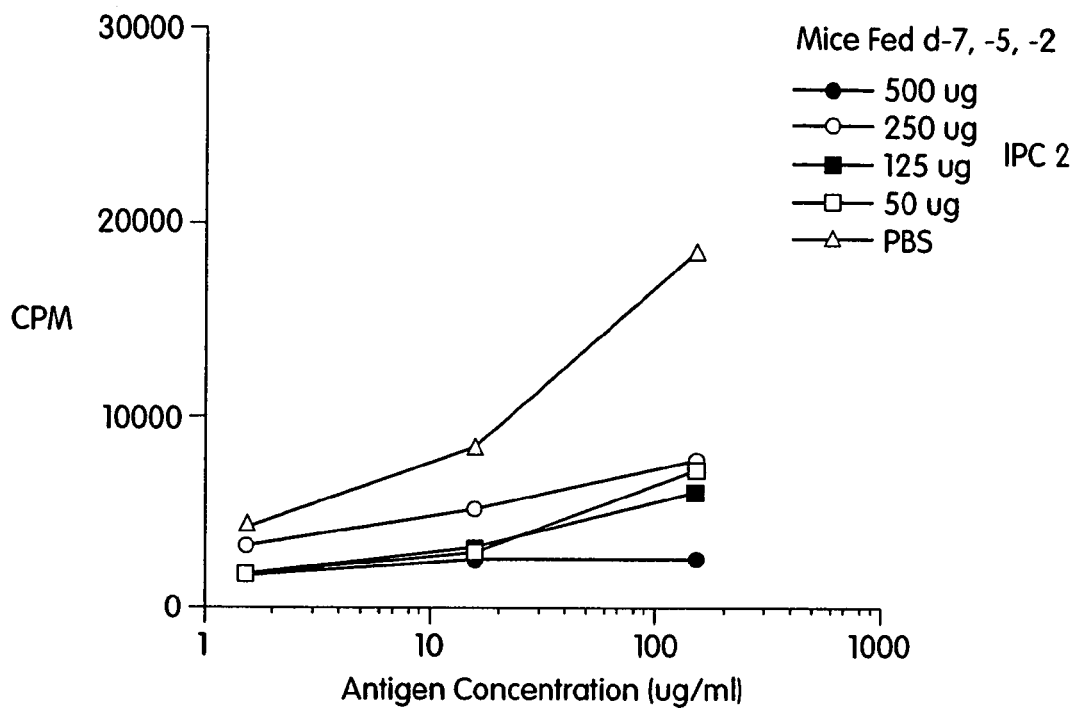
FIG. 24A is a graph showing the results of an IL-2 assay performed on spleen cells from animals treated with different amounts of orally administered Peptide Y, as described in Protocol 1, in Example 24, and cultured in the presence of peptide Y.
Figure 24B:
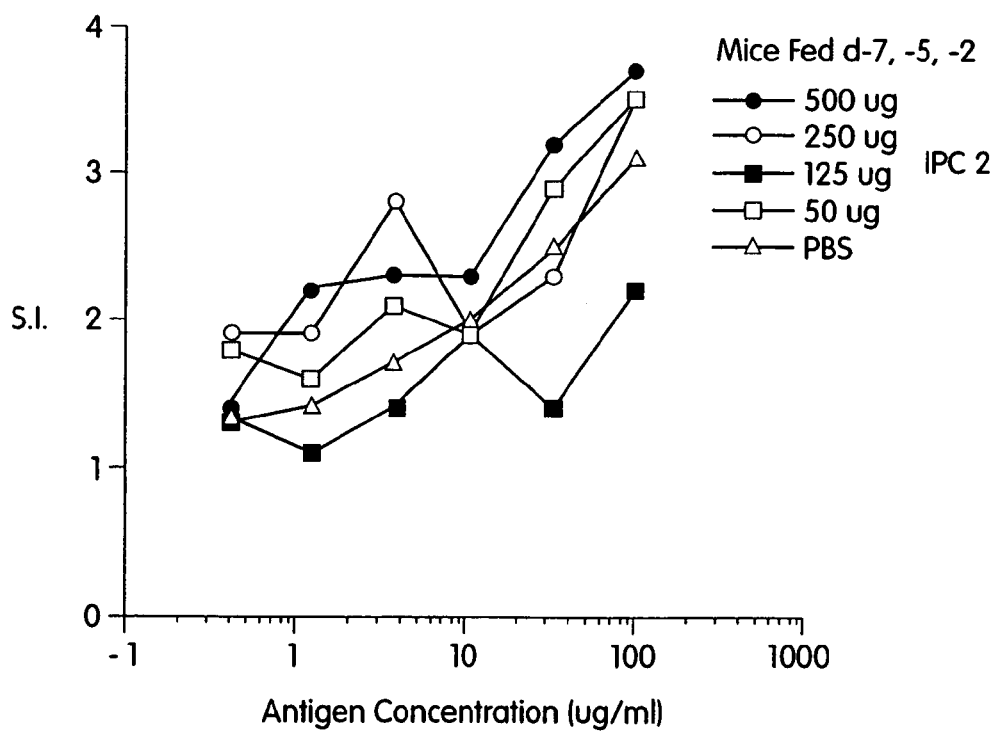
FIG. 24B is a graph showing the results of a proliferation assay performed on spleen cells from animals treated with different amounts of orally administered Peptide Y, as described in protocol 1, in Example 24, and cultured in the presence of Peptide Y.
Figure 25:
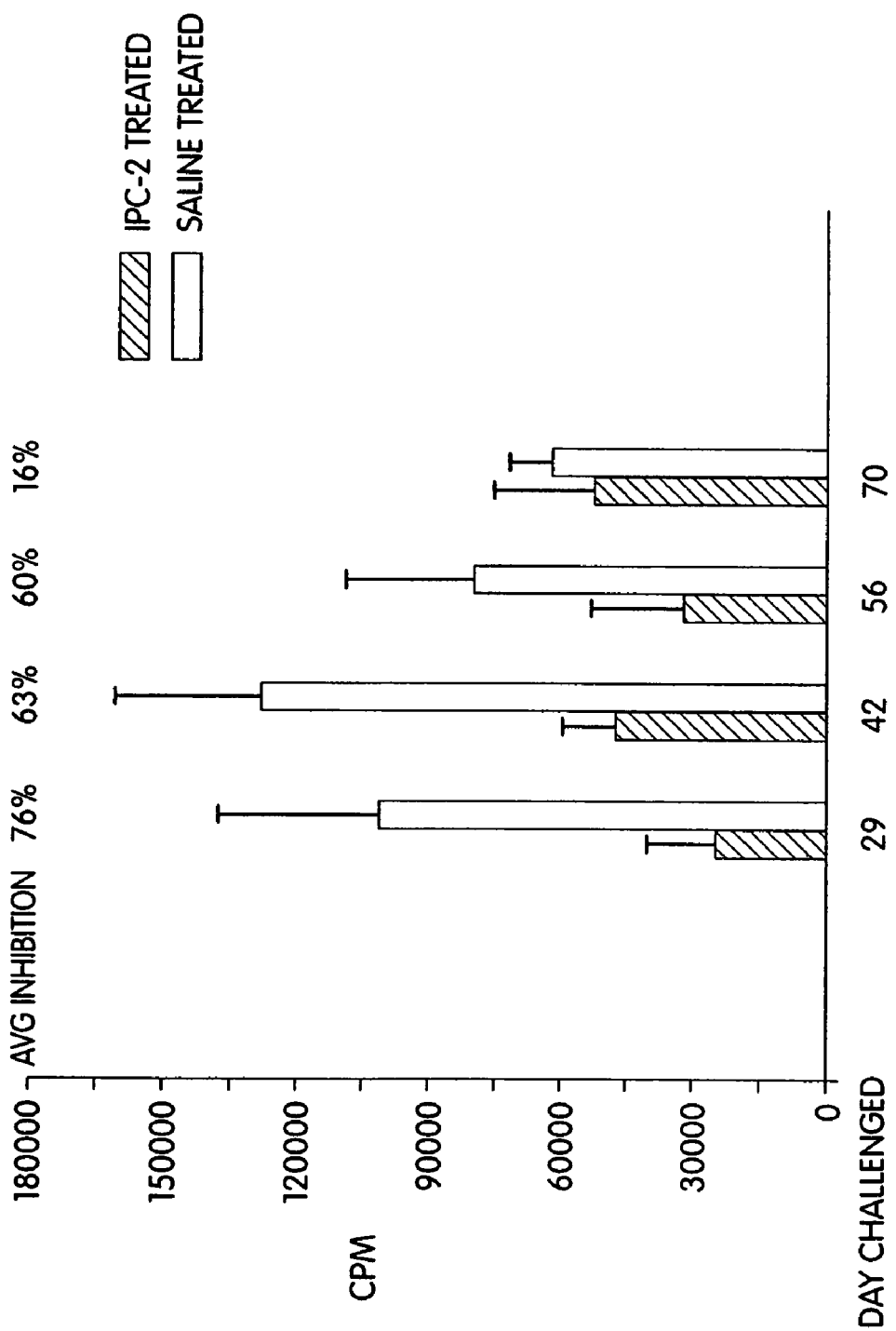
FIG. 25 is a graphic representation showing that the inhibitory effects of subcutaneous injection of Peptide Y on T cell function in primed mice are observable up to 56 days after the final injection of peptide Y.

FIG. 20 shows the summarized graphed results of eight individual cat allergic patients comparing histamine release following culture with various concentrations of affinity purified TRFP, peptide X and peptide Y. The graph shows the concentration of the various antigens in nMoles versus the percent total histamine released for each patient. The graph depicts the average percent release for each concentration point and the standard error of the mean are shown with error bars. Although only one reaction/patient is performed with PACM buffer alone it is represented as a line for comparison with antigen release levels.

The results are represented as percent total histamine released because of the great variability between patients in overall histamine levels. The source of this variability relates to the number of basophils per unit blood from patient to patient and the variation in quantity of histamine per basophil. There are only six (5-fold) concentration points for the TRFP peptide antigens emphasizing the higher end of the concentration curve. The TRFP concentrations are eight five-fold dilutions with three lower concentrations used for TRFP to get the full response range.

The histamine release profile shown in FIG. 21 demonstrates that TRFP, at all but the lowest concentration, gives a clear release signal. However, there is the appearance of a plateau of release at lower concentrations with increasing release at higher antigen concentrations. The typical histamine release profile with a single, purified allergen should theoretically show a bell-shaped curve with lower histamine released at higher concentrations due to lack of crosslinking (i.e., each IgE molecule bound to a cell surface receptor binds a separate allergen molecule). This was not the case in the current experiments with TRFP. There is no discernible histamine release to either peptide X or peptide Y.

EXAMPLE 18

Injecting Peptide X and Peptide Y Before Recombinant TRFP Chain 1 Challenge Prevents the Development of IgE Anti-Recombinant Chain 1 Antibodies To determine if injecting peptides affected the antibody response to protein, mice were injected subcutaneously according to the procedures described previously with 30 µg peptide X and peptide Y, followed five days later by either an additional 30 µg or 300 µg of peptide. All mice including a positive control group were injected five days later with recombinant chain 1 in adjuvant.

Mice injected with recombinant chain 1 in alum, made a significant IgE anti-recombinant chain 1 response which was detectable up to eight weeks later. In contrast, mice pre-injected with 30 µg followed by 300 µg of each peptide prior to immunization did not make an anti-recombinant chain 1 IgE response over this same period. Mice pre-injected with 30 µg followed by an additional 30 µg, however, did develop significant anti-recombinant chain 1 IgE titers.

These data suggest that pre-injecting peptides prior to immunization with protein on alum can lead to a long-lasting and dose-dependent inhibition of antibody formation.

EXAMPLE 19

Injecting Peptide Y Into Fel d I Primed Mice Results in a Long-Term Decrease in IL-2 Production To determine the effects of injecting peptides into mice with existing T and B responses to native Fel d I, mice were injected twice subcutaneously with peptide Y four months after priming with affinity purified native Fel d I. Subsequently, mice were injected with peptide Y in Complete Freund's Adjuvant (CFA) at different times after the final subcutaneous peptide Y injection Lymph node cells from mice injected with peptide Y subcutaneously up to fifty-six days earlier showed decreased IL-2 production compared to cells from control mice. At times greater than fifty-six days after subcutaneous injection, IL-2 production by lymph node cells from subcutaneous injected and positive control mice was comparable.

The experiment suggests that, in primed mice just as in naive mice, T cells may be inactivated for up to eight weeks after subcutaneous peptide injection, and that T cell responsiveness recovers after this time period.

EXAMPLE 20

Peptide Pre-Injection Results in Peptide-Specific Decreased IL-2 Responsiveness

To determine the specificity of unresponsiveness induced by peptides, mice which respond to both peptide Y and a peptide specific for a T cell epitope of the mite allergen, Der p II, peptide MI-05 were injected subcutaneously with peptide Y in saline. The animals were then challenged with peptide Y, MI-05 or a combination of peptide Y and MI-05 in CFA. In vitro responses seven days later indicated that subcutaneous injection of peptide Y decreased responsiveness to peptide Y but did not affect responses to MI-05. The findings suggest that only the T cell response to the peptide pre-injected subcutaneously is decreased.

EXAMPLE 21

Purified CD4+ T Cells Show Decreased Production of IL-2, IL-3 and IL-4 After Subcutaneous Injection of Peptide Y To determine which cells were actually rendered non-responsive by peptide pre-injection, T cell populations containing greater than 90% CD4+ cells were obtained by negative selection, using a cocktail of antibodies and magnetic beads, from the lymph nodes of both primed and peptide Y pre-injected mice. In the presence of normal splenic antigen presenting cells, CD4+ T cells from the pre-injected mice showed greater than 75% reduction in the production of the cytokines compared to control CD4+ cells. This result indicates that CD4+ cells are the cells affected by the pre-injection of peptide.

EXAMPLE 22

Biweekly Subcutaneous Administration of Peptide X and Peptide Y Does Not Induce Peptide Specific Antibody in Mice This animal model experiment was designed to simulate a human treatment protocol such as that described in Example 30. Mice were administered subcutaneous injections of 100 μg peptide/100 μl PBS on days 0, 14, 28 and 56. Mice were administered peptide X or peptide Y either alone or in combination. Sera were tested and shown to contain no antibodies specific for either peptide. There was no specific binding above background levels for IgG or IgE. The sera from animals injected with the peptides in CFA contained IgG antibodies to peptide X and peptide Y at dilutions down to 1/4500.

The results of this experiment are in contrast with those where rats were injected daily. Rats that were given daily subcutaneous injections for four weeks developed IgG antibodies specific to the peptides. No IgE specific antibodies developed in rats. The development of IgG antibodies may have been due to the inflammation from the repeated daily injections which resulted in a response to the peptides present at the inflamed site. In contrast, mice injected every 14 days with peptide X or peptide Y produced less irritation. No antibody production was noted in mice.

EXAMPLE 23

Peptide Y Monomer and Dimer are Equivalent for T Cell Responses

Peptide Y is composed primarily of peptide Y monomer with a a very slight amount of peptide Y dimer. Specifically, peptide Y dimer was produced and tested to determine whether the dimer maintained the ability to stimulate T cell proliferation. Samples of dimer tested contained less than 0.3% monomer. Both the peptide Y monomer and dimer were analyzed separately in the T cell proliferation assay. In an experiment conducted with peripheral blood lymphocytes from 15 patients with a history of cat allergy, peptide Y monomer and dimer were indistinguishable in stimulating T cell proliferation of Fel d I reactive human T cell lines.

In order to determine if there was a difference in the potency of the peptide forms, mice were given a tolerizing subcutaneous injection of 30 or 100 μg peptide Y dimer or monomer. In each instance, subsequent CFA challenge with the monomer form showed T cell tolerization indicating that the dimer form is equal to the monomer form in its ability to specifically render T cells non responsive.

EXAMPLE 24

Orally Induced T Cell Unresponsiveness to Peptides X and Y

Methods and Materials

1. Preparation of Protein and Peptides

A. Preparation from Natural Source

Native Fel d I protein was purified from an extract of house dust as described in Example 1

B. Chemical Synthesis

Two peptides (Peptide X (SEQ. ID. NO:17) and Peptide Y (SEQ. ID. NO:18) derived from the sequence of TRFP Chain 1 (SEQ. ID. NO:2) (Morgenstern et al. (1991) *Proc. Natl. Acad. Sci.* (*USA*) 88:9690-9694) were synthesized using conventional Merrifield solid-phase t-Boc or Fmoc chemistry. The peptides were purified by reverse-phase HPLC and examined by amino acid analysis. The peptides were lyophilized, resuspended in phosphate-buffered saline (PBS) prior to use and sterilized by gamma-irradiation (10,000 rads (1 rad=0.01 Gy)) or by passage through a 0.2-μm filter.

C. Recombinant Production

Recombinant TRFP 1 Chain 1 was expressed and purified as described in Example 2

2. Oral Induction of T Cell Non-Responsiveness

Protocol 1

Five groups of five age-matched B6CBAF$_1$ (H-2$^{bx\,a}$) 6- to 10-week old female mice (The Jackson Laboratory, Bar Harbor, Me.) were fed on days −7, −5 and −2 ("−" signifies days before antigenic challenge) with different concentrations of Peptide Y (500 μg, 250 μg, 125 μg and 50 μg) or PBS as a control. On day 0, the mice were challenged with 100 μg Peptide Y in complex Freund's adjuvant (CFA) injected subcutaneous (s.c.) at four sites at the base of the tail and in both thighs.

Protocol 2

Four groups of five age-matched Balb/c 6- to 10-week-old female mice (The Jackson Laboratory, Bar Harbor, Me.) were fed on days −7, −5 and −2 with 250 μg cleaved, purified, recombinant TRFP Chain 1 (rChain) (Groups 1 and 3) or with PBS (Groups 2 and 4). On day 0, the mice in Groups 1 and 2 were challenged with an intraperitoneal (i.p.) injection of 10 μg rChain 1 in alum, while the mice in Groups 3 and 4 were challenged on day 0 with an i.p. injection of 100 μg rChain 1 in CFA. The mice in Groups 1 and 2 were bled on days −8, −1, 14 and 21. On day 28 these groups were boosted with 10 μg rChain 1 in alum and bled on days 35 and 42. The mice in Groups 3 and 4 were bled on days −8, −1,14, 21, 28, 35 and 42. On day 28 these groups were boosted with 10 μg rChain 1 in alum and bled on days 35 and 42.

Protocol 3

Five groups of five age-matched Balb/c mice were fed on days −7, −5 and −2 with 250 μg rChain 1 (Groups 1 and 4), 750 μg rChain 1 (Group 2), or with PBS (Groups 3 and 5). On day 0, the mice in Groups 1-3 were challenged with a s.c. injection of 100 μg rChain 1 in CFA, while the mice in Groups 4 and 5 were not challenged. On day 12 the draining and mesenteric lymph nodes and spleens were removed for proliferation, IL-2, IL-4 and TGF-beta assays.

Protocol 4

Five groups of five age-matched B6CBAF$_1$ were fed on days −7, −5 and −2 with 250 µg each Peptide X and Peptide Y (Group 1), 250 µg rChain 1 (Group 2), or PBS (Group 3). On day 0, the mice were challenged with 100 µg rChain 1 in CFA injected subcutaneously. On day 12, the draining and mesenteric lymph nodes and spleens were removed for proliferation, IL-2 and IL-4 assays.

Protocol 5

Two groups of five age-matched Balb/c were fed on days −7, −5 and −2 with 250 µg rChain 1 (Group 1) or PBS (Group 2). On day 0, the mice were challenged with 10 µg rChain 1 on alum administered i.p., and on days 47 and 78, the mice were again challenged with 25 µg rChain 1 on alum administered i.p. The antibody response was measured by ELISA (see below).

4. Culture Conditions

The draining lymph nodes (i.e., inguinal, paraaortic and popliteal), the mesenteric lymph nodes, and the spleen were surgically removed from the animals 10-12 days after antigen challenge. Cells from these tissues were suspended by being forced through a stainless steel mesh with a glass pestle. The cells were washed twice in RPMI 1640 medium with a 1% fetal calf serum (FCS) before culture. All cells were cultured at 37° C. in 5% $CO_2$ in RPMI 1640 with 10% FCS (no. F4884, Sigma), 100 units of penicillin G per ml, 10 µg of streptomycin per ml, 10 mM glutamine, and 0.05 mM 2-mercaptoethanol. Cells were cultured in triplicate, 0.05 mM-mercaptoethanol. Cells were cultured in triplicate, 0.2 ml per well at $4 \times 10^6$ cells per ml, in 96-well plates. Supernatants were removed from the wells after 24 hours to test for the production of IL-2 or IL-3 and were frozen to kill any transferred cells or removed after 48 hours for testing IL-4 production. Separate triplicate wells were incubated for 96 hours for the proliferation assay. The supernatants were kept at 4° C. for several days to kill transferred cells.

5. Proliferation Assay

Lymph node of spleen cells were plated in a flat bottom 96-well plate ($4 \times 10^5$/well) in 100 µl medium. Peptide or recombinant protein or control solution (100 µl) is added to each well and the cells allowed to incubate for 1 day at 37° C. On day 2, the cultures were pulsed with [$^3$H] thymidine (1 µCi per well in 50 µl of medium; 1 Ci=37 GBq) for 4 to 6 hours, and on day 3, the plates were harvested with a 96-well harvester (Tomtec, Orange, Conn.) and counted on a Betaplate scintillation counter (Pharmacia, Upsaala Sweden).

6. IL-2 Assay

To measure IL-2, supernatants were tested after thawing for the ability to support the growth of an IL-2-dependent line such as CTLL-2 (University of California, Berkeley). The cell line was maintained by passage in 10% supernatant of Con A-stimulated (5 µg/ml) rat spleen cells. This cell line is dependent almost exclusively on IL-2 for growth and survival, proliferating only weakly to high doses of recombinant IL-4. Cells ($5 \times 10^3$ per well) in logarithmic-phase growth were washed twice and added in 50 µl of complete medium to 50 µl of warmed supernatants. After a 24 hour incubation, the cells were pulsed with [$^3$H] thymidine (1 µCi per well in 50 µl of medium; 1 Ci=37 GBq) for 4 to 6 hours and the plates were harvested with a 96-well harvester (Tomtec, Orange, Conn.) and counted on a Betaplate scintillation counter (Pharmacia, Upsaala Sweden).

All experimental cpm values were within the linear portion of the standard IL-2 titration curves run in parallel with each assay. The background values for IL-2 production by lymph node cells in cultures with medium alone were all less than 500 cpm. The plateau of thymidine incorporation at high levels of IL-2 standard in these assays was between 50,000 and 80,000 cpm.

7. IL-3 Assay

To measure IL-3, supernatants were tested after thawing for the ability to support the growth of an IL-3-dependent line such as DA-1 (Dr. J. Ihle, NCI-Frederick Cancer Research Facility). The cell line was maintained by passage in 10% supernatant of Con A-stimulated (5 µg/ml) rat spleen cells. Cells ($1 \times 10^4$/well) in logarithmic-phase growth were washed twice and added in 50 µl of complete medium to 50 µl of warmed supernatants. After a 48 hour incubation, the cells were pulsed with [$^3$H] thymidine (1 µCi per well in 50 µl of medium; 1 Ci=37 GBq) for 6 to 10 hours and the plates were harvested with a 96-well harvester (Tomtec, Orange, Conn.) and counted on a scintillation counter (Betaplate, Pharmacia, Upsaala, Sweden).

All experimental cpm values were within the linear portion of the standard IL-3 titration curves run in parallel with each assay. The background values for IL-3 production by lymph node cells in cultures with medium alone were all less than 500 cpm.

8. IL-4 Assay

Peptide-specific IL-4 production was measured by the ability of the supernatants to sustain cell division of a cell line that grows in response to IL-4, such as CT.4S cells (gift of W. Paul, National Institute of Allergy and Infectious Diseases). Incorporation of [$^3$H] thymidine was assessed as described above in the IL-2 assay.

9. Antibody Response Assay (ELISA)

For the IgG assay, affinity purified Fel d I or Peptide Y was coated onto Polysorp (Nunc) or Immulon II (Dynatech) 96-well plates, respectively, by incubation of 50 µl per well of 20 µg of Fel d I per ml or 20 µg of Peptide Y per ml in PBS overnight at 4° C. Subsequent incubations were for 1 hour at 37° C. The wells were washed with PBS containing 0.05% Tween 20 and blocked with 0.5% gelatin in PBS. Sera were diluted in PBS as noted in the individual assay and were incubated in triplicate on the washed plates. After incubation and washing, the bound mouse antibody was detected by incubation with biotinylated goat anti-mouse IgG (Southern Biotechnology Ass.). Streptavidin conjugated to horseradish peroxidase (Southern Biotechnology Associates) was added to detect antigen-bound biotinylated antibody complexes. 3,3',5,5'-Tetramethylbenzidine peroxidase substrate (Kirkegaard & Perry Labs) was used according to directions supplied, and resulting OD (450 nm) values were determined using an ELISA reader (Bio-Tek model 310, Winooski, Vt.). The serum titer is defined as the last dilution$^{-1}$ at which the OD value was twice the background of preimmune serum binding to the same antigen-specific binding of IgG1, IgG2a, IgG2b, IgG3, and IgM isotypes was similar to the IgG assay with the exception that biotinylated anti-immunoglobulin was used to detect the bound isotype. These assays employed biotinylated goat anti-IgG1, anti-IgG2a, anti-IgG2b, anti-IgG3, and anti-IgM (Southern Biotechnology Associates).

Antigen-bound IgE was detected similarly except using a biotinylated rat monoclonal antibody specific for mouse IgE (Baniyash et al. (1984) *Eur. J. Immunol.* 14:799-807). Biotinylated goat anti-rat immunoglobulin (Kirkegaard & Perry Labs) was used as an additional signal amplification step in the IgE ELISA.

Results

Figure 26:
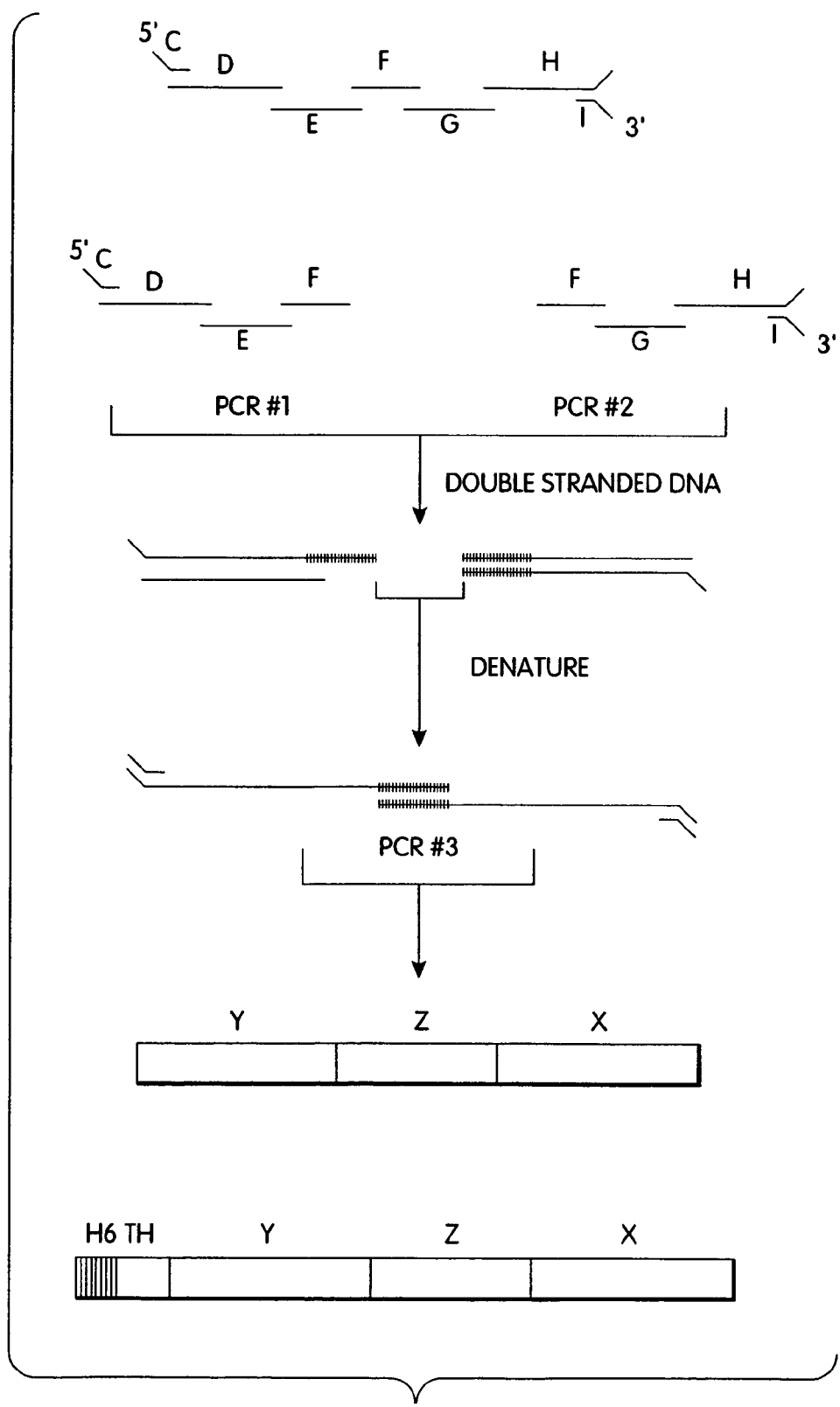
FIG. 26 is a schematic representation of the construction of a peptide YZX using polymeras chain reaction (PCR) techniques.
Figure 27:
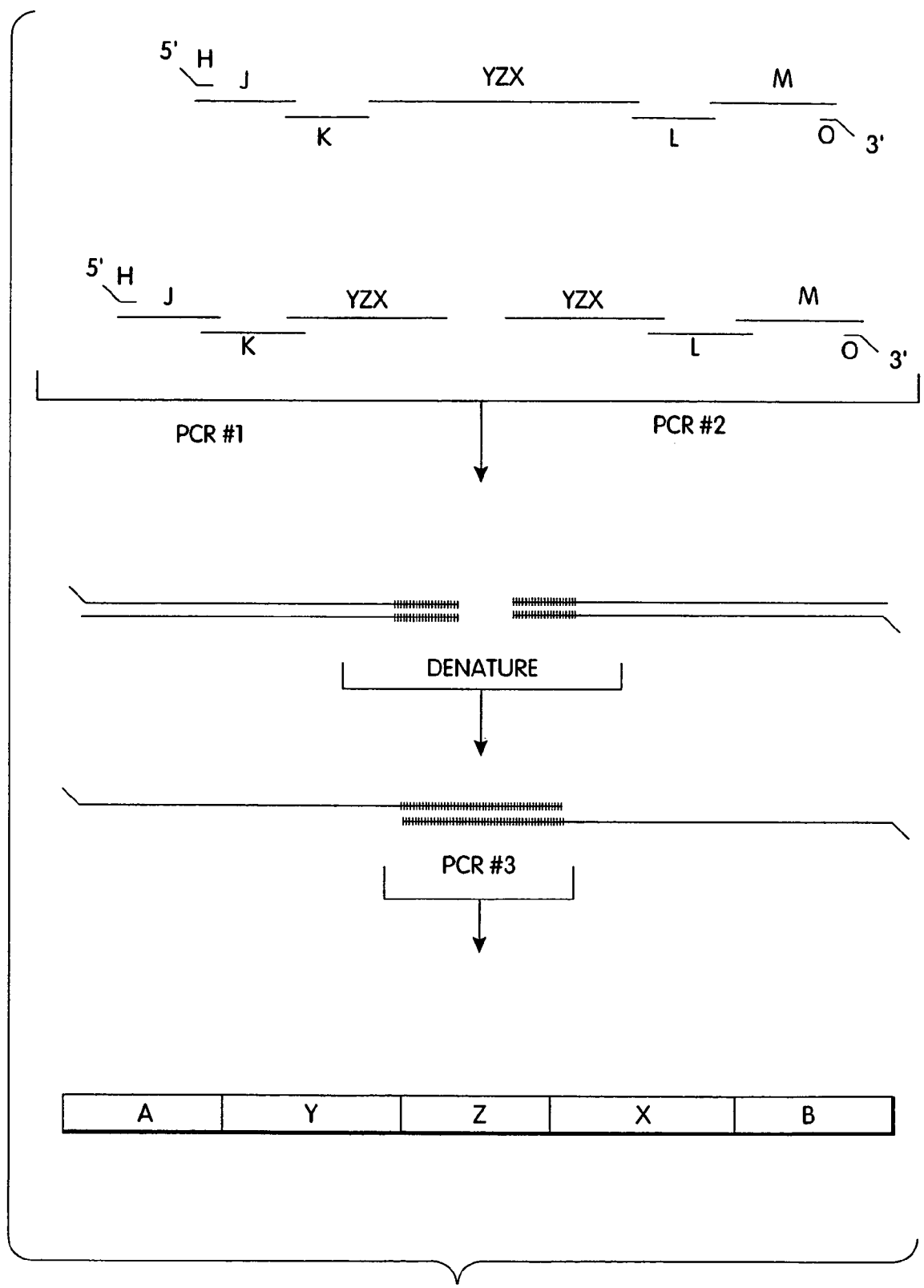
FIG. 27 is a schematic representation of the construction of a peptide AYZXB using PCR techniques.

To assess the ability of orally administered peptides derived from TRFP to effect T-cell responses, 5 groups of five B6CBAF mice were fed 7, 5, and again 2 days before challenge (−7, −5, −2) with different concentrations of Peptide Y in PBS or with PBS alone (see protocol 1). B6CBAF$_1$ mice were used because they have been found to generate a strong T-cell response to epitaps present in Peptide Y. The mice were then challenged on day 0 with Peptide Y in complete Freund's adjuvant (CFA). Cells from the draining and mesenteric lymph nodes and spleen were then cultured in the presence of Peptide Y. The peptide-specific T-cell response to Peptide Y was measured by an IL-2 assay as described above, and proliferation assay 10 days after challenge.

Proliferation of and production of IL-2 by draining and mesenteric lymph node cells were decreased in cells from the peptide-tolerized animals. Although no effect on spleen cell proliferation was seen (FIG. 24A), spleen cells were limited in their ability to produce IL-2 (FIG. 24B). Thus, the results of this experiment demonstrate that orally administered peptide can induce peptide-specific T-cell non-responsiveness.

To determine whether peptide-induced unresponsiveness could be demonstrated in animals already exposed to the antigen under conditions where antigen-primed T- and B-cell responses were present, antibody response was measured under different treatment conditions. Four groups of five Balb/c mice were fed on days −7, −5 and −2 with either 250 μg recombinant Chain 1 (rChain 1) or PBS. The treated mice were then challenged via i.p. injection on day 0 with 10 μg rChain 1 on alum (Groups 1 and 2) or with 100 μg rChain 1 in CFA (Groups 3 and 4). The mice in Groups 1 and 2 were challenged again on day 28 with rChain 1. All mice were bled on days −8, −1, 14, 21, 28, 35 and 42 (see protocol 2).

An ELISA indicated that oral administration of rChain 1 resulted in a depressed level of IgG response to rChain 1 up to 100 days after such treatment (data not shown). The use of CFA instead of alum in the challenge injection did not result in as great a tolerization effect. The IgE response to this treatment 92 days after challenge indicated that there was less IgE binding to rChain 1 in mice that had been treated orally with rChain 1, as compared to mice who were treated with only with PBS.

To determine whether optimal tolerization requires multiple or single oral doses of rChain 1, and whether subsequent challenge is required for the best response, five groups of five Balb/c mice were fed three times before challenge or one time before challenge with PBS or rChain 1. Alternatively, mice fed three times were not challenged (see protocol 3). On day 12, draining and mesenteric lymph node cells and spleen cells cultured and assayed for proliferation and IL-2 production. The results (data not shown) indicate that draining node response to at single oral treatment of 750 μg rChain 1 was more effective than was a regime of several doses of 250 μg rChain 1 administered before challenge.

In similar experiments, the tolerizing effects on the response to Peptide Y were found to be better than the tolerizing effects on the response to Peptide X (data not shown). It is likely that this result was obtained because Balb/c mice are known not to respond well to Peptide X. When mesenteric lymph node cells were cultured with rChain 1, Peptide X, and Peptide Y, there was a detectable tolerizing effect on the production of IL-2 (data not shown). Spleen cell response was moderately decreased when assayed for the response to rChain 1 and peptide Y. As expected, spleen cell response was not changed when assayed for the response to peptide X.

To determine whether tolerization with a combination of Peptides X and Y decreases the response to the larger polypeptide subunit rChain 1, three groups of five $B6CBAF_1$ mice were fed with either a combination of Peptides X and Y, rChain 1, or PBS, followed by challenge with rChain 1 in CFA via subcutaneous injection (see protocol 4). On day 12, the lymph nodes and spleens were harvested and cultured in the presence of Peptide X, Peptide Y, or rChain 1. The results (data not shown) indicate that the administration of a combination of both Peptide X and Peptide Y results in a decrease in proliferative response of draining lymph node cells cultured in the presence of rChain 1, Peptide X, or Peptide Y, equal to that seen when whole rChain 1 is administered. A greater decrease is seen in the production of IL-2 by draining lymph node cells cultured in the presence of rChain 1. Culturing of cells in the presence of Peptide X had little effect on the production of IL-2 in this system, while culturing in the presence of Peptide Y showed an effect less than that seen in the presence of rChain 1 (data not shown). Similar results were seen in IL-3 assays on draining lymph node cells (data not shown). No tolerizing effects were seen in similarly treated mesenteric lymph node cells by IL-3 assays (data not shown) and IL-4 assays (data not shown).

To determine whether oral tolerization with rChain 1 decreases specific IgG and IgE antibody response after repeated challenge with rChain 1, two groups of five Balb/c mice were fed either rChain 1 or PBS on days −7, −5 and −2. The mice were challenged with rChain 1 via i.p. injection on day 0 or on days 0, 47 and 78 (see protocol 5). The results (data not shown) indicate that the oral administration of rChain 1 decreases specific IgG and IgE responses, respectively, after repeated challenge with rChain 1 in alum, and demonstrate that the oral administration of peptides derived from TRFP Chain 1 decreases the T-cell response to challenge with Chain 1.

EXAMPLE 25

Construction and Expression of Peptides Comprising Two or More Regions of TRFP PCR methods (Polymerase Chain Reaction) using synthetic oligonucleotides were used to construct DNAs encoding the sequences of peptides X, Y, and Z. With the aim of enhancing expression in *E. coli*, the codons in the oligonucleotides were selected from a table of those prevalent in highly expressed *E. coli* proteins. Sharp, P. M., et al., *Nucl. Acids Res.* 16:8207 (1988). The oligonucleotides and PCR procedures used to construct the peptides are described in detail below.

Oligonucleotides were designed with *E. coli* preferred codons as schematically represented in FIGS. 26 and 27. These oligonucleotides (C (SEQ. ID. NOS: 61 and 62), D (SEQ. ID. NOS: 63 and 64), E (SEQ. ID. NOS: 65 and 66), F (SEQ. ID. NOS: 67 and 68), G (SEQ. ID. NOS: 69 and 70), H (SEQ. ID. NOS: 71 and 72), I (SEQ. ID. NOS: 73 and 74), J (SEQ. ID. NOS 75 and 76), K (SEQ. ID. NOS: 77 and 78), L (SEQ. ID. NOS: 79 and 80), M (SEQ. ID. NOS: 81 an 82), N (SEQ. ID. NOS: 83 and 84) and O (SEQ. ID. NOS: 85 and 86) shown in FIG. 28), were amplified using a Perkin Elmer/Cetus GeneAmp kit, in two separate PCR reactions (PCR#1 and PCR#2, respectively wherein PCR #1 resulted in the synthesis of the 5' portion of the DNA molecule encoding the peptide and PCR #2 resulted in the synthesis of the 3' portion of the DNA molecule encoding the peptide). This approach was taken due to the presence of a sequence (KALPV; (amino acid residues 1-5 of (SEQ. ID. NO: 18)) in both peptide X and peptide Y that was found to interfere in the proper PCR generation of YZX when a single PCR reaction was performed with oligonucleotides (C-I). In producing peptide AYZXB, as shown in FIG. 27, the oligonucleotides used in PCR #1 were N (SEQ. ID. NOS: 83 and 84), J (SEQ. ID. NOS: 75 and 76), K (SEQ. ID. NOS: 77 and 78), and C-I and the oligonucleotides used in PCR #2 were C-I and L (SEQ. ID. NOS: 79 and 80), M (SEQ. ID. NOS: 81 and 82), O (SEQ. ID. NOS: 85 and 86). In producing peptide YZX, as shown in FIG. 27, the oligonucleotides used in PCR #1 were C (SEQ. ID. NOS: 61 and 62), D (SEQ. ID. NOS: 63 and 64) E (SEQ. ID. NOS: 65 and 66) and F (SEQ. ID. NOS: 67 and 68), whereas the oligonucleotides used in PCR #2 were F (SEQ. ID. NOS: 67 and 68), G (SEQ. ID. NOS: 69 and 70), H (SEQ. ID. NOS: 71 and 72) and I (SEQ. ID. NOS: 73 and 74). Each reaction mixture (10 μg) generated the 5' half and 3' half respectively, of the intended YZX structure (FIG. 26). These PCR mixtures, after the addition of Taq polymerase, were subjected to the following program with cycles of denaturation, annealing and polymerization:

| STEP # | TEMPERATURE | TIME |
|---|---|---|
| 1 | 94° C. | 1 MINUTE |
| 2 | 50° C. | 1.5 MINUTES |
| 3 | 75° C. | 2 MINUTES |
| 4 | REPEAT STEPS 1-3 (4 TIMES) | |
| 5 | 94° C. | 1 MINUTE |
| 6 | 60° C. | 1.5 MINUTE |
| 7 | 75° C. | 2 MINUTES |
| 8 | REPEAT STEPS 5-7 (20 TIMES) | |
| 9 | HOLD AT 4° C. | |

After completion of the PCR#1 and PCR#2 reactions in the construction of the YZX structure, aliquots from each (100 p moles of the 10 μg total reaction mixture; 1/100 volume) were added to a third PCR reaction mixture containing a set of 5' and 3' primers (100 p mole of primers C and I). A third PCR reaction (PCR #3) was performed utilizing this third PCR reaction mixture as previously described for PCR reactions #1 and #2 except that the annealing temperature in Step 6 was raised to 65° C. The completion of PCR#3 produced the DNA encoding peptide YZX. The PCR#3 reaction method is similar to that described in Horton, R. M., et al. *Gene* 77:61 (1989). The whole reaction mixture used in PCR#3 was fractionated on a 2% agarose gel and the appropriate sized band (230 bp) was electroeluted from the gel slice and precipitated. The isolated DNA encoding peptide YZX was subjected to another PCR reaction using excess 5' and 3' amplification primers (C and I). This final product was digested with the restriction enzymes BamH I and then cloned into the vector pET11d under the transcriptional control of the phage T7 gn 10 lac 0 fusion promoter. Studier, F. W., et al. *Methods in Enzymol.* 185:60 (1990).

A polylinker encoding six sequential histidines, $(CAC)_6$, was cloned in-frame onto the 5' end of the DNA encoding peptide YZX (FIG. 29). The six histidine ($H_6$ or His 6) leader sequence allowed purification of the expressed peptide using QIAGEN NTA-Agarose (Diagen Gmbh, Dusseldorf, Germany), a $Ni^{2+}$ chelating support. Hochuli, E., et al., *BioTechnology* 6:1321 (1988). DNA encoding site-specific enzymatic cleavage sites (e.g., Thrombin, Factor $X_a$, etc) can be inserted using PCR methods between the polyhistidine encoding ($H_6$) sequence and the DNA encoding the peptide backbone. In the case of peptide YZX, a thrombin recognition site (LVPRGS) (SEQ. ID. NO: 87) was inserted. Uhlen, M., and Moks, T. *Methods in Enzymol.* 185:129 (1990), Chang, J.-Y. *Eur. J. Biochem.* 151:217 (1985).

A similar procedure to that described above to construct DNA encoding the peptide YZX was used to construct DNA encoding the peptides XYZ and ZYX. In addition, other peptides containing T cell epitopes can be added to an existing backbone structure such as YZX (as produced above) as was the case with the construction of peptide AYZXB (see FIGS. 26 and 27). Alternatively, peptides containing T cell epitopes can be produced without the use of an existing backbone using methods outlined herein. To produce peptide AYZXB, oligonucleotide primers (J-M) with overlapping regions to each end of peptide YZX and a 5' and 3' amplification primer (N and O) were produced. (As shown in FIG. 27, the darkened part of the molecule is the overlapping sequence). PCR reactions were performed as described above. The resulting AYZXB fragment was isolated and subcloned into the pET 11DH$_6$ TH vector.

Figure 30:
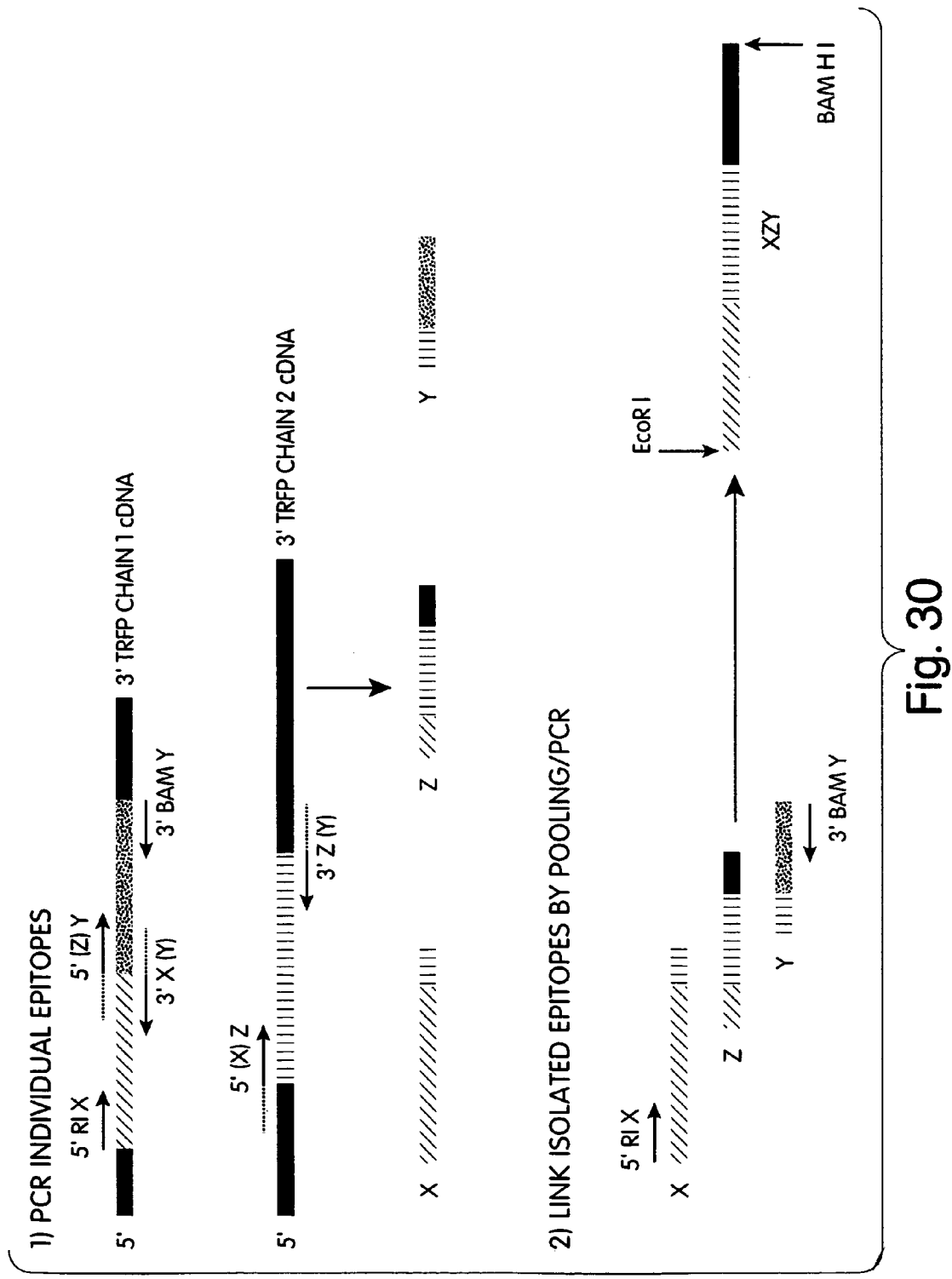
FIG. 30 is a schematic representation of the construction of a peptide YZX using PCR techniques with cDNA isolated from TRFP as a template.
Figure 32:
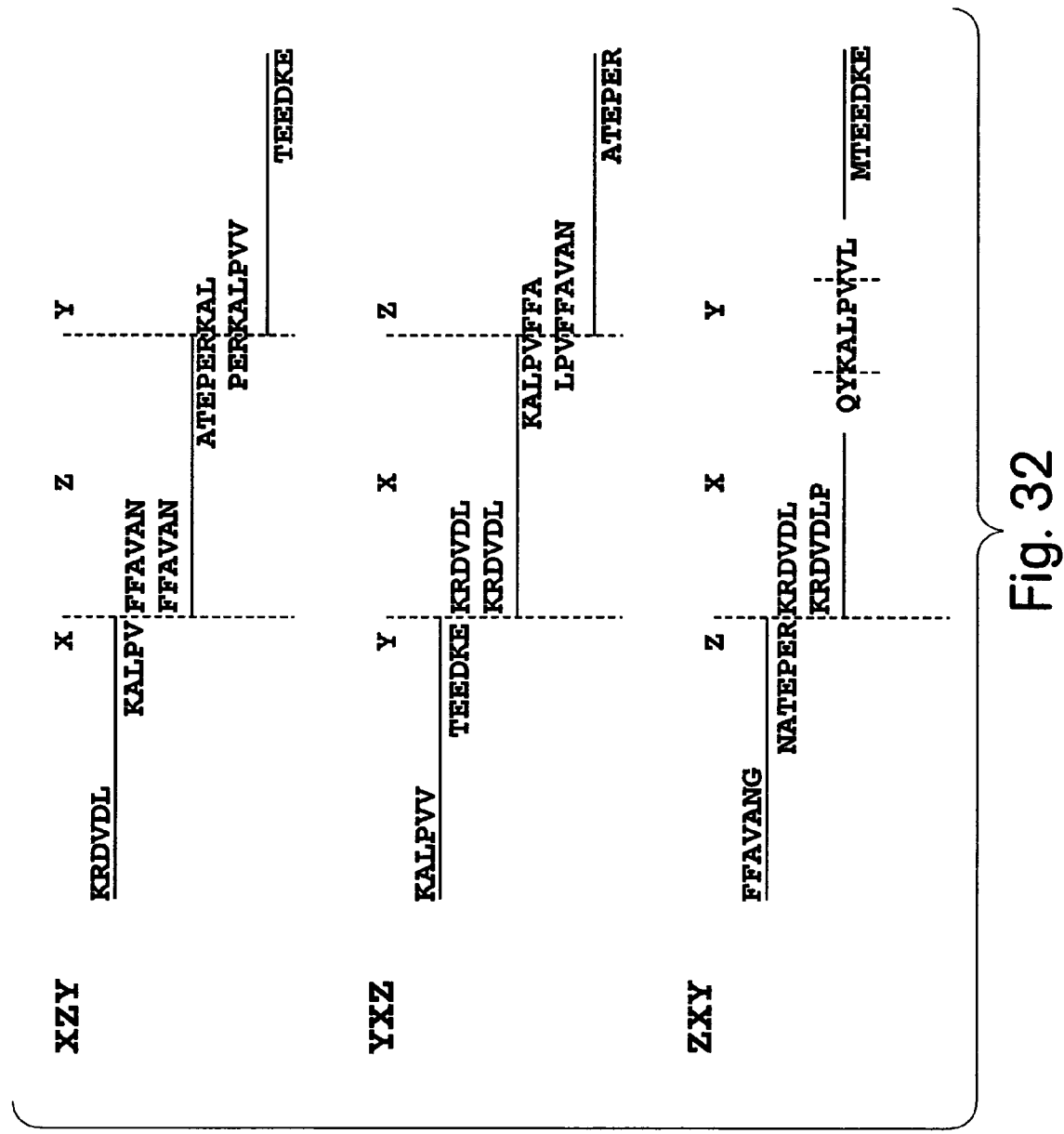
FIG. 32 is a graphic depiction of the amino acid sequence of the individual primers use to construct the peptides XZY, YXZ and ZXY.
Figure 33:
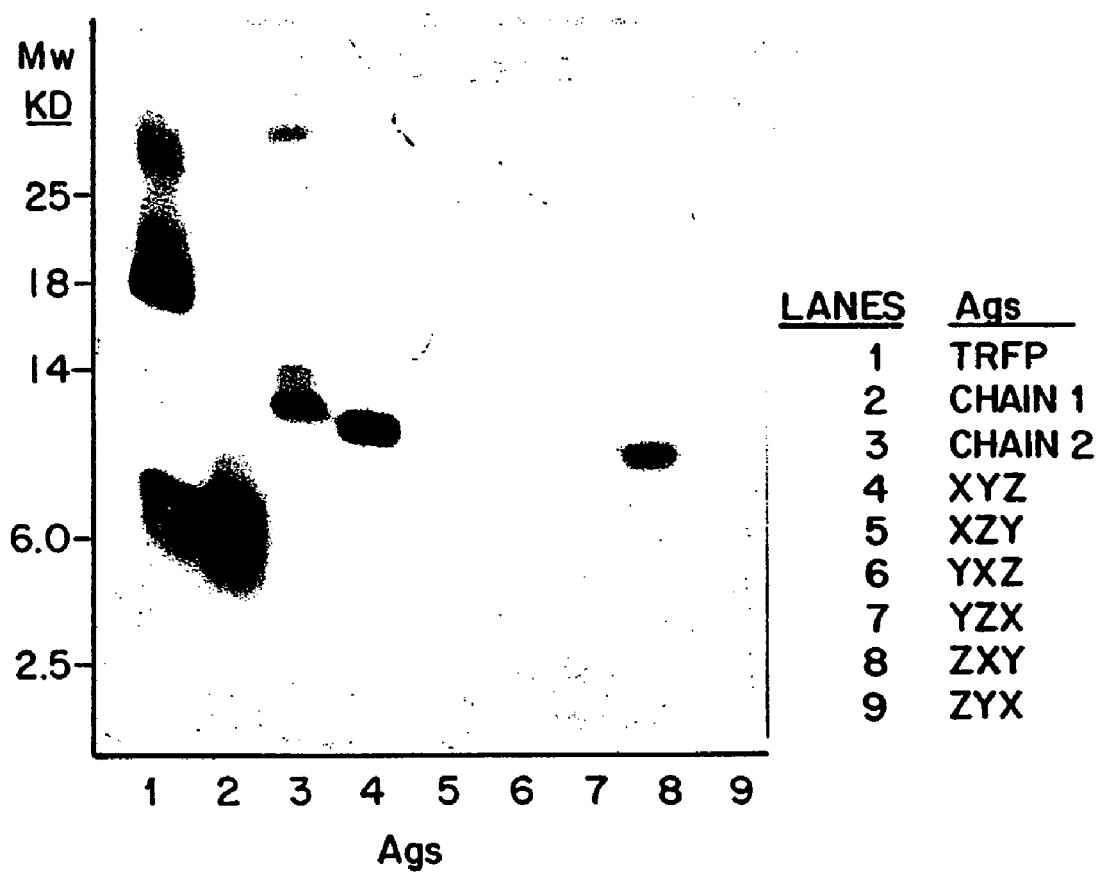
FIG. 33 is a representation of the results of SDS/PAGE Western immunoblot analysis detecting the binding of human IgE obtained from a cat allergic individual to various protein samples, including peptides XYZ, XZY, YXZ, YZX, ZXY and ZYX.

An alternative procedure was used to construct the DNA encoding peptides XZY, YXZ, and ZXY. Each of the DNA constructs encoding peptides XZY, YXZ and ZXY were ligated at the codon encoding the most N-terminal amino acid of the peptide with DNA encoding the leader sequence MGH-HHHHHEF ((SEQ. ID. NO: 88) where amino acids EF are encoded by the Eco RI restriction site GAATTC (SEQ. ID. NO: 89)). DNA segments encoding the three peptides were assembled via consecutive PCR essentially as described by Horton et al., (1989) *Gene* 77: 61-68. The DNA segments encoding peptides X, Y, and Z (shown in FIG. 17) were amplified from the Fel d I cDNAs described in Morgenstern et al., (1991) *Proc. Natl. Acad. Sci. U.S.A.* 88: 9690-9694. As shown in FIG. 30, which shows as a specific example the construction of the peptide XZY coding sequence, oligonucleotide primers were synthesized with a DNA sequence that would not only amplify a specific DNA segment encoding peptide X, Y or Z, but would also covalently link a small segment (9-18 base pairs) of the DNA segment encoding the adjacent peptide X, Y, or Z. PCR was performed using Vent™ polymerase according to New England Biolabs' instructions with an amplification program of 30×[94° C. 1 min./60° C. 1 min. 30 sec./72° C. 1 min.]. The primers used for PCR amplifications are shown in FIG. 32. Individual peptide encoding/linker DNA fragments from PCR amplifications were purified by preparative gel electrophoresis in 3% (wt./vol.) NuSieve (FMC) agarose. These individual PCR fragments were then linked in a second PCR reaction to form a DNA construct encoding XZY as shown in FIGS. 30 and 32. In order to link these PCR fragments, 3% NuSieve gel slices containing the initial PCR products were melted at 70° C., and 1 μl of each were added to a Vent™ PCR polymerase reaction which employed the 5' RI ($NH_2$-terminal) and 3' Bam (COOH-terminal) primers.

Because of the restriction sites present in the expression vector, pET11d (Studier et al, 1990), all extreme 5' primers had EcoR I encoding sites [GAATTC (SEQ. ID. NO: 89] in frame with the DNA encoding the $NH_2$-terminal amino acids of the particular, while the ends of the extreme 3' primers had BamH I encoding sites [GGATCC (SEQ. ID. NO: 90)]. DNA constructs encoding peptides XZY, YXZ, and ZXY produced from the secondary PCR were EcoR I/BamH I digested and electrophoresed through a 0.5 (wt./vol.) SeaPlaque (FMC) agarose gel. Gel slices containing the DNA constructs were melted at 70° C. and added to a ligation reaction with EcoR I/BamH I digested Bluescript KS plasmid (Stratagene). The ligation was transformed into competent XL-I Blue bacteria (Stratagene), and recombinant plasmids with inserts identified by diagnostic restriction digests after isolation using Qiatop kit (Diagen GmbH). The sequence of inserts was verified by dideoxy chain-termination sequence analysis using a Sequenase II kit (United States Biochemicals).

Bluescript KS plasmids harboring DNA constructs encoding peptides XZY, YXZ and ZXY inserts with correct nucleotide sequence were EcoR I/BamH I digested and the DNA constructs isolated from a 0.6% SeaPlaque gel for subcloning into the expression vector pET11d in frame with the DNA encoding the $NH_2$-terminal leader MGHHHHHHEF (SEQ. ID. NO: 88) as mentioned above. The constructs were subcloned into the EcoR I/BamH I digested pET11d $His_6$ Amb a I. 1 HR. This ligation served to exchange the DNA construct for an insert, in this case the cDNA of the major ragweed allergen, Amb a I.1 (Rafnar et al., (1991) *J. Biol. Chem.* 226:1229-1236). pET11d His Amb a I.1 DHR was derived from pET11d in two steps. First pET11d was Eco RI/HinD III digested, blunted with Klenow fragment of *E. coli* DNA polymerase, and ligated back to itself to create pET11d DHR: a pET11d plasmid lacking Hind III and EcoR I sites. Then pET11d $His_6$Amb a I.1 DHR was formed by excising the $H_6$Amb aI.1 cassette from the expression vector pET11d $His_6$Amb aI.1 as an Nco I/BamH I fragment and ligating it into Nco I/BamH I digested pET11d DHR. Recombinant plasmids were identified by diagnostic restriction digests after isolation via a Qiatip kit, and positive plasmids transformed into competent BL21 [DE3] bacteria for expression. BL21 [DE3] contains a recombinant phage 1 lysogen, DE3, with a phage T7 RNA polymerase gene under the transcriptional control of the lac UV5 promoter. T7 RNA polymerase gene expression is induced by the addition of IPTG, which in turn leads to high level expression of the recombinant gene subcloned 3' of the pET vector's T7 gn 10 lac 0 fusion promoter.

PCR-derived DNA fragments encoding ($H_6$) fusions of mature chains 1 and 2 of TRFP subcloned into pSEM (U.S. Ser. No. 662,276 filed Feb. 28, 1991) were excised and ligated into pET11d. This was achieved by attaching Bcl linkers to the Pst I sites at the 3' ends of the two chains, Nco I digesting at the 5' end of the chains and inserting the 5' Nco I/3' Bcl I fragment into 5'Nco 1/3'BamH I digested pET11d.

The recombinant peptide chains 1 and 2 of TRFP as well as the peptides XYZ, XZY, YZX, ZYX, ZXY and YXZ were expressed in *E. coli* and purified essentially as outlined below. BL21 DE3 host bacteria harboring the pET11d expression DNA constructs were freshly streaked onto a BHI agar plate (3.7% wt./vol. Difco Brain Heart Infusion; 1.5% wt./vol. Difco agar) supplemented with 200 µg/ml ampicillin and incubated overnight at 37° C. A single colony was inoculated into a 2 ml of 200 µg/ml ampicillin/BHI media (3.7% wt./vol. Difco Brain Heart Infusion) and shaken at 300 rpm at 37° C. until turbid but not saturated. The 2 ml culture was then added to 100 ml of 200 µg/ml ampicillin/BHI media, shaken at 300 rpm at 37° C. until turbid but not saturated, at which point the culture was divided into 18×250 ml (4.5 liters) of 200 µg/ml ampicillin/BHI media and shaken at 300 rpm at 37° C. When the $OD_{595}$ of the culture reached 1.0, expression of the recombinant peptides as $(His)_6$ fusion peptides was induced by the addition of IPTG to 400 µM, and allowed to continue for two hours.

Bacteria were harvested by centrifugation at 10,000×g for 15 minutes, and resuspended in $1/50^{th}$ volume 6 M guanidine HCl, 100 mM 2-mercaptoethanol, 100 mM $NaPO_4$, 10 mM Tris at pH 8.0. Recombinant chain 1 and chain 2 and peptides (recombinant peptides) were extracted by vigorous shaking of the resuspended bacteria for 1 hour at 25° C. This suspension was subjected to centrifugation at 15,000×g, the supernatant removed, adjusted to pH 8.0 with 10 N NaOH, and applied to an NTA agarose column that had been equilibrated in 6 M guanidine HCl, 100 mM $NaPO_4$, 10 mM Tris at pH 8.0 until the $OD_{280}$ of the effluent reached background. The column buffer was then switched to 8 M urea, 100 mM $NaPO_4$, 10 mM Tris at pH 8.0. After equilibration, a more stringent wash was performed in 8 M urea 100 mM NaOAc, 10 mM Tris pH 6.3 until the $OD_{280}$ of the effluent reached background. Each recombinant peptide (as an $His_6$ fusion) was then eluted in 8M urea 100 mM NaOAc, 10 mM Tris at pH 4.5 and collected in aliquots whose $OD_{280}$ profile was monitored. The peptide peak was dialyzed 3 times into 500 volumes of PBS (Phosphate Buffered Saline) for analysis. Yield ranged from 2 to 25 mg of recombinant peptide ($His_6$) fusion per liter with purity (as determined by densitometric scanning of SDS polyacrylamide gels) generally exceeding 90%.

The recombinant peptides (TRFP chain 1, TRFP chain 2, XYZ, YZX and ZYX) outlined above all possess an N-terminal sequence added as an aid to purification and expression (e.g., MGHHHHHHLVPRGS-(SEQ. ID. NO: 76)). This irrelevant N-terminal sequence can be removed by proteolytic digestion since the sequence contains a thrombin recognition site (LVPRGS (SEQ. ID. NO: 8,) inserted between the polyhistidine sequence and the sequence. (See FIG. 29, the arrow indicates the thrombin cleavage site.) Thrombin was used to cleave the irrelevant sequence leaving only two extra amino acid residues, GS, on the N-terminus of the TRFP chains 1 and 2 and the peptides XYZ, YZX and ZYX (Chang, J.-Y. *Eur. Biochem.* 151:217-224 (1985)). Efficient cleavage of the fusion protein can be achieved by using a protein to thrombin ratio of 1000 to 1 for 2 hours at 25° C. The cleavage and purification scheme used to construct peptide YZX is outlined below:

1) peptide MGHHHHHHLVPRGS-YZX
2) Dialyze into PBS, pH 8.0
3) Thrombin cleavage
   peptide: thrombin=1000:1
   25° C., 2 hours
4) Reduction with 100 mM dithiothreitol
   in 5M guanidine HCL
   37° C., 30 minutes
5) $C_4$ Reverse phase HPLC, pH 2.0
6) Lyophilization Analytical reverse-phase HPLC was performed on a VYDAC 214 TP54 column with a 42 ml bed volume. The column was loaded with 340 µg of peptide YZX. Semi-preparative HPLC was performed using a VYDAC 214 TP 1022 column with a 95 ml bed volume loaded with 90 mg of protein. The gradient started with 0% to 30% acetonitrile containing 0.1% trifluoroacetic acid over the first 10 minutes followed by 30% to 43% acetonitrile over 15 minutes. The mobile phase was then held at 43% acetonitrile for 10 minutes. The purified peptide YZX eluted at 43% acetonitrile. The cleavage and purification were monitored by SDS-PAGE. The identification and purity of the peptide YZX was determined by protein sequence analysis using an Applied Biosystem Inc. Protein Sequenator Model 477A.

EXAMPLE 26

Direct Binding Assay of IgE to TRFP Proteins and Peptides Comprising Two or More Regions of TRFP Western immunoblot analysis of the peptides produced in above was performed. The concentration of all protein samples (e.g., TRFP, recombinant chain 1 of TRFP, recombinant chain 2 of TRFP, peptide XYZ, peptide XZY, peptide YXZ, peptide YZX, peptide ZXY and peptide ZYX) for gel electrophoresis was determined by the BCA method (Pierce Co.). All protein samples were loaded on the gel at 5 µg/lane except TRFP at 10 µg/lane. Protein separation was carried out on a 15% acrylamide gel, and transfer was performed by electroblotting at 1.5 Amps for 1.5 hours onto nitrocellulose paper (Schleicher and Schuell, 0.1 microns) in a Hoeffer apparatus according to the protocol of Towbin, H., T. Stachlin, and J. Gordon, *PNAS* 76:4350 (1979). Proteins were rinsed in blot solution (25 mM Tris-HCl 7.5, 0.171 M NaCl and 0.5 ml/liter Tween 20). The blot was then blocked for one hour in blocking solution (1% milk in blot solution). Plasma from patient #417, used as a primary antibody source, was diluted in blocking solution to 10% and preabsorbed for 1.5 hours with unused nitrocellulose (2 cm×15 cm). The prepared human plasma was then incubated overnight on an orbital shaker with the protein blot section of interest. Following the first antibody incubation the blot section was washed three times, each wash involved a fifteen minute incubation in blot solution. The second antibody, specific for human IgE (biotinylated goat anti-human IgE, KPL Inc.), was diluted 1:2500 in blot solution and the incubation proceeded for two hours. Excess second antibody was subsequently removed by three 15 minute incubations with blot solution. $^{125}$I Iodinated streptavidin (Amersham) was diluted 1:2500 in blot solution and incubated with blots for 1 hour, at 2 µCi in a 50 ml incubation volume. Blot sections were then washed with blot solution until the detectable radioactivity in the waste solution decreased to background levels. The blot section was then wrapped in saran wrap and exposed to film overnight with a cronex intensifying screen at −80° C. The IgE binding pattern shown in FIG. 34 demonstrates reactivity to affinity purified TRFP (lane 1) chain 1, 6 KD in molecular weight and chain 2, ≧16 KD. The recombinant chain 1 shows strong IgE binding (lane 2) while recombinant chain 2 reactivity is reduced compared to chain 1 (lane 3). The peptides that show IgE binding are peptides XYZ and ZXY (lanes 4 and 8 respectively). All other peptides are negative for IgE binding by this method of analysis.

Specific binding of IgE to peptides was also demonstrated in ELISA assays. Corning assay plates (#25882-96) were coated with 10 µg/ml of each coating antigen (i.e., TRFP, chain 1 (recombinant chain 1 of TRFP), chain 2 (recombinant chain 2 of TRFP), peptide XYZ, peptide XZY, peptide YXZ, peptide YZX, peptide ZXY and peptide ZYX) listed in FIG. 34 at 50 µl/well and incubated overnight at 4° C. The coating antigens were removed and the wells were blocked with 0.5% gelatin in PBS, 200 µl/well for 2 hours at room temperature. Plasma from patient #669 was serially diluted with PBS-Tween 20 (PBS with 0.05% nonionic detergent Tween-20 Sigma, St. Louis Mo.) and 100 µl/well was added and incubated overnight at 4° C. (plasma dilutions are tested in duplicate). The second antibody (biotinylated goat anti-Human IgE, 1:1000, Kirkegaard & Perry Laboratories Inc. Gaithersburg, Md.), was added at 100 µl/well for one hour at room temperature. This solution was removed and streptavidin-HRPO, 1:10,000 (Southern Biotechnology Associates, Inc., Birmingham, Ala.) was then added at 100 µl/well for one hour at room temperature (all wells were washed three times with PBS-Tween between each incubation step). TMB Membrane Peroxidase Substrate system (Kirkegaard & Perry Laboratories) was freshly mixed, and added at 100 µl/well. The color was allowed to develop for 2-5 minutes. The reaction was stopped by the addition of 100 µl/well of 1M phosphoric acid. Plates were read on a Microplate EL 310 Autoreader (Biotek Instruments, Winooski, Vt.) with a 450 nm filter. The absorbance levels of duplicate wells were averaged. The graphed results (log of the dilution vs absorbance) of the ELISA assays are shown in FIG. 34.

Figure 34:
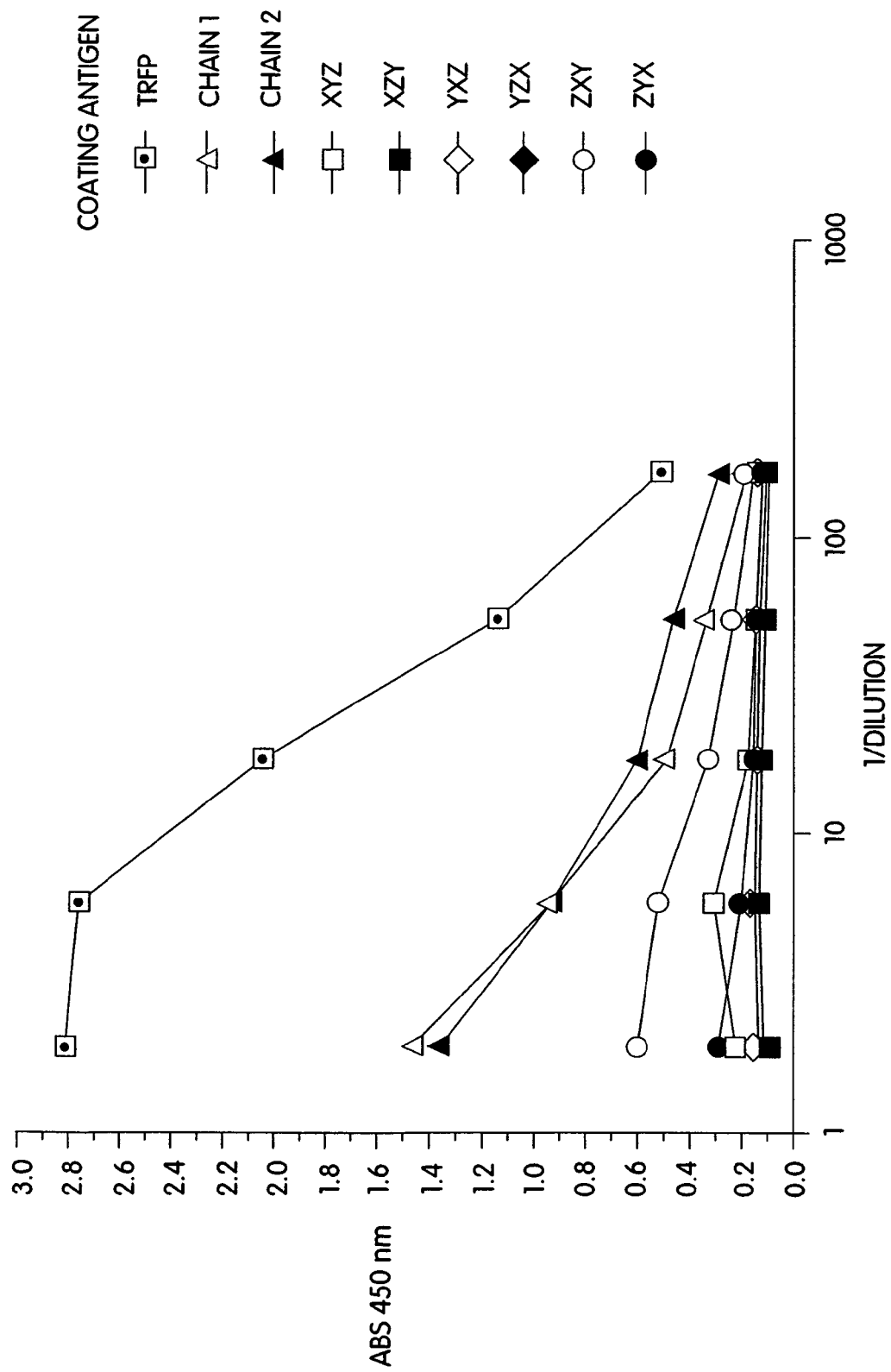
FIG. 34 is a graphic representation of the results of ELISA analysis illustrating the binding of human IgE obtained from a cat allergic individual to various protein samples, including peptides XYZ, XZY, YXZ, YZX, ZXY, and ZYX.

The results of the ELISA shown in FIG. 34 demonstrate a high level of IgE binding to TRFP with somewhat lower binding to recombinant TRFP chain 1 (chain 1) and chain 2 (chain 2). The two recombinant chains demonstrate equivalent binding with this particular patient's IgE. Only the peptide ZXY shows clear reactivity with IgE. The binding of the other peptides is at or near the background level with a slight signal from peptide XYZ. To demonstrate that peptides were present in equal amounts in both the ELISA and Western assay, anti-peptide antisera was used as a positive control and it gave fairly equivalent signals for all lanes and wells with peptides.

EXAMPLE 27

Figure 35A:
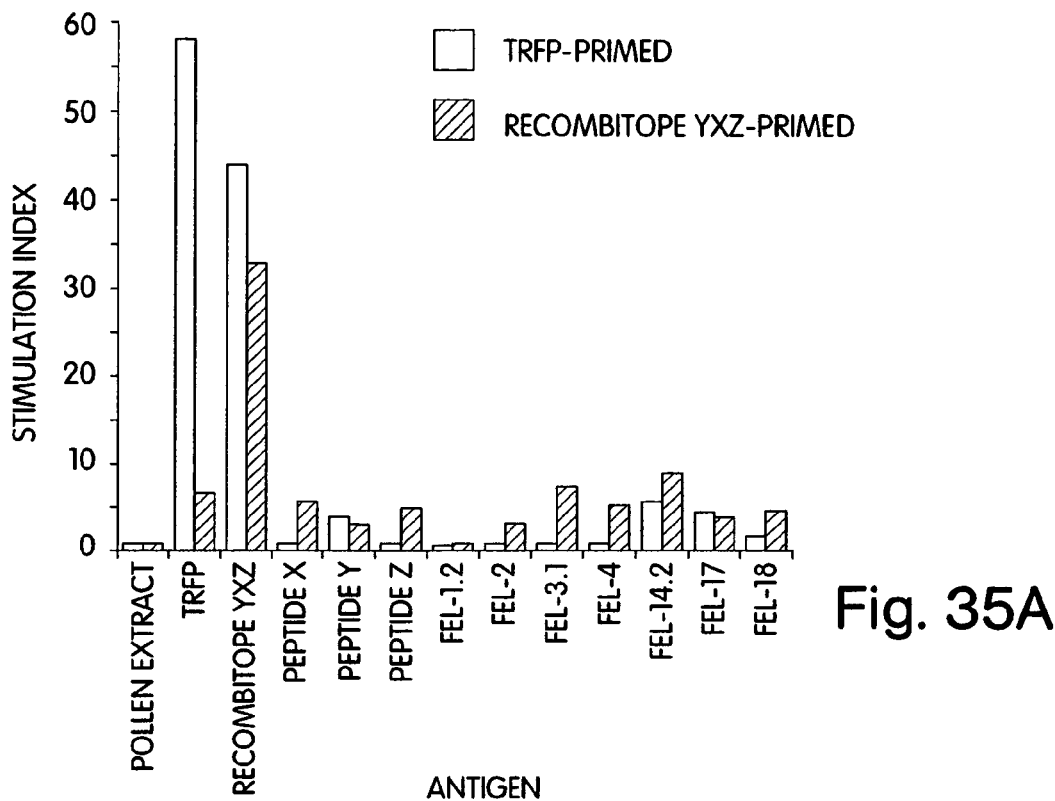
FIGS. 35A-C are graphic representations depicting the responses of T cell lines from three patients primed in vitro to TRFP, peptide YXZ, or peptide YZX, and analyzed for response to various peptides.
Figure 35B:
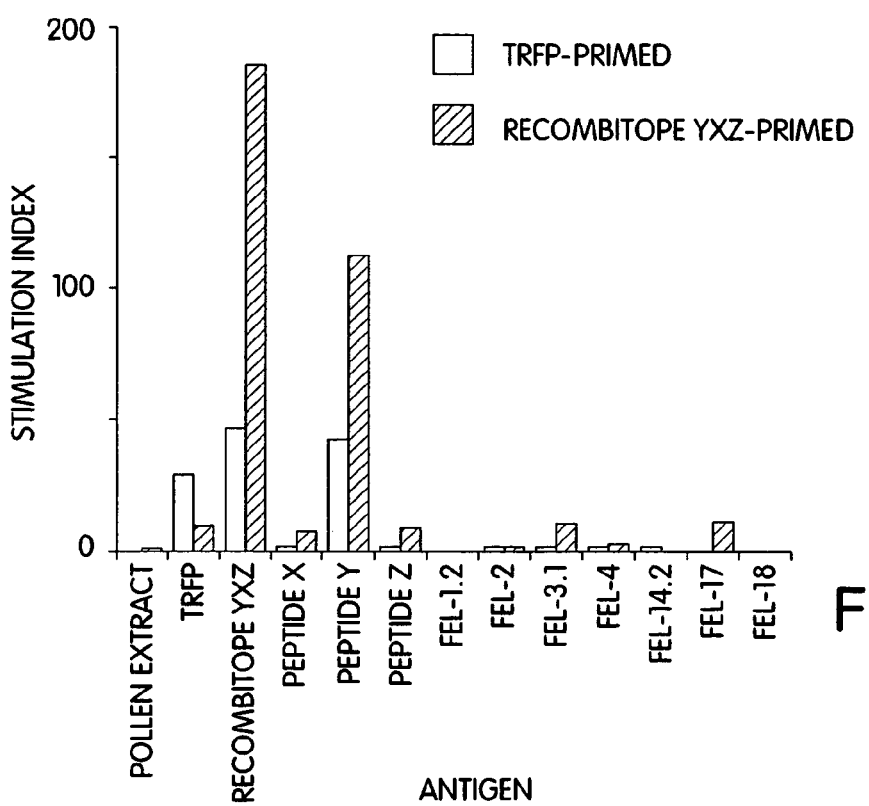
Figure 35C:
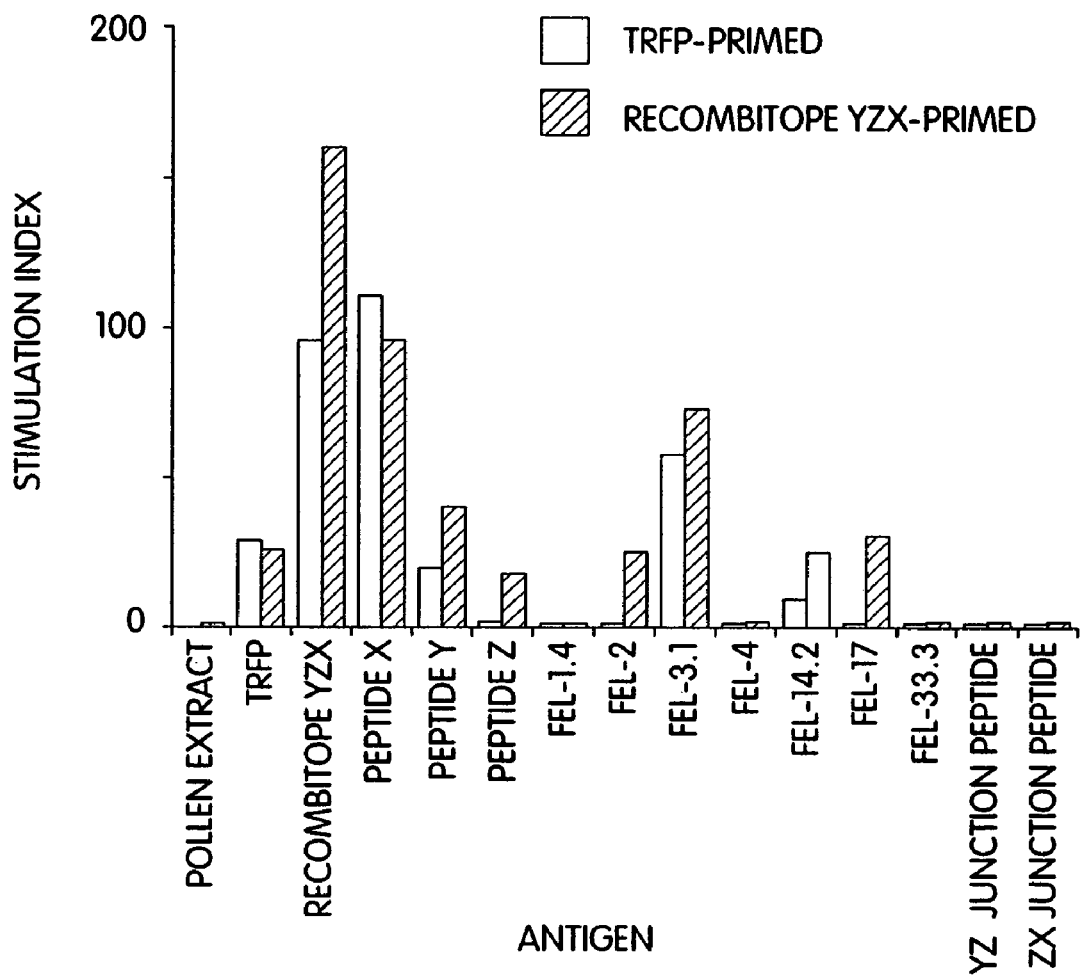
Figure 36:
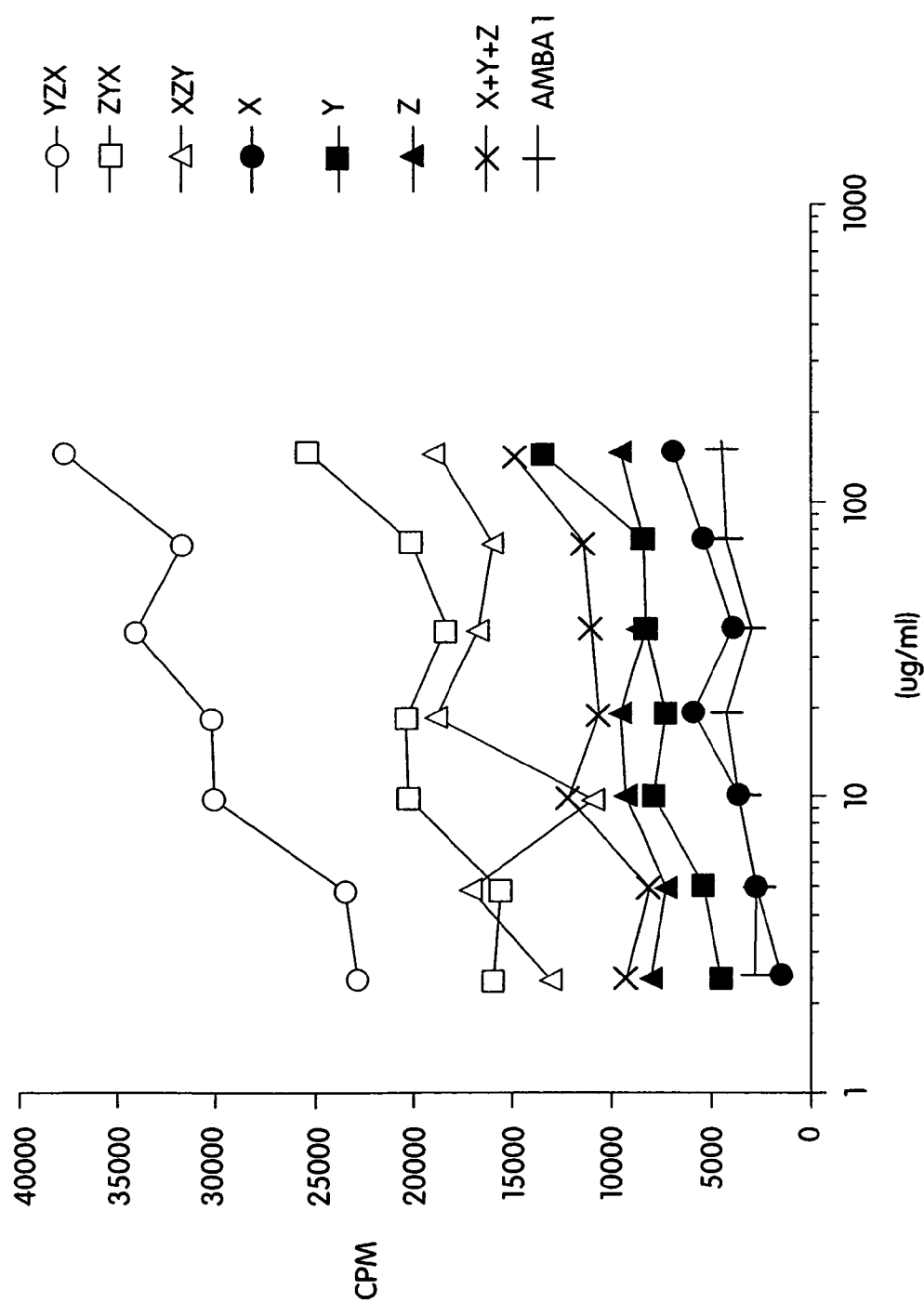
FIG. 36 is a graphic representation depicting responses of murine T cells immunized with peptide YZX and analyzed for response in vitro to culture with the peptide YZX as measured by IL-2 production.

Human T Cell Epitope Response to Peptides Comprising Two or More Regions of TRFP The human cat allergic T cell response to peptides produced as above was examined. Peripheral blood mononuclear cells (PBMC) were purified by Ficoll-Hypaque centrifugation of 60 ml of heparinized peripheral blood from cat-allergic patients, who exhibited clinical symptoms of cat allergy and who were skin test positive with cat extract. Ten million PBMC from an individual patient were cultured in 10 ml RPMI-1640 containing 5% pooled human AB serum and supplemented with glutamine, penicillin, streptomycin and HEPES buffer in the presence of 10 µg native affinity-purified TRFP/ml of culture or with 25 µg purified uncleaved peptide YXZ/ml of culture or with 25 µg purified cleaved peptide YZX/ml of culture at 37° C. for 7 days. Peptide YZX was cleaved with thrombin as described in Example 25. Viable cells were then purified by Ficoll-Hypaque centrifugation and cultured for 2 additional weeks in RPMI-1640/5% AB serum containing 5 units recombinant human IL-2/ml and 5 units recombinant human IL-4/ml. The resting T cells were then tested in a secondary proliferation assay using a 96 well microtiter plate to assess T cell responses to various TRFP proteins or peptides (TRFP antigens). For assay, 2×10$^4$ resting T cells were cultured for 3 days at 37° C. in the presence of 2×10$^4$ autologous Epstein-Barr virus transformed B cells (25,000 Rads) as antigen presenting cells with various concentrations of antigen in 200 µl per well. Each well then received 1 µCi tritiated thymidine for 16 hours. The counts incorporated were collected onto glass fiber filters and processed for liquid scintillation counting. The stimulation indices for responses to each antigen were then calculated as the maximum CPM in response to antigen divided by the medium control CPM. A stimulation index of 2.5 was considered to be a positive T cell response. A summary of the results of 3 such experiments (patients 522, 519, and 386 is shown in FIG. 35*a*, FIG. 35*b* and FIG. 35*c*). As compared to the experiments shown in FIGS. 35*a* and 35*b* in the experiment shown in FIG. 35, Fel-1.4 (chain 1, amino acid residues 6-17) was substituted for Fel-1.2 (chain 1, amino acid residues 1-17) and Fel-33.3 (chain 2, amino acid residues 26-40) was substituted for Fel-18 (chain 2, amino acid residues 23-48) in order to more closely resemble the constituent amino acids of peptides X and Z. In addition, in this experiment one peptide derived from the Y-Z junction of peptide YZX (amino acid residues 50-55 from chain 1 of TRFP and amino acid residues 14-19 from chain 2 of TRFP) and one peptide derived from the Z-X junction of peptide YZX (amino acid residues 34-39 of chain 2 of TRFP and amino acid residues 7-12 of chain 1 of TRFP) were synthesized and tested. These junction peptides were produced in order to determine whether these areas of peptide YZX produce a non-native epitope when formed in the peptide.

The results indicate that T cells from patient 522 primed with native TRFP positively respond to native TRFP, peptide YXZ, peptide Y, Fel-14.2 and Fel-17. In contrast, T cells primed with YXZ respond less well to native TRFP, but respond at a similar level or better to a number of synthetic peptides corresponding to portions of the TRFP molecule, including peptide X, peptide Y, peptide Z, Fel-4, Fel-3.1, Fel-2, Fel-14.2, Fel-17 and Fel-18. Similar results of an experiment with T cells from patient 519 are shown in FIG. 35b. Native TRFP-primed T cells from this patient respond to native purified TRFP, peptide YZX and peptide Y. When the same patient's cells were primed with peptide YZX, positive responses were shown to native TRFP peptide YZX, peptide X, peptide Y, peptide Z, Fel-3.1, Fel-4, and Fel-17. FIG. 35c shows a similar experiment involving purified cleaved YZX as the priming antigen. The results indicate that T cells from patient 386 primed with native TRFP positively respond to native TRFP, peptide YZX, peptide X, peptide Y, Fel-3.1, and Fel-14.2. In contrast, T cells primed with YZX respond at a similar level or better to native TRFP, peptide YZX, peptide X, peptide Y, peptide Z, Fel-2, Fel-3.1, Fel-14.2 and Fel-17. These data indicate that, at least in these three patients, T cells can efficiently recognize TRFP T cell epitopes when presented as a peptide. No epitopes present in the native TRFP molecule examined in these experiments are destroyed in the context of the YXZ peptide. The ability of the peptides YXZ or YZX to present TRFP epitopes in these experiments appears to be greater compared with the native molecule. The results from Patient 386 demonstrate that peptides derived from the junctional areas of the YZX (YZ junction peptide and ZX junction peptide) are not recognized by T cells when presented in a peptide; therefore, no non-native epitopes are created in the junctional areas.

EXAMPLE 28

Murine T Cell Response to Peptides Comprising Two or More Regions from TRFP

Mice were immunized with peptide YZX to determine whether T cell epitopes contained in the peptide derived from TRFP are capable of stimulating a T cell response. The assay determined the ability of lymph node cells to respond to the individual peptides as well as the immunizing antigen.

10 B6CBAF1 mice were immunized subcutaneously at the base of the tail and in the thigh region with 100 μg of peptide YZX in complete Freund's adjuvant. After 10 days, the inguinal, paraaortic, and popliteal nodes of the immunized mice were removed and pooled. The lymph node cells were suspended in cold RPMI 1640 with 1% fetal bovine serum (FBS) by passage through stainless steel mesh. The cells were washed 2 times with cold RPMI-1640 containing 1% FBS and maintained at 4° C.

The lymph node cells were plated at $4\times10^6$ cells/ml in RPMI 1640 with 10% FBS, 250 μg/ml penicillin G, 100 μg/ml streptomycin, and $5\times10^{-5}$ M 2-mercaptoethanol. The cells were cultured with antigen (i.e., peptide YZX, peptide ZYX, peptide XZY, peptide X, peptide Y, peptide Z, peptides X, Y and Z and Amb a I) as indicated (FIG. 36). After 24 hours, 50 μl of supernatant was removed from each culture and frozen overnight to eliminate live cell carryover. The supernatant was warmed to 370 degrees and washed. CTLL-2 indicator cells (ATCC # T1B 214) were added ($5\times10^3$ cells/well). This indicator cell line requires IL-2 for continued growth. After 24 hours, $H^3$-thymidine (1 μCi/well) was added and the cells were further incubated for 4 hours. The plates were frozen and thawed, harvested on a Tomtec 96 well harvester (Tomtec, Orange, Conn.), and counted on a Betaplate beta counter (Pharmacia, Gaithersburg, Md.).

The pooled lymph node cells respond well in vitro in response to culture with peptide YZX, as measured by IL-2 production (FIG. 36). The media only background averaged 1500 cpm. The T cell response to peptide YZX may result from one or a combination of responses to the individual peptide containing epitopes used to construct the peptide (i.e., peptides X, Y and Z). Other peptides as well as the individual peptides X, Y and Z were cultured with lymph node cells and the response of T cells was determined. There was significant response to each of the peptides X, Y and Z, the constituent peptides. There were strong T cell responses to several other peptides ZYX and XZY. There was a small, but significant, T cell response to a recombinant Amb a I preparation which has the same amino-terminal leader sequences as the peptides.

EXAMPLE 29

Application of Peptides to Allergic Disease Diagnosis

The peptides produced as described above, each having two or more regions from TRFP can be useful as a new form of diagnosis of sensitivity to TRFP. For example, although preferred peptides of the invention do not bind IgE, certain peptides derived from TRFP may be capable of binding allergic patient IgE. These peptides could be used in skin testing as an accurate assay for specific Immediate Type Hypersensitivity (ITH) in an individual to TRFP from which the peptide is derived. The allergens for eliciting the ITH response could also be recombinant TRFP, biochemically purified TRFP from natural sources in addition to peptides having two or more regions of T cell reactivity with the only requirement being a high degree of specific IgE reactivity. Peptides which show no, or very low, reactivity with human IgE but comprise T cell epitopes reactive with TRFP can be used to elicit a Delayed Type Hypersensitivity (DTH) reaction in an individual sensitive to the allergen from which the epitopes are derived. The allergen forms for generating the DTH response can be isolated peptides, recombinant TRFP or chemically modified natural or recombinant TRFP (e.g., KOH treated TRFP). Again, a major requirement of the DTH provoking allergen/antigen is lack of IgE binding reactivity, or if such binding occurs, lack of mediator release from mast cells or basophils and the ability to stimulate T cells in an individual upon administration. A positive DTH is indicative of T cells of the individual specific for the epitopes within the peptide. In general, peptides comprising two or more regions of T cell reactivity of TRFP are larger molecules than peptides which comprise an individual T cell epitope and are thus advantageous for DTH testing. Since such peptides are larger molecules, it is believed that they should reside in the skin (site of injection) allowing for the influx of T lymphocytes and other cells that contribute to the DTH skin response.

The ITH reaction, which occurs within 15 to 30 minutes of skin testing, can be used in combination with a DTH reaction, with the DTH reaction appearing 48-72 hours later. It is the combination of these assays, for two different types of allergic disease related reactivities, that represents a novel diagnostic formulation. The application to the skin during skin testing with a peptide may require a different format for eliciting one response versus another (ITH vs DTH). For example, the ITH reaction may be elicited in an individual by prick testing with a very small quantity of a therapeutic composition comprising a peptide (in this case the an IgE reactive peptide), and a pharmaceutically acceptable carrier or diluent. To elicit a DTH reaction, a large amount of a therapeutic composition comprising a peptide (in this case a non-IgE reactive peptide) and a pharmaceutically acceptable carrier or diluent is applied by an intradermal injection or tine test form (both are used for TB testing by DTH). See *Immunology* (1985) Roitt, I. M., Brostoff, J., Male, D. K. (eds), C.V. Mosby Co., Gower Medical Publishing, London, N.Y., pp. 19.2-19.18; pp. 22.1-22.1. Following diagnosis with peptides of the invention individuals can be selected for specific desensitization therapy by defining, in one test set, IgE reactivity and T epitope reactivity.

EXAMPLE 30

Administration of Peptides to Human Subjects for Treatment of Allergy to Cat A. Composition of Phase I Formulation For Phase I clinical trials the drug product was comprised of two freeze-dried peptide formulations, peptide X (SEQ. ID. NO: 17) and peptide Y (SEQ. ID. NO: 18). Peptide X and peptide Y were manufactured separately, and packaged into two distinct vials.

| PEPTIDE X | |
|---|---|
| Active: | 1.5 mg/vial |
| Inactives: | 0.1 M Sodium Phosphate, pH 5.7 |
| | 5% w/v Mannitol, U.S.P. |
| Diluent: | Sterile Water for Injection, U.S.P. |

| PEPTIDE Y | |
|---|---|
| Active: | 1.5 mg/vial |
| Inactives: | 0.1 M Sodium Phosphate, pH 5.7 |
| | 5% w/v Mannitol, U.S.P. |
| Diluent: | Sterile Water for Injection, U.S.P. |

In this study, the drug product was supplied in two separate vials as sterile, pyrogen free, lyophilized powders containing sodium phosphate and mannitol as excipients, and the active component peptide X or peptide Y.

Preparation of the drug product in these studies required reconstitution of the vials with sterile water for injection. Dilution of reconstituted vials was required to deliver lower doses in the dose titration concentrations of 7.5 or 75 μg/mL, and was accomplished using sterile 0.9% sodium chloride for injection. If desired, the vials could have been prepared with only 7.5 or 75 μg per peptide without need for dilutions.

The lyophilized drug product was stored at or below −20° C. and the drug product was administered immediately after reconstitution. These storage conditions and use conditions are not limiting.

B. Composition of Phase II Formulation

For Phase II clinical trials a single formulation containing 750 μg/ml final concentration of each peptide was developed. Peptide X and peptide Y were combined during the fill finish process to produce a vial containing a sterile, pyrogen free, lyophilized powder.

| Active: | 0.75 mg peptide X and 0.75 mg peptide Y |
|---|---|
| Inactives: | 0.05 M Sodium Phosphate, pH 6.2 |
| | 5% w/v Mannitol, U.S.P. |
| Diluent: | Sterile Water for Injection, U.S.P. (initial reconstitution) |
| | 0.9% Sodium Chloride for Injection |
| | (dilution beyond initial reconstitution) |

The freeze-dried drug product was reconstituted to 750 μg/ml concentration with sterile water for injection. Dilution of reconstituted vials for lower doses, e.g., to achieve concentrations of 7.5 or 75 μg/mL, was accomplished using sterile 0.9% sodium chloride for injection. Subjects were administered the drug product according to the administration instructions contained in the clinical protocol.

The drug product was administered immediately after reconstitution.

The lyophilized drug product was stored at or below −20° C.

C. Human Phase I and II Clinical Studies

The following Phase I and Phase II studies of peptides X and Y have been conducted in human cat-allergic subjects.

Protocol P92-01: Phase I Clinical Study of Safety and Activity of Peptides X and Y This Phase I, open-label, dose-escalating safety study was conducted to determine the safety of the administration of the peptide X and peptide Y. The antigenicity of the components was also evaluated, as was the activity of the peptides in altering skin test sensitivity.

Two centers, Johns Hopkins Asthma and Allergy Center, Baltimore, Md. and New England Medical Center, Boston, Mass., enrolled a total of nineteen (19) cat-allergic individuals in this study. Peptide X and peptide Y were administered separately but concomitantly by subcutaneous injections in escalating doses ranging from 7.5 μg to 1500 μg over a five-week period.

Safety was assessed by evaluations of clinical laboratory parameters, physical examination, antibody studies and adverse experiences. Activity was assessed by analysis of skin testing. Prick and intradermal skin testing with both affinity purified native Fel d I and the peptides were performed one week prior to, and two and six weeks following the treatment period. Sixteen patients were treated with peptides X and Y during the study. The peptides were well tolerated at doses of up to 1500 μg. There were no serious adverse experiences and the safety of the peptides to justify further clinical development was confirmed. Adverse events recorded with the trial were typical of those seen in open label allergy studies. Patients were all cat allergic individuals in this trial and tolerated doses which are orders of magnitude higher than can be achieved with conventional allergen immunotherapy.

One patient discontinued the study due to an asthma attack which occurred following skin testing with cat extract I and peptides on Week 1, and a second asthma attack which occurred following the 7.5 μg dose of each peptide on Week 2. It is unclear whether there is a direct relationship between treatment with the peptides and the onset of asthma in this patient. It is noteworthy that the study was conducted during one of the most severe pollen seasons of recent years and this patient, like many of those enrolled, had seasonal allergies.

Antibody studies revealed that all evaluable patients had IgG and IgE antibodies to Fel d I. In all but two patients, the concentrations did not change over the course of the study. Two patients demonstrated IgE antibodies to peptide X and/or peptide Y at Weeks 8 and 12 which were not present at Week 1. One of these patients had a substantial skin test reaction to peptide X at Week 8 which was not present at Week 12. Five patients had endogenous IgG antibody to peptide X and three patients had IgG antibody to peptide Y prior to exposure to the peptides. Four patients with no pre-existing, anti-peptide IgG antibodies to peptide X and/or peptide Y developed increased concentrations of such antibodies during or after treatment. Two patients developed a positive immediate skin test reaction to a treatment peptide during the study but without clinical correlation. Another patient had a delayed local reaction to skin testing with peptide Y at Week 8 which was related to the intradermal dose of peptide Y.

Skin test results to cat allergen showed a statistically-significant decrease in reactivity to cat extract containing Fel d I at two or three dilutions by prick test after 8 or 12 weeks, respectively. No statistically significant differences in reactivity were detected by the intradermal method. There was a statistically-significant decrease in the late phase reactivity to Fel d I ($\Sigma_E$) at six and twenty-four hours at the Johns Hopkins site when Week 8 was compared to baseline (Week 1). The decrease was not significant when Week 12 was compared to baseline.

Although this study was designed to evaluate safety, the skin testing data suggested that the peptides may be causing desensitization to Fel d I.

Protocol P92-02: Phase II Clinical Study of the Safety and Activity of Peptides X and Y Using a Cat Room Challenge Model This phase II safety and efficacy study was a double blind placebo-controlled study of peptides X and Y given subcutaneously in four weekly doses of 7.5 µg, 75 µg, or 750 µg per peptide. Patient's sensitivity to natural exposure was assessed by measurement of symptom scores and pulmonary function during a 60-minute period in a small room containing stuffed furniture and two cats. This cat room challenge occurred pretreatment and one and six weeks posttreatment. In the cat room, patients rated nose, eye and lung symptoms on a five point scale every five minutes. Pulmonary function was tested every 15 minutes. Additional parameters assessed during the study were skin test sensitivity to cat extract and peptides X and Y, specific IgE and IgG to Fel d I and component peptides X and Y, and T cell responsiveness to cat antigen and selected peptides.

Ninety-five patients were enrolled at two centers, Johns Hopkins Asthma and Allergy Center, Baltimore, Md. and New England Medical Center, Boston, Mass. Ninety-one patients completed the trial. Four patients discontinued, two because of transient allergic symptoms associated with the therapy and two because of scheduling conflicts.

The therapy was generally well tolerated. Analysis of the primary efficacy data for the study revealed a significant dose response relationship was considered statistically significant (see FIG. 37) for control of allergic symptoms (nasal, lung, and total allergy) induced by cat room exposure at one and six weeks posttreatment. Statistically significant pairwise comparisons versus placebo for nasal and total allergy symptoms at 75 µg and 750 µg was detected at six weeks (See FIG. 1). The 7.5 µg dose could not be distinguished from placebo. Patients were prick test negative to study medication pretreatment, but 13 patients had positive prick and/or intradermal skin test to treatment peptides. Two patients developed significant titres of IgE to treatment peptide and were skin test positive to study medication post-treatment. Only five patients with positive skin tests to peptide had measurable IgE to peptide. A proportion of patients (placebo: 57.7%; 7.5 µg: 60.9%; 75 µg: 63.6%; 750 µg: 83.3%) reported cat-allergic symptoms such as rhinorrhea, nasal congestion, pruritus, chest tightness, and/or wheezing during this study. The study medication appeared to induce some mild transient symptoms suggestive of natural cat exposure. The incidence was dose-related (placebo: 11.5-19.2%; 7.5 µg: 21.7-26.1%; 75 µg: 31.8-45.5%; and 750 µg: 50.0-62.5%). Such symptoms were generally mild, self limited and required no treatment or were controlled with beta agonist and/or antihistamine. One patient was treated with adrenaline, and six patients had asthmatic symptoms with drop in peak flow. All were managed easily. The treatment did not alter antibody responses to call allergies in the time period studied, did not effect skin teat reactivity relative to placebo, but was associated with improvement of total allergy score in 80% of study patients. Additional studies to better characterize the treatment effect are underway.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

The invention claimed is:

1. A therapeutic composition, comprising a mixture of the following isolated polypeptides:
   (a) an isolated polypeptide comprising the amino acid sequence set forth in SEQ ID NO:6; and
   (b) an isolated polypeptide consisting of residues 14-39 of SEQ ID NO:6, or an epitope-containing portion thereof;
   wherein said composition is capable of reducing an allergic response to a cat antigen in an individual sensitive to said antigen.

2. The composition according to claim 1, wherein at least one of the polypeptides has a stimulation index of at least 4.0 or a positivity index of at least 250, wherein the stimulation index is defined as the ratio of measured proliferation of T cells and antigen presenting cells from a responding individual when exposed to antigen, to the measured proliferation of said cells in the absence of antigen, and wherein the positivity index is defined as the average stimulation index of a population of responding individuals tested multiplied by the percentage of individuals in the population exhibiting a positive response.

3. The composition according to claim 1, wherein at least one of the polypeptides is produced recombinantly.

4. The composition according to claim 1, wherein at least one of the polypeptides is produced by chemical synthesis.

5. An isolated polypeptide consisting of Fel 31-2 (residues 14-39 of SEQ ID NO:6).

6. A composition comprising the polypeptide of claim 5 and a pharmaceutical acceptable carrier.

7. The composition of claim 6, further comprising a second isolated polypeptide comprising the amino acid sequence set forth in SEQ ID NO:6.

8. The composition of claim 5 or 6, further comprising a fragment of a protein allergen comprising the amino acid sequence set forth in SEQ ID NO:6.

9. The composition of claim 8, wherein the fragment is capable of stimulating T cells.

10. The composition of claim 6, further comprising at least one peptide selected from the group consisting of:
Fel 16 (residues 1-22 of SEQ ID NO:6),
Fel 17 (residues 12-33 of SEQ ID NO:6),
Fel 32-1 (residues 12-24 of SEQ ID NO:6),
Fel 32-2 (residues 14-24 of SEQ ID NO:6),
Fel 32-3 (residues 16-24 of SEQ ID NO:6),
Fel 18 (residues 23-48 of SEQ ID NO:6),
Fel 33-1 (residues 26-36 of SEQ ID NO:6),
Fel 33-2 (residues 26-38 of SEQ ID NO:6),
Fel 33-3 (residues 26-40 of SEQ ID NO:6),
Fel 31-1 (residues 14-40 of SEQ ID NO:6),
Fel 31-3 (residues 14-38 of SEQ ID NO:6),
Fel 31-4 (residues 14-37 of SEQ ID NO:6),
Fel 31-5 (residues 14-36 of SE ID NO:6),
Fel 31-6 (residues 15-40 of SEQ ID NO:6),
Fel 31-7 (residues 15-36 of SEQ ID NO:6),
Fel 20-1 (residues 34-59 of SEQ ID NO:6),
Fel 25 (residues 49-68 of SEQ ID NO:6), and
Fel 28 (residues 60-82 of SEQ ID NO:6).

* * * * *

SEQUENCE LISTING (1) GENERAL INFORMATION:

(iii) NUMBER OF SEQUENCES: 103

(2) INFORMATION FOR SEQ ID NO: 1:

(i) SEQUENCE CHARACTERISTICS:
      (A) LENGTH: 418 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS (B) LOCATION: 2..283

(ix) FEATURE:
    (A) NAME/KEY: mat_peptide
    (B) LOCATION: 74..283

(xi) SEQUENCE DESCRIPTION: SEQ ID NO: 1:

```
C TGC ATC ATG AAG GGG GCT CGT GTT CTC GTG CTT CTC TGG GCT GCC       46
  Cys Ile Met Lys Gly Ala Arg Val Leu Val Leu Leu Trp Ala Ala
  -24         -20                 -15                 -10

TTG CTC TTG ATC TGG GGT GGA AAT TGT GAA ATT TGC CCA GCC GTG AAG     94
Leu Leu Leu Ile Trp Gly Gly Asn Cys Glu Ile Cys Pro Ala Val Lys
                -5                  1               5

AGG GAT GTT GAC CTA TTC CTG ACG GGA ACC CCC GAC GAA TAT GTT GAG    142
Arg Asp Val Asp Leu Phe Leu Thr Gly Thr Pro Asp Glu Tyr Val Glu
         10                  15                  20

CAA GTG GCA CAA TAC AAA GCA CTA CCT GTA GTA TTG GAA AAT GCC AGA    190
Gln Val Ala Gln Tyr Lys Ala Leu Pro Val Val Leu Glu Asn Ala Arg
 25                  30                  35

ATA CTG AAG AAC TGC GTT GAT GCA AAA ATG ACA GAA GAG GAT AAG GAG    238
Ile Leu Lys Asn Cys Val Asp Ala Lys Met Thr Glu Glu Asp Lys Glu
 40                  45                  50                  55

AAT GCT CTC AGC TTG CTG GAC AAA ATA TAC ACA AGT CCT CTG TGT        283
Asn Ala Leu Ser Leu Leu Asp Lys Ile Tyr Thr Ser Pro Leu Cys
                 60                  65                  70

TAAAGGAGCC ATCACTGCCA GGAGCCCTAA GGAAGCCACT GAACTGATCA CTAAGTAGTC   343

TCAGCAGCCT GCCATGTCCA GGTGTCTTAC TAGAGGATTC CAGCAATAAA AGCCTGGCAA   403

TTCAAACAAA AAAAA                                                   418
```

(2) INFORMATION FOR SEQ ID NO: 2:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO: 2:

```
Cys Ile Met Lys Gly Ala Arg Val Leu Val Leu Leu Trp Ala Ala Leu
-24         -20                 -15                 -10

Leu Leu Ile Trp Gly Gly Asn Cys Glu Ile Cys Pro Ala Val Lys Arg
            -5                   1               5

Asp Val Asp Leu Phe Leu Thr Gly Thr Pro Asp Glu Tyr Val Glu Gln
     10                  15                  20

Val Ala Gln Tyr Lys Ala Leu Pro Val Val Leu Glu Asn Ala Arg Ile
 25                  30                  35                  40

Leu Lys Asn Cys Val Asp Ala Lys Met Thr Glu Glu Asp Lys Glu Asn
             45                  50                  55

Ala Leu Ser Leu Leu Asp Lys Ile Tyr Thr Ser Pro Leu Cys
             60                  65                  70
```

(2) INFORMATION FOR SEQ ID NO: 3:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..289

(ix) FEATURE:
        (A) NAME/KEY: mat_peptide
        (B) LOCATION: 80..289

(xi) SEQUENCE DESCRIPTION: SEQ ID NO: 3:

```
G GCC TGG CGG TGC TCC TGG AAA AGG ATG TTA GAC GCA GCC CTC CCA         46
  Ala Trp Arg Cys Ser Trp Lys Arg Met Leu Asp Ala Ala Leu Pro
  -26 -25             -20                 -15

CCC TGC CCT ACT GTT GCG GCC ACA GCA GAT TGT GAA ATT TGC CCA GCC       94
Pro Cys Pro Thr Val Ala Ala Thr Ala Asp Cys Glu Ile Cys Pro Ala
-10                 -5                   1                   5

GTG AAG AGG GAT GTT GAC CTA TTC CTG ACG GGA ACC CCC GAC GAA TAT      142
Val Lys Arg Asp Val Asp Leu Phe Leu Thr Gly Thr Pro Asp Glu Tyr
                10                  15                  20

GTT GAG CAA GTG GCA CAA TAC AAA GCA CTA CCT GTA GTA TTG GAA AAT      190
Val Glu Gln Val Ala Gln Tyr Lys Ala Leu Pro Val Val Leu Glu Asn
            25                  30                  35

GCC AGA ATA CTG AAG AAC TGC GTT GAT GCA AAA ATG ACA GAA GAG GAT      238
Ala Arg Ile Leu Lys Asn Cys Val Asp Ala Lys Met Thr Glu Glu Asp
        40                  45                  50

AAG GAG AAT GCT CTC AGC TTG CTG GAC AAA ATA TAC ACA AGT CCT CTG      286
Lys Glu Asn Ala Leu Ser Leu Leu Asp Lys Ile Tyr Thr Ser Pro Leu
    55                  60                  65

TGT TAAAGGAGCC ATCACTGCCA GGAGCCCTAA GGAAGCCACT GAACTGATCA            339
Cys
 70

CTAAGTAGTC TCAGCAGCCT GCCATGTCCA GGTGTCTTAC TAGAGGATTC CAGCAATAAA    399

AGCCTTGCAA TTCAAACAAA A                                              420
```

(2) INFORMATION FOR SEQ ID NO: 4:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO: 4:

```
Ala Trp Arg Cys Ser Trp Lys Arg Met Leu Asp Ala Ala Leu Pro Pro
-26 -25             -20                 -15

Cys Pro Thr Val Ala Ala Thr Ala Asp Cys Glu Ile Cys Pro Ala Val
-10                 -5                   1                   5

Lys Arg Asp Val Asp Leu Phe Leu Thr Gly Thr Pro Asp Glu Tyr Val
                10                  15                  20

Glu Gln Val Ala Gln Tyr Lys Ala Leu Pro Val Val Leu Glu Asn Ala
            25                  30                  35

Arg Ile Leu Lys Asn Cys Val Asp Ala Lys Met Thr Glu Glu Asp Lys
        40                  45                  50

Glu Asn Ala Leu Ser Leu Leu Asp Lys Ile Tyr Thr Ser Pro Leu Cys
    55                  60                  65                  70
```

(2) INFORMATION FOR SEQ ID NO: 5:

(i) SEQUENCE CHARACTERISTICS:
        (A) LENGTH: 476 base pairs
        (B) TYPE: nucleic acid
        (C) STRANDEDNESS: single

```
         (D) TOPOLOGY: linear (ii) MOLECULE TYPE: cDNA (ix) FEATURE:
          (A) NAME/KEY: CDS
          (B) LOCATION: 2..334

(ix) FEATURE:
          (A) NAME/KEY: mat_peptide
          (B) LOCATION: 59..334

(xi) SEQUENCE DESCRIPTION: SEQ ID NO: 5:

T GAC ACG ATG AGG GGG GCA CTG CTT GTG CTG GCA TTG CTG GTG ACC          46
  Asp Thr Met Arg Gly Ala Leu Leu Val Leu Ala Leu Leu Val Thr
  -19             -15                 -10                 -5

CAA GCG CTG GGC GTC AAG ATG GCG GAA ACT TGC CCC ATT TTT TAT GAC        94
Gln Ala Leu Gly Val Lys Met Ala Glu Thr Cys Pro Ile Phe Tyr Asp
                1               5                   10

GTC TTT TTT GCG GTG GCC AAT GGA AAT GAA TTA CTG TTG GAC TTG TCC       142
Val Phe Phe Ala Val Ala Asn Gly Asn Glu Leu Leu Leu Asp Leu Ser
            15                  20                  25

CTC ACA AAA GTC AAT GCT ACT GAA CCA GAG AGA ACA GCC ATG AAA AAA       190
Leu Thr Lys Val Asn Ala Thr Glu Pro Glu Arg Thr Ala Met Lys Lys
        30                  35                  40

ATC CAG GAT TGC TAC GTG GAG AAC GGA CTC ATA TCC AGG GTC TTG GAT       238
Ile Gln Asp Cys Tyr Val Glu Asn Gly Leu Ile Ser Arg Val Leu Asp
 45                 50                  55                  60

GGA CTA GTC ATG ACA ACC ATC AGC TCC AGC AAA GAT TGC ATG GGT GAA       286
Gly Leu Val Met Thr Thr Ile Ser Ser Ser Lys Asp Cys Met Gly Glu
                65                  70                  75

GCA GTT CAG AAC ACC GTA GAA GAT CTC AAG CTG AAC ACT TTG GGG AGA       334
Ala Val Gln Asn Thr Val Glu Asp Leu Lys Leu Asn Thr Leu Gly Arg
            80                  85                  90

TGAATCTTTG CCACTGATGC CCTTCTGAG CCCCATCCTC CTGCCCTGTT CTTTACACCT      394

AAAGCTGGAA TCCAGACACC TGTCCTCACC TAATTCACTC TCAATCAGGC TGACTAGAAT     454

AAAATAACTG CATCTTAAAA AA                                              476

(2) INFORMATION FOR SEQ ID NO: 6:

(i) SEQUENCE CHARACTERISTICS:
         (A) LENGTH: 111 amino acids
         (B) TYPE: amino acid
         (D) TOPOLOGY: linear (ii) MOLECULE TYPE: protein (xi) SEQUENCE DESCRIPTION: SEQ ID NO: 6:

Asp Thr Met Arg Gly Ala Leu Leu Val Leu Ala Leu Leu Val Thr Gln
-19             -15                 -10                 -5

Ala Leu Gly Val Lys Met Ala Glu Thr Cys Pro Ile Phe Tyr Asp Val
            1               5                   10

Phe Phe Ala Val Ala Asn Gly Asn Glu Leu Leu Leu Asp Leu Ser Leu
        15                  20                  25

Thr Lys Val Asn Ala Thr Glu Pro Glu Arg Thr Ala Met Lys Lys Ile
    30                  35                  40                  45

Gln Asp Cys Tyr Val Glu Asn Gly Leu Ile Ser Arg Val Leu Asp Gly
                50                  55                  60

Leu Val Met Thr Thr Ile Ser Ser Ser Lys Asp Cys Met Gly Glu Ala
            65                  70                  75

Val Gln Asn Thr Val Glu Asp Leu Lys Leu Asn Thr Leu Gly Arg
```

-continued

```
                 80                  85                  90

(2) INFORMATION FOR SEQ ID NO: 7:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..327

(ix) FEATURE:
        (A) NAME/KEY: mat_peptide
        (B) LOCATION: 59..327

(xi) SEQUENCE DESCRIPTION: SEQ ID NO: 7:

GAC ACG ATG AGG GGG GCA CTG CTT GTG CTG GCA TTG CTG GTG ACC CAA         48
Asp Thr Met Arg Gly Ala Leu Leu Val Leu Ala Leu Leu Val Thr Gln
-19             -15                 -10                 -5

GCG CTG GGC GTC AAG ATG GCG GAG ACG TGC CCC ATT TTT TAT GAC GTC         96
Ala Leu Gly Val Lys Met Ala Glu Thr Cys Pro Ile Phe Tyr Asp Val
                1                   5                   10

TTT TTT GCG GTG GCC AAT GGA AAT GAA TTA CTG TTG GAC TTG TCC CTC        144
Phe Phe Ala Val Ala Asn Gly Asn Glu Leu Leu Leu Asp Leu Ser Leu
        15                  20                  25

ACA AAA GTC AAT GCT ACT GAA CCA GAG AGA ACA GCC ATG AAA AAA ATC        192
Thr Lys Val Asn Ala Thr Glu Pro Glu Arg Thr Ala Met Lys Lys Ile
 30                 35                  40                  45

CAG GAT TGC TAC GTG GAG AAC GGA CTC ATA TCC AGG GTC TTG GAT GGA        240
Gln Asp Cys Tyr Val Glu Asn Gly Leu Ile Ser Arg Val Leu Asp Gly
                50                  55                  60

CTA GTC ATG ATA GCC ATC AAC GAA TAT TGC ATG GGT GAA GCA GTT CAG        288
Leu Val Met Ile Ala Ile Asn Glu Tyr Cys Met Gly Glu Ala Val Gln
            65                  70                  75

AAC ACC GTA GAA GAT CTC AAG CTG AAC ACT TTG GGG AGA TGAATCTTTG         337
Asn Thr Val Glu Asp Leu Lys Leu Asn Thr Leu Gly Arg
        80                  85                  90

CCACTGATGC CCCTTCTGAG CCCCATCCTC CTGTCCTGTT CTTTACACCT AAAGCTGGAA      397

TCCAGACACC TGTCCTCACC TAATTCACTC TCAATCAGGC TGACTAGAAT AAAATAACTG      457

CATCTTAAAA AA                                                          469

(2) INFORMATION FOR SEQ ID NO: 8:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO: 8:

Asp Thr Met Arg Gly Ala Leu Leu Val Leu Ala Leu Leu Val Thr Gln
-19             -15                 -10                 -5

Ala Leu Gly Val Lys Met Ala Glu Thr Cys Pro Ile Phe Tyr Asp Val
                1                   5                   10

Phe Phe Ala Val Ala Asn Gly Asn Glu Leu Leu Leu Asp Leu Ser Leu
        15                  20                  25

Thr Lys Val Asn Ala Thr Glu Pro Glu Arg Thr Ala Met Lys Lys Ile
```

```
                    30                  35                  40                  45
Gln Asp Cys Tyr Val Glu Asn Gly Leu Ile Ser Arg Val Leu Asp Gly
                50                  55                  60
Leu Val Met Ile Ala Ile Asn Glu Tyr Cys Met Gly Glu Ala Val Gln
            65                  70                  75
Asn Thr Val Glu Asp Leu Lys Leu Asn Thr Leu Gly Arg
        80                  85                  90

(2) INFORMATION FOR SEQ ID NO: 9:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..291

(ix) FEATURE:
        (A) NAME/KEY: mat_peptide
        (B) LOCATION: 58..291

(xi) SEQUENCE DESCRIPTION: SEQ ID NO: 9:

GAC ACG ATG AGG GGG GCA CTG CTT GTG CTG GCA TTG CTG GTG ACC CAA      48
Asp Thr Met Arg Gly Ala Leu Leu Val Leu Ala Leu Leu Val Thr Gln
-19             -15                 -10                 -5

GCG CTG GGC GTC AAG ATG GCG GAG ACG TGC CCC ATT TTT TAT GAC GTC      96
Ala Leu Gly Val Lys Met Ala Glu Thr Cys Pro Ile Phe Tyr Asp Val
            1                   5                   10

TTT TTT GCG GTG GCC AAT GGA AAT GAA TTA CTG TTG GAC TTG TCC CTC     144
Phe Phe Ala Val Ala Asn Gly Asn Glu Leu Leu Leu Asp Leu Ser Leu
        15                  20                  25

ACA AAA GTC AAT GCT ACT GAA CCA GAG AGA ACA GCC ATG AAA AAA ATC     192
Thr Lys Val Asn Ala Thr Glu Pro Glu Arg Thr Ala Met Lys Lys Ile
    30                  35                  40                  45

CAG GAT TGC TAC GTG GAG AAC GGA CTC ATA TCC AGG GTC TTG GAT GGA     240
Gln Asp Cys Tyr Val Glu Asn Gly Leu Ile Ser Arg Val Leu Asp Gly
                50                  55                  60

CTA GCC ATG CCA TCA ACG AAT ATT GCA TGG GTG AAG CAG TTC AGA ACA     288
Leu Ala Met Pro Ser Thr Asn Ile Ala Trp Val Lys Gln Phe Arg Thr
            65                  70                  75

CCG TAGAAGATCT CAAGCTGAAC ACTTTGGGGA GATGAATCTT TGCCACTGAT          341
Pro

GCCCCTTCTG AGCCCCATCC TCCTGTCCTG TTCTTTACAC CTAAAGCTGG AATCCAGACA   401

CCTGTCCTCA CCTAATTCAC TCTCAATCAG GCTGACTAGA ATAAATAAC TGCATCTTAA    461

AAAA                                                                465

(2) INFORMATION FOR SEQ ID NO: 10:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 10:

Asp Thr Met Arg Gly Ala Leu Leu Val Leu Ala Leu Leu Val Thr Gln
-19             -15                 -10                 -5
```

```
Ala Leu Gly Val Lys Met Ala Glu Thr Cys Pro Ile Phe Tyr Asp Val
       1               5                  10

Phe Phe Ala Val Ala Asn Gly Asn Glu Leu Leu Asp Leu Ser Leu
       15                  20                  25

Thr Lys Val Asn Ala Thr Glu Pro Glu Arg Thr Ala Met Lys Lys Ile
 30                  35                  40                  45

Gln Asp Cys Tyr Val Glu Asn Gly Leu Ile Ser Arg Val Leu Asp Gly
                50                  55                  60

Leu Ala Met Pro Ser Thr Asn Ile Ala Trp Val Lys Gln Phe Arg Thr
                65                  70                  75

Pro (2) INFORMATION FOR SEQ ID NO: 11:

(i) SEQUENCE CHARACTERISTICS:
        (A) LENGTH: 94 amino acids
        (B) TYPE: amino acid
        (D) TOPOLOGY: linear (ii) MOLECULE TYPE: peptide (v) FRAGMENT TYPE: internal (ix) FEATURE:
         (A) NAME/KEY: Protein
         (B) LOCATION: 25..94

(xi) SEQUENCE DESCRIPTION: SEQ ID NO: 11:

Cys Ile Met His Gly Ala Arg Val Leu Val Leu Leu Trp Ala Ala Leu
              -20                 -15                 -10

Leu Leu Ile Trp Gly Gly Asn Cys Glu Ile Cys Pro Ala Val Lys Arg
         -5                   1                   5

Asp Val Asp Leu Phe Leu Thr Gly Thr Pro Asp Glu Tyr Val Glu Gln
 10                  15                  20

Val Ala Gln Tyr Lys Ala Leu Pro Val Val Leu Glu Asn Ala Arg Ile
 25                  30                  35                  40

Leu Lys Asn Cys Val Asp Ala Lys Met Thr Glu Glu Asp Lys Glu Asn
                 45                  50                  55

Ala Leu Ser Leu Leu Asp Lys Ile Tyr Thr Ser Pro Leu Cys
                 60                  65                  70

(2) INFORMATION FOR SEQ ID NO: 12:

(i) SEQUENCE CHARACTERISTICS:
        (A) LENGTH: 96 amino acids
        (B) TYPE: amino acid
        (D) TOPOLOGY: linear (ii) MOLECULE TYPE: peptide (v) FRAGMENT TYPE: internal (ix) FEATURE:
         (A) NAME/KEY: Protein
         (B) LOCATION: 27..96

(xi) SEQUENCE DESCRIPTION: SEQ ID NO: 12:

Ala Trp Arg Cys Ser Trp Lys Arg Met Leu Asp Ala Ala Leu Pro Pro
             -25                 -20                 -15

Cys Pro Thr Asn Ala Ala Thr Ala Asp Cys Glu Ile Cys Pro Ala Val
-10                  -5                   1                   5

Lys Arg Asp Val Asp Leu Phe Leu Thr Gly Thr Pro Asp Glu Tyr Val
```

```
                     10              15              20
Glu Gln Val Ala Gln Tyr Lys Ala Leu Pro Val Val Leu Glu Asn Ala
                 25              30              35
Arg Ile Leu Lys Asn Cys Val Asp Ala Lys Met Thr Glu Glu Asp Lys
    40              45              50
Glu Asn Ala Leu Ser Leu Leu Asp Lys Ile Tyr Thr Ser Pro Leu Cys
55              60              65              70
```

(2) INFORMATION FOR SEQ ID NO: 13:

(i) SEQUENCE CHARACTERISTICS:
        (A) LENGTH: 92 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 13:

```
Val Lys Met Ala Glu Thr Cys Pro Ile Phe Tyr Asp Val Phe Phe Ala
1               5                   10                  15
Val Ala Asn Gly Asn Glu Leu Leu Leu Asp Leu Ser Leu Thr Lys Val
                20                  25                  30
Asn Ala Thr Glu Pro Glu Arg Thr Ala Met Lys Lys Ile Gln Asp Cys
                35                  40                  45
Tyr Val Glu Asn Gly Leu Ile Ser Arg Val Leu Asp Gly Leu Val Met
                50                  55                  60
Thr Thr Ile Ser Ser Ser Lys Asp Cys Met Gly Glu Ala Val Gln Asn
65                  70                  75                  80
Thr Val Glu Asp Leu Lys Leu Asn Thr Leu Gly Arg
                85                  90
```

(2) INFORMATION FOR SEQ ID NO: 14:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 14:

```
Val Lys Met Ala Glu Thr Cys Pro Ile Phe Tyr Asp Val Phe Phe
1               5                   10                  15
Ala Val Ala Asn Gly Asn Glu Leu Leu Leu Asp Leu Ser Leu Thr Lys
                20                  25                  30
Val Asn Ala Thr Glu Pro Glu Arg Thr Ala Met Lys Lys Ile Gln Asp
                35                  40                  45
Cys Tyr Val Glu Asn Gly Leu Ile Ser Arg Val Leu Asp Gly Leu Val
                50                  55                  60
Met Ile Ala Ile Asn Glu Tyr Cys Met Gly Glu Ala Val Gln Asn Thr
            65                  70                  75
Val Glu Asp Leu Lys Leu Asn Thr Leu Gly Arg
80                  85                  90
```

(2) INFORMATION FOR SEQ ID NO: 15:

(i) SEQUENCE CHARACTERISTICS:

(A) LENGTH: 51 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 15:

Ser Leu Thr Lys Val Asn Ala Thr Glu Pro Glu Arg Thr Ala Met Lys
1               5                   10                  15

Lys Ile Gln Asp Cys Tyr Val Glu Asn Gly Leu Ile Ser Arg Val Leu
            20                  25                  30

Asp Gly Leu Val Met Pro Ser Thr Asn Ile Ala Trp Val Lys Gln Phe
        35                  40                  45

Arg Thr Pro
    50

(2) INFORMATION FOR SEQ ID NO: 16:

(i) SEQUENCE CHARACTERISTICS:
        (A) LENGTH: 82 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: misc_feature
        (B) LOCATION: 65
        (D) OTHER INFORMATION: /label=Xaa is Ile or Thr (ix) FEATURE:
        (A) NAME/KEY: misc_feature
        (B) LOCATION: 66
        (D) OTHER INFORMATION: /label=Xaa is Ala or Thr (ix) FEATURE:
        (A) NAME/KEY: misc_feature
        (B) LOCATION: 68
        (D) OTHER INFORMATION: /label=Xaa is Asn or Ser (ix) FEATURE:
        (A) NAME/KEY: misc_feature
        (B) LOCATION: 69
        (D) OTHER INFORMATION: /label=Xaa is Glu or Ser (ix) FEATURE:
        (A) NAME/KEY: misc_feature
        (B) LOCATION: 80
        (D) OTHER INFORMATION: /label=Xaa is Ala or Thr (ix) FEATURE:
        (A) NAME/KEY: misc_feature
        (B) LOCATION: 81
        (D) OTHER INFORMATION: /label=Xaa is Met or Val (xi) SEQUENCE DESCRIPTION: SEQ ID NO: 16:

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30

Xaa Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Xaa Xaa Ile Xaa Xaa Lys Asp Cys Met Gly Glu Ala Val Gln Asn Xaa

```
65                  70                  75                  80
Xaa Glu (2) INFORMATION FOR SEQ ID NO: 17:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 17:

Lys Arg Asp Val Asp Leu Phe Leu Thr Gly Thr Pro Asp Glu Tyr Val
1               5                   10                  15

Glu Gln Val Ala Gln Tyr Lys Ala Leu Pro Val
            20                  25

(2) INFORMATION FOR SEQ ID NO: 18:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 18:

Lys Ala Leu Pro Val Val Leu Glu Asn Ala Arg Ile Leu Lys Asn Cys
1               5                   10                  15

Val Asp Ala Lys Met Thr Glu Glu Asp Lys Glu
            20                  25

(2) INFORMATION FOR SEQ ID NO: 19:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 19:

Phe Phe Ala Val Ala Asn Gly Asn Glu Leu Leu Leu Asp Leu Ser Leu
1               5                   10                  15

Thr Lys Val Asn Ala Thr Glu Pro Glu Arg
            20                  25

(2) INFORMATION FOR SEQ ID NO: 20:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 20:

Glu Glu Asp Lys Glu Asn Ala Leu Ser Leu Leu Asp Lys Ile Tyr Thr
```

```
                 1               5                  10                 15
Ser Pro Leu (2) INFORMATION FOR SEQ ID NO: 21:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 21:

Met Gly Glu Ala Val Gln Asn Thr Val Glu Asp Leu Lys Leu Asn Thr
1               5                  10                 15

Leu Gly Arg (2) INFORMATION FOR SEQ ID NO: 22:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 22:

Glu Glu Asp Lys Glu Asn Ala Leu Ser Leu Leu Asp Lys Ile Tyr
1               5                  10                 15

Thr (2) INFORMATION FOR SEQ ID NO: 23:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 23:

Asn Ala Leu Ser Leu Leu Asp Lys Ile Tyr Thr Ser Pro Leu
1               5                  10

(2) INFORMATION FOR SEQ ID NO: 24:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 24:

Phe Tyr Asp Val Phe Phe Ala Val Ala Asn Gly Asn Glu Leu Leu Leu
1               5                  10                 15

Asp
```

(2) INFORMATION FOR SEQ ID NO: 25:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 25:

```
Asn Gly Asn Glu Leu Leu Leu Asp Leu Ser Leu Thr Lys Val Asn Ala
1               5                   10                  15
Thr Glu
```

(2) INFORMATION FOR SEQ ID NO: 26:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 26:

```
Ser Leu Thr Lys Val Asn Ala Thr Glu Pro Glu Arg Thr Ala Met Lys
1               5                   10                  15
Lys Ile
```

(2) INFORMATION FOR SEQ ID NO: 27:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 27:

```
Glu Arg Thr Ala Met Lys Lys Ile Gln Asp Cys Tyr Val Glu Asn Gly
1               5                   10                  15
Leu
```

(2) INFORMATION FOR SEQ ID NO: 28:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 28:

```
Gln Asp Cys Tyr Val Glu Asn Gly Leu Ile Ser Arg Val Leu Asp Gly
1               5                   10                  15
Leu Val
```

(2) INFORMATION FOR SEQ ID NO: 29:

(i) SEQUENCE CHARACTERISTICS:

```
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 29:

Ile Ser Arg Val Leu Asp Gly Leu Val Met Thr Thr Ile Ser Ser Ser
1               5                   10                  15

Lys Asp Cys Met
            20

(2) INFORMATION FOR SEQ ID NO: 30:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 30:

Ile Ser Arg Val Leu Asp Gly Leu Val Met Ile Ala Ile Asn Glu Asp
1               5                   10                  15

Cys Met (2) INFORMATION FOR SEQ ID NO: 31:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 31:

Met Thr Thr Ile Ser Ser Ser Lys Asp Cys Met Gly Glu Ala Val Gln
1               5                   10                  15

Asn Thr Glu Val Glu Leu Asp Lys Leu Asn Thr Leu Gly Phe
            20                  25                  30

(2) INFORMATION FOR SEQ ID NO: 32:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 32:

Met Ile Ala Ile Asn Glu Asp Cys Met Gly Glu Ala Val Gln Asn Thr
1               5                   10                  15

Glu Val Glu Leu Asp Lys Leu Asn Thr Leu Gly Phe
            20                  25

(2) INFORMATION FOR SEQ ID NO: 33:

(i) SEQUENCE CHARACTERISTICS:
```

(A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 33:

TATCGATGAA ATTTGYCCWG CWGT                                              24

(2) INFORMATION FOR SEQ ID NO: 34:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 34:

GCTCGAGRTC YTCYTCWGT                                                    19

(2) INFORMATION FOR SEQ ID NO: 35:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 35:

GGAATTCATC GATGTGAAGA GGGATCTATT C                                      31

(2) INFORMATION FOR SEQ ID NO: 36:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 36:

GGATCGATGA ATTCTATTCC TGACGGGAAC CC                                     32

(2) INFORMATION FOR SEQ ID NO: 37:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 37:

GGATTCTCTA GACTGCAGGT                                                   20

(2) INFORMATION FOR SEQ ID NO: 38:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 38:

GGAATTCTCT AGACTGCAGG T                                              21

(2) INFORMATION FOR SEQ ID NO: 39:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 39:

GAYGARTAYG THGARCARGT                                                20

(2) INFORMATION FOR SEQ ID NO: 40:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 40:

CGGAATTCAA RATGGCNGAR ACDTGYC                                        27

(2) INFORMATION FOR SEQ ID NO: 41:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 41:

CGGGCTGCAG TARCARTCYT GNATYTTYTT CAT                                 33

(2) INFORMATION FOR SEQ ID NO: 42:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 42:

Met Lys Lys Ile Gln Asp Cys Tyr
1               5

(2) INFORMATION FOR SEQ ID NO: 43:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 43:

GGATCGATGA ATTCGGTGGC CAATGGAAAT G                           31

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

ATTACTGTTG GACTTGTCCC T                                      21

(2) INFORMATION FOR SEQ ID NO: 45:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 45:

Leu Leu Leu Asp Leu Ser
1               5

(2) INFORMATION FOR SEQ ID NO: 46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

GGGTCTAGAG GTACCGTCCG ATCGATCATT                             30

(2) INFORMATION FOR SEQ ID NO: 47:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

AATGATCGAT GCT                                               13

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

```
GGGTCTAGAG GTACCGTCCG                                                          20
```

(2) INFORMATION FOR SEQ ID NO: 49:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 49:

```
CGGGCTCGAG CTGCAGCTGT TCTCTCTGGT TCAGT                                          35
```

(2) INFORMATION FOR SEQ ID NO: 50:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 50:

```
Thr Glu Pro Glu Arg Thr
1               5
```

(2) INFORMATION FOR SEQ ID NO: 51:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 51:

```
GGGCTGCAGA TTCTAGTCAG CCTGATTGA                                                 29
```

(2) INFORMATION FOR SEQ ID NO: 52:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

```
GGGCTCGAGC TGCAGTTCTT CAGTATTCTG GCA                                            33
```

(2) INFORMATION FOR SEQ ID NO: 53:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 53:

```
Ala Arg Ile Leu Lys Asn
1               5
```

(2) INFORMATION FOR SEQ ID NO: 54:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 54:

```
Glu Ile Thr Pro Ala Val Lys Arg Asp Val Asp Leu Phe Leu Thr Gly
1               5                   10                  15
Thr
```

(2) INFORMATION FOR SEQ ID NO: 55:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 55:

```
Asp Val Asp Leu Phe Leu Thr Gly Thr Pro Asp Glu Tyr Val Glu Gln
1               5                   10                  15
Val
```

(2) INFORMATION FOR SEQ ID NO: 56:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 56:

```
Asn Ala Arg Ile Leu Lys Asn Cys Val Asp Ala Lys Met Thr Glu Glu
1               5                   10                  15
Asp Lys Glu
```

(2) INFORMATION FOR SEQ ID NO: 57:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 57:

```
Leu Leu Leu Asp Leu Ser Leu Thr Lys Val Asn Ala Thr Glu Pro Glu
1               5                   10                  15
Arg Thr Ala Met Lys Lys Ile Asp Gln Asp Cys
                20                  25
```

(2) INFORMATION FOR SEQ ID NO: 58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 58:

```
GTCCACGGAC ACAAGTGCGA TATCACC                                    27
```

(2) INFORMATION FOR SEQ ID NO: 59:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 59:

```
GTTGGCTTCC TTCACAGGAC AGGAATT                                    27
```

(2) INFORMATION FOR SEQ ID NO: 60:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 60:

```
Val Lys Met Ala Glu Thr Cys Pro Ile Phe Tyr Asp Val Phe Phe Ala
1               5                   10                  15

Val Ala
```

(2) INFORMATION FOR SEQ ID NO: 61:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 10..27

(xi) SEQUENCE DESCRIPTION: SEQ ID NO: 61:

```
GGGGGATCC AAA GCT CTG CCG GTT GTT                                27
          Lys Ala Leu Pro Val Val
            1               5
```

(2) INFORMATION FOR SEQ ID NO: 62:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 62:

Lys Ala Leu Pro Val Val
  1               5

(2) INFORMATION FOR SEQ ID NO: 63:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 10..90

(xi) SEQUENCE DESCRIPTION: SEQ ID NO: 63:

GGGGGATCC AAA GCT CTG CCG GTT GTT CTG GAA AAC GCT CGT ATC CTG        48
          Lys Ala Leu Pro Val Val Leu Glu Asn Ala Arg Ile Leu
            1               5                  10

AAA AAC TGC GTT GAC GCT AAA ATG ACC GAA GAA GAC AAA GAA              90
Lys Asn Cys Val Asp Ala Lys Met Thr Glu Glu Asp Lys Glu
   15                  20                  25

(2) INFORMATION FOR SEQ ID NO: 64:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 64:

Lys Ala Leu Pro Val Val Leu Glu Asn Ala Arg Ile Leu Lys Asn Cys
  1               5                  10                  15

Val Asp Ala Lys Met Thr Glu Glu Asp Lys Glu
               20                  25

(2) INFORMATION FOR SEQ ID NO: 65:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 65:

CAGAGACAGG TCCAGCAGCA GTTCGTTACC GTTAGCAACA GCGAAGAATT CTTTGTCTTC    60

TTC                                                                  63

(2) INFORMATION FOR SEQ ID NO: 66:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 66:

Glu Glu Asp Lys Glu Phe Phe Ala Val Ala Asn Gly Asn Glu Leu Leu
1               5                   10                  15

Leu Asp Leu Ser Leu
            20

(2) INFORMATION FOR SEQ ID NO: 67:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..45

(xi) SEQUENCE DESCRIPTION: SEQ ID NO: 67:

CTG GAC CTG TCT CTG ACC AAA GTT AAC GCT ACC GAA CCG GAA CGT           45
Leu Asp Leu Ser Leu Thr Lys Val Asn Ala Thr Glu Pro Glu Arg
1               5                   10                  15

(2) INFORMATION FOR SEQ ID NO: 68:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 68:

Leu Asp Leu Ser Leu Thr Lys Val Asn Ala Thr Glu Pro Glu Arg
1               5                   10                  15

(2) INFORMATION FOR SEQ ID NO: 69:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 69:

GTCCGGGTA CCGGTCAGGA ACAGGTCAAC GTCACGTTTA CGTTCCGGTT CGGT            54

(2) INFORMATION FOR SEQ ID NO: 70:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 70:

Thr Glu Pro Glu Arg Lys Arg Asp Val Asp Leu Phe Leu Thr Gly Thr
1               5                   10                  15

Pro Asp (2) INFORMATION FOR SEQ ID NO: 71:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..63

(xi) SEQUENCE DESCRIPTION: SEQ ID NO: 71:

```
ACC GGT ACC CCG GAC GAA TAC GTT GAA CAG GTT GCT CAG TAC AAA GCT      48
Thr Gly Thr Pro Asp Glu Tyr Val Glu Gln Val Ala Gln Tyr Lys Ala
  1               5                  10                  15

CTG CCG GTT TAG TAGTCTAGAC TGCAGAAGCT TGGATCCCC                      89
Leu Pro Val
```

(2) INFORMATION FOR SEQ ID NO: 72:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 72:

```
Thr Gly Thr Pro Asp Glu Tyr Val Glu Gln Val Ala Gln Tyr Lys Ala
  1               5                  10                  15

Leu Pro Val
```

(2) INFORMATION FOR SEQ ID NO: 73:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 73:

```
GGGGATCCAA GCTTCTGCAG TCTAGACTAC TAAACCGGCA GAGC                     44
```

(2) INFORMATION FOR SEQ ID NO: 74:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 74:

```
Ala Leu Pro Val
  1
```

(2) INFORMATION FOR SEQ ID NO: 75:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 9..41

(xi) SEQUENCE DESCRIPTION: SEQ ID NO: 75:

```
GGGGATCC GAA GAA GAC AAA GAA AAC GCT CTG TCT CTG CTG         41
         Glu Glu Asp Lys Glu Asn Ala Leu Ser Leu Leu
          1               5                  10
```

(2) INFORMATION FOR SEQ ID NO: 76:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 76:

```
Glu Glu Asp Lys Glu Asn Ala Leu Ser Leu Leu
 1               5                  10
```

(2) INFORMATION FOR SEQ ID NO: 77:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 77:

```
TTCCAGAACA ACCGGCAGAG CTTTCAGCGG AGAGGTGTAG ATTTTGTCCA GCAGAGACAG         60
```

(2) INFORMATION FOR SEQ ID NO: 78:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 78:

```
Leu Ser Leu Leu Asp Lys Ile Tyr Thr Ser Pro Leu Lys Ala Leu Pro
 1               5                  10                  15
Val Val Leu Glu
         20
```

(2) INFORMATION FOR SEQ ID NO: 79:

(i) SEQUENCE CHARACTERISTICS:
        (A) LENGTH: 54 base pairs
        (B) TYPE: nucleic acid
        (C) STRANDEDNESS: single

```
        (D) TOPOLOGY: linear (ii) MOLECULE TYPE: cDNA (iv) ANTI-SENSE: YES (xi) SEQUENCE DESCRIPTION: SEQ ID NO: 79:

TTCAACGGTG TTCTGAACAG CTTCACCCAT AACCGGCAGA GCTTTGTACT GAGC          54

(2) INFORMATION FOR SEQ ID NO: 80:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 80:

Ala Gln Tyr Lys Ala Leu Pro Val Met Gly Glu Ala Val Gln Asn Thr
1               5                   10                  15

Val Glu (2) INFORMATION FOR SEQ ID NO: 81:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..42

(xi) SEQUENCE DESCRIPTION: SEQ ID NO: 81:

CAG AAC ACC GTT GAA GAC CTG AAA CTG AAC ACC CTG GGT CGT             42
Gln Asn Thr Val Glu Asp Leu Lys Leu Asn Thr Leu Gly Arg
  1               5                   10

TGAATGTAAC TGCAGAATTC CCC                                            65

(2) INFORMATION FOR SEQ ID NO: 82:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 82:

Gln Asn Thr Val Glu Asp Leu Lys Leu Asn Thr Leu Gly Arg
  1               5                   10

(2) INFORMATION FOR SEQ ID NO: 83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
```

(A) NAME/KEY: CDS
            (B) LOCATION: 9..20

(xi) SEQUENCE DESCRIPTION: SEQ ID NO: 83:

GGGGATCC GAA GAA GAC AAA                                                    20
         Glu Glu Asp Lys
           1

(2) INFORMATION FOR SEQ ID NO: 84:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 84:

Glu Glu Asp Lys
  1

(2) INFORMATION FOR SEQ ID NO: 85:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO: 85:

GGGGAATTCT GCAGTTACAT TCATCTCCCC AAAGT                                      35

(2) INFORMATION FOR SEQ ID NO: 86:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 86:

Thr Leu Gly Arg
1

(2) INFORMATION FOR SEQ ID NO: 87:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 87:

Leu Val Pro Arg Gly Ser
  1               5

(2) INFORMATION FOR SEQ ID NO: 88:

(i) SEQUENCE CHARACTERISTICS:

```
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 88:

Met Gly His His His His His His Glu Phe
1               5                   10

(2) INFORMATION FOR SEQ ID NO: 89:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 89:

GAATTC                                                                6

(2) INFORMATION FOR SEQ ID NO: 90:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 90:

GGATCC                                                                6

(2) INFORMATION FOR SEQ ID NO: 91:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 91:

Met Gly His His His His His His Leu Val Pro Arg Gly Ser
1               5                   10

(2) INFORMATION FOR SEQ ID NO: 92:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 92:

Lys Met Ala Glu Thr Cys Pro
1               5

(2) INFORMATION FOR SEQ ID NO: 93:
```

(i) SEQUENCE CHARACTERISTICS:
            (A) LENGTH: 5 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 93:

Val Ala Asn Gly Asn
1               5

(2) INFORMATION FOR SEQ ID NO: 94:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iv) ANTI-SENSE: YES (xi) SEQUENCE DESCRIPTION: SEQ ID NO: 94:

ATTGGCCACC GCAAAAAATA CAGGTAGTGC TTTGTA                                    36

(2) INFORMATION FOR SEQ ID NO: 95:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (iv) ANTI-SENSE: YES (xi) SEQUENCE DESCRIPTION: SEQ ID NO: 95:

TAGTGCCTTT TCTCTCTGGT TCAGTAGC                                             28

(2) INFORMATION FOR SEQ ID NO: 96:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (iv) ANTI-SENSE: YES (xi) SEQUENCE DESCRIPTION: SEQ ID NO: 96:

GGGGATCCTT ACTCCTTATC CTCTTCTGT                                            29

(2) INFORMATION FOR SEQ ID NO: 97:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iv) ANTI-SENSE: YES (xi) SEQUENCE DESCRIPTION: SEQ ID NO: 97:

TAGGTCAACA TCCCTCTTCT CCTTATCCTC TTCTGT                                     36

(2) INFORMATION FOR SEQ ID NO: 98:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: cDNA (iv) ANTI-SENSE: YES (xi) SEQUENCE DESCRIPTION: SEQ ID NO: 98:

CGCAAAAAAT ACAGGTAGTG CTTTGTA                                               27

(2) INFORMATION FOR SEQ ID NO: 99:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: cDNA (iv) ANTI-SENSE: YES (xi) SEQUENCE DESCRIPTION: SEQ ID NO: 99:

GGGGATCCTT ATCTCTCTGG TTCAGTAGC                                             29

(2) INFORMATION FOR SEQ ID NO: 100:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: cDNA (iv) ANTI-SENSE: YES (xi) SEQUENCE DESCRIPTION: SEQ ID NO: 100:

TAGGTCAACA TCCCTCTTTC TCTCTGGTTC AGTAGCATT                                  39

(2) INFORMATION FOR SEQ ID NO: 101:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: cDNA (iv) ANTI-SENSE: YES (xi) SEQUENCE DESCRIPTION: SEQ ID NO: 101:

GGGGATCCTC ACTCCTTATC CTCTTCTGTC AT                                         32

(2) INFORMATION FOR SEQ ID NO: 102:

(i) SEQUENCE CHARACTERISTICS:
         (A) LENGTH: 288 base pairs
         (B) TYPE: nucleic acid
         (C) STRANDEDNESS: single -continued

```
      (D) TOPOLOGY: linear (ii) MOLECULE TYPE: cDNA (ix) FEATURE:
       (A) NAME/KEY: CDS
       (B) LOCATION: 1..288

(xi) SEQUENCE DESCRIPTION: SEQ ID NO: 102:

ATG GGT CAC CAC CAC CAC CAC CAC GAA TTC CTG GTT CCG CGT GGA TCC        48
Met Gly His His His His His His Glu Phe Leu Val Pro Arg Gly Ser
 1               5                  10                  15

AAA GCT CTG CCG GTT GTT CTG GAA AAC GCT CGT ATC CTG AAA AAC TGC        96
Lys Ala Leu Pro Val Val Leu Glu Asn Ala Arg Ile Leu Lys Asn Cys
                20                  25                  30

GTT GAC GCT AAA ATG ACC GAA GAA GAC AAA GAA TTC TTC GCT GTT GCT       144
Val Asp Ala Lys Met Thr Glu Glu Asp Lys Glu Phe Phe Ala Val Ala
             35                  40                  45

AAC GGT AAC GAA CTG CTG CTG GAC CTG TCT CTG ACC AAA GTT AAC GCT       192
Asn Gly Asn Glu Leu Leu Leu Asp Leu Ser Leu Thr Lys Val Asn Ala
         50                  55                  60

ACC GAA CCG GAA CGT AAA CGT GAC GTT GAC CTG TTC CTG ACC GGT ACC       240
Thr Glu Pro Glu Arg Lys Arg Asp Val Asp Leu Phe Leu Thr Gly Thr
 65                  70                  75                  80

CCG GAC GAA TAC GTT GAA CAG GTT GCT CAG TAC AAA GCT CTG CCG GTT       288
Pro Asp Glu Tyr Val Glu Gln Val Ala Gln Tyr Lys Ala Leu Pro Val
                 85                  90                  95

(2) INFORMATION FOR SEQ ID NO: 103:

(i) SEQUENCE CHARACTERISTICS:
         (A) LENGTH: 96 amino acids
         (B) TYPE: amino acid
         (D) TOPOLOGY: linear (ii) MOLECULE TYPE: protein (xi) SEQUENCE DESCRIPTION: SEQ ID NO: 103:

Met Gly His His His His His His Glu Phe Leu Val Pro Arg Gly Ser
 1               5                  10                  15

Lys Ala Leu Pro Val Val Leu Glu Asn Ala Arg Ile Leu Lys Asn Cys
                20                  25                  30

Val Asp Ala Lys Met Thr Glu Glu Asp Lys Glu Phe Phe Ala Val Ala
             35                  40                  45

Asn Gly Asn Glu Leu Leu Leu Asp Leu Ser Leu Thr Lys Val Asn Ala
         50                  55                  60

Thr Glu Pro Glu Arg Lys Arg Asp Val Asp Leu Phe Leu Thr Gly Thr
 65                  70                  75                  80

Pro Asp Glu Tyr Val Glu Gln Val Ala Gln Tyr Lys Ala Leu Pro Val
                 85                  90                  95
```